US012110278B2

(12) United States Patent
Jorgensen et al.

(10) Patent No.: US 12,110,278 B2
(45) Date of Patent: Oct. 8, 2024

(54) SELECTIVE JAK2 PSEUDOKINASE LIGANDS AND METHODS OF USE

(71) Applicant: YALE UNIVERSITY, New Haven, CT (US)

(72) Inventors: William L. Jorgensen, Deep River, CT (US); Joseph Schlessinger, Woodbridge, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 17/500,622

(22) Filed: Oct. 13, 2021

(65) Prior Publication Data

US 2022/0112166 A1 Apr. 14, 2022

Related U.S. Application Data

(60) Provisional application No. 63/091,001, filed on Oct. 13, 2020.

(51) Int. Cl.
| | | |
|---|---|---|
| C07D 249/14 | (2006.01) | |
| A61K 31/4196 | (2006.01) | |
| A61K 31/4245 | (2006.01) | |
| A61K 31/4439 | (2006.01) | |
| A61K 45/06 | (2006.01) | |
| C07D 401/12 | (2006.01) | |
| C07D 405/12 | (2006.01) | |
| C07D 413/12 | (2006.01) | |

(52) U.S. Cl.
CPC ........ *C07D 249/14* (2013.01); *A61K 31/4196* (2013.01); *A61K 31/4245* (2013.01); *A61K 31/4439* (2013.01); *A61K 45/06* (2013.01); *C07D 401/12* (2013.01); *C07D 405/12* (2013.01); *C07D 413/12* (2013.01)

(58) Field of Classification Search
CPC . C07D 249/14; C07D 401/12; A61K 31/4196
See application file for complete search history.

(56) References Cited

U.S. PATENT DOCUMENTS

| | | | | |
|---|---|---|---|---|
| 7,317,031 B2* | 1/2008 | Lin | ...................... | C07D 417/06 548/266.2 |
| 7,598,288 B2* | 10/2009 | Hellberg | ................. | A61P 43/00 514/424 |
| 11,472,799 B2* | 10/2022 | Jin | ....................... | C07D 401/14 |

OTHER PUBLICATIONS

Cutrona, Kara J., et al., "Metadynamics as a Post-Processing Method for Virtual Screening with Application to the Pseudokinase Domain of JAK2", J. Chem. Inf. Model., Pharmaceutical Modeling, May 8, 2020, DOI: 10.1021/acs.jcim. 0c00276 [retrieved on May 9, 2020].

Liosi, Maria-Elena, et al., "Selective Janus Kinase 2 (JAK2) Pseudokinase Ligands with a Diaminotriazole Core", J. Med. Chem., vol. 63, Apr. 24, 2020, pp. 5324-5340.

Newton, Ana S., et al., "Indoloxytriazines as binding molecules for the JAK2 JH2 pseudokinase domain and its V617F variant", Tetrahedron Letters, Jul. 2, 2021, vol. 77, 153248.

Newton, Ana S., et al., "JAK2 JH2 Fluorescence Polarization Assay and Crystal Structures for Complexes with Three Small Molecules", ACS Med. Chem. Lett. 2017, vol. 8, pp. 614-617.

Puleo, David E., et al., "Identification and Characterization of JAK2 Pseudokinase Domain Small Molecule Binders", ACS Med. Chem. Lett., vol. 8, May 2017, pp. 618-621.

* cited by examiner

*Primary Examiner* — Kamal A Saeed
(74) *Attorney, Agent, or Firm* — Saul Ewing LLP; Domingos J. Silva; Dennis Ostrovsky

(57) ABSTRACT

The compounds of Formula I described herein regulate activity of JAK2 by specifically binding to the JAK2 pseudokinase domain, JH2, and are useful as therapeutic agents in the treatment or amelioration of myeloproliferative disorders. Also provided herein are methods of treating myeloproliferative disorders, and methods of making compounds of Formula I.

21 Claims, 13 Drawing Sheets

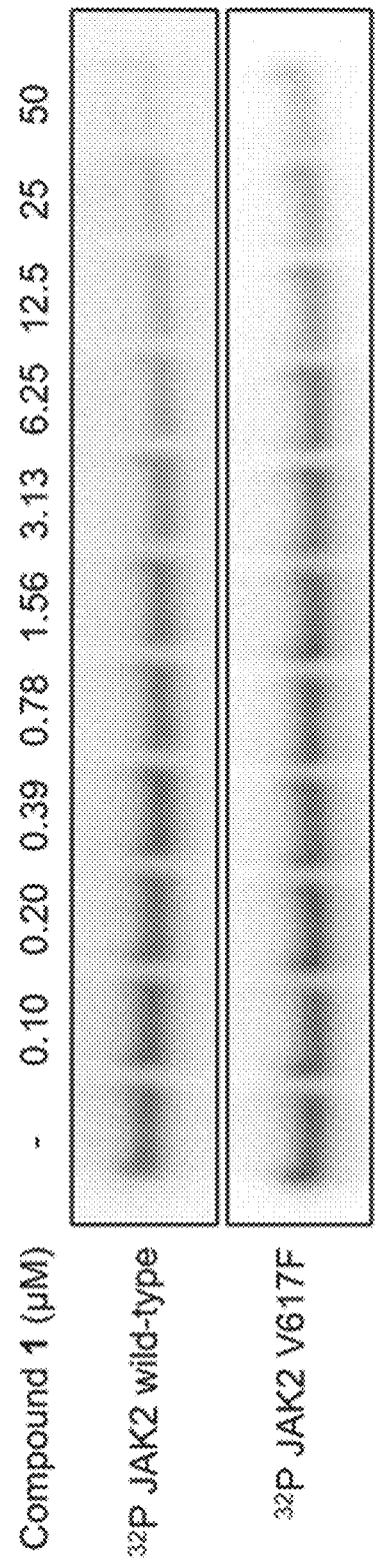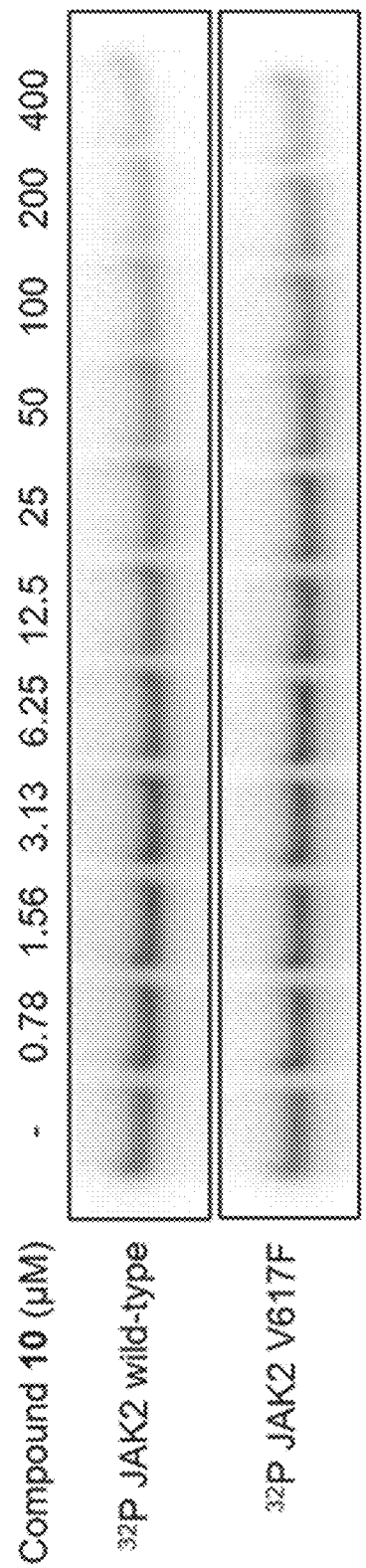
FIG. 11A
FIG. 11B

SELECTIVE JAK2 PSEUDOKINASE LIGANDS AND METHODS OF USE

CROSS-REFERENCE TO RELATED APPLICATION

This application claims priority to U.S. Provisional Patent Application Ser. No. 63/091,001 entitled "SELECTIVE JAK2 PSEUDOKINASE LIGANDS AND METHODS OF USE," filed Oct. 13, 2020, the disclosure of which is incorporated herein by reference in its entirety.

STATEMENT REGARDING FEDERALLY SPONSORED RESEARCH

This invention was made with government support under OD001800, GM032136, and GM007324 awarded by National Institutes of Health and under DE-AC02-06CH11357 awarded by the Department of Energy. The government has certain rights in the invention.

BACKGROUND

Janus kinases (JAKs) are a family of non-receptor tyrosine kinases that are essential components of the JAK-STAT signaling pathway. Aberrant signaling in this cascade is responsible for numerous diseases, including disorders of the immune system and many forms of cancer. Specifically, the Val617Phe mutation in JH2 stimulates the activity of the adjacent kinase domain (JH1) resulting in myeloproliferative disorders.

There is an ever-present need to develop new therapies to treat myeloproliferative disorders, such as chronic myelogenous leukemia (CML), polycythemia vera, primary myelofibrosis (also called chronic idiopathic myelofibrosis), essential thrombocythemia, chronic neutrophilic leukemia, and chronic eosinophilic leukemia. The present invention addresses and meets this need.

BRIEF SUMMARY OF THE INVENTION

In one aspect, a compound of Formula I, or a pharmaceutically acceptable salt or tautomer thereof is provided. The compound of Formula I has the structure:
wherein,

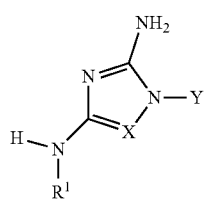

Formula I wherein,
Y is selected from the group consisting of —$CH_2$—$R^2$, —C(=O)$NR^2R^3$, optionally substituted $C_{5\text{-}10}$ heteroaryl, and optionally substituted $C_{5\text{-}6}$ heterocycloalkyl;
wherein the optional substitution is independently at least one substituent selected from the group consisting of $C_{1\text{-}5}$ alkyl, $C_{1\text{-}5}$ alkoxy, $C_{1\text{-}5}$ thioalkyl, $C_{1\text{-}5}$ aminoalkyl, $C_{5\text{-}10}$ aryl, $C_{5\text{-}10}$ heteroaryl, =O (oxo), F, Cl, Br, I, C(=O)OR, NHC(=O)R, and OH;

$R^1$ and $R^2$ are each independently selected from the group consisting of $C_{2\text{-}6}$ alkenyl, $C_{3\text{-}7}$ cycloalkyl, $C_{6\text{-}10}$ aryl, 5-10 membered heteroaryl, 4-10 membered heterocycloalkyl, $C_{6\text{-}10}$-5-6 membered heterobiaryl, 5-6 membered $C_{6\text{-}10}$ heterobiaryl, and $C_{6\text{-}10}$—$C_{6\text{-}10}$ biaryl,
each one independently optionally substituted by at least one substituent selected from the group consisting of F, Cl, Br, I, OR, OC(=O)N(R)$_2$, CN, NO$_2$, CF$_3$, OCF$_3$, R, N(R)$_2$, SR, SOR, SO$_2$R, SO$_2$N(R)$_2$, SO$_3$R, C(=O)R, C(=O)OR, OC(=O)R, O(CH$_2$)$_{0\text{-}2}$C(=O)OR, C(=O)N(R)$_2$, OC(=O)N(R)$_2$, (CH$_2$)$_{0\text{-}2}$N(R)C(=O)R, N(R)SO$_2$R, N(R)C(=O)OR, N(R)C(=O)R, N(R)C(=O)N(R)$_2$, and C(=NH)N(R)$_2$,
wherein each occurrence of R is independently selected from the group consisting of hydrogen and ($C_1$-$C_6$) hydrocarbyl; or wherein two R groups bonded to a nitrogen atom or to adjacent nitrogen atoms can together with the nitrogen atom or atoms form a heterocyclyl;
$R^3$ is H or $C_{1\text{-}4}$ hydrocarbyl;
X is N or C—$R^4$, wherein $R^4$ is H or $C_{1\text{-}4}$ hydrocarbyl optionally substituted by 1 to 3 substituents selected from the group consisting of OR', NHR', and NR'$_2$,
wherein each occurrence of R' is independently selected from the group consisting of hydrogen and ($C_1$-$C_6$)hydrocarbyl; or wherein two R' groups bonded to a nitrogen atom or to adjacent nitrogen atoms can together with the nitrogen atom or atoms form a heterocyclyl.

Compounds of Formula I, in some aspects, are useful in preventing, treating, and/or ameliorating a myeloproliferative neoplasm in a patient in a patient in need thereof. Examples of the myeloproliferative neoplasm that can be treated or ameliorated include, but are not limited to, chronic myelogenous leukemia (CML), polycythemia vera, primary myelofibrosis, essential thrombocythemia, chronic neutrophilic leukemia, and chronic eosinophilic leukemia.

BRIEF DESCRIPTION OF THE FIGURES

The drawings illustrate generally, by way of example, but not by way of limitation, various embodiments of the present application.

(FIG. 1B) 1 bound to JAK2 JH1 (PDB ID 5USY). Hydrogen bonds with $r_{ON}$<3.6 Å are indicated with dashed lines.

(FIG. 8A) Variation of FP values as a function of JAK2-JH2-WT, JAK2-JH2-V617F, and JAK2-JH1 concentration. (FIG. 8B) $K_d$ determination for JAK2-JH2-WT, JAK2-JH2-VF, and JAK2-JH1. Lb/Lt=ratio of ligand bound to the total. Data from quadruplicate experiments in three independent assays. Mean±SEM plotted for all data.

FIGS. 11A-11B show in vitro [γ-$^{32}$P]ATP kinase activity assay of immunoprecipitated full-length JAK2. Autoradiography of autophosphorylated JAK2 wild-type and V617F mutant exposed to different concentrations of (FIG. 11A) 1, and (FIG. 11B) 10. Shown is representative data from experiments performed in triplicate.

DETAILED DESCRIPTION OF THE INVENTION

Figure 1A:
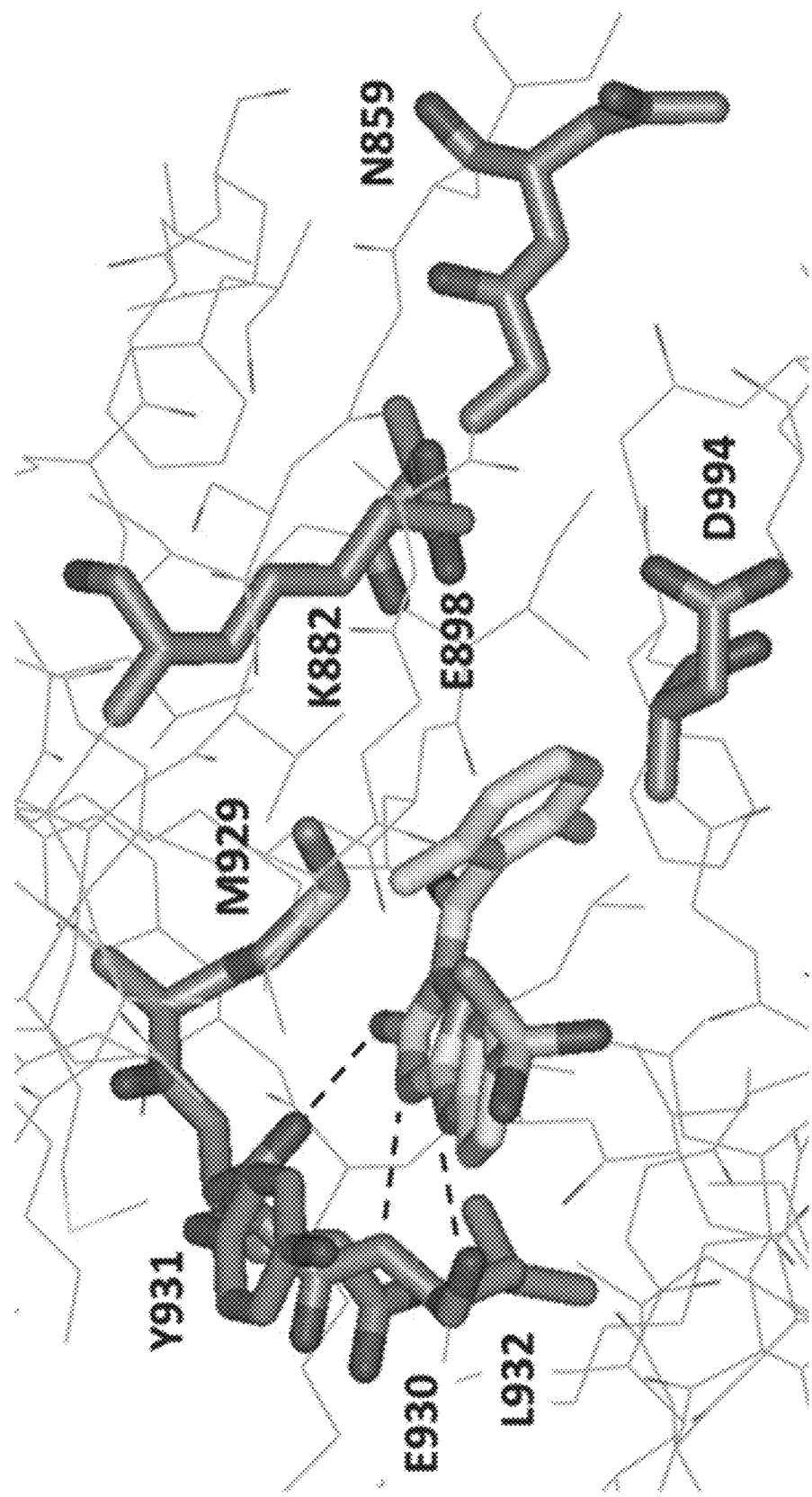
FIGS. 1A-1B show (FIG. 1A) 1 bound to JAK2 JH2 (PDB ID 5USZ)

The invention provides certain compounds that are, in various embodiments, selective inhibitors of the JAK2 JH2 domain (a pseudokinase domain). JH2 domains do have a regulatory function for the JH1 kinase activity, such that mutations in JH2 can cause hyperactivation leading to numerous diseases and cancer.

In certain non-limiting embodiments of the invention, the compounds contemplated herein bind to the JAK2 JH2 ATP binding site with selectivity over the corresponding JAK2 JH1 ATP binding site. In certain embodiments, the compounds contemplated herein selectively reverse the activating effect of certain proliferative mutations (such as, but not limited to, V617F) in JAK2 JH2.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. All publications, patents, and patent documents referred to in this document are incorporated by reference herein in their entirety, as though individually incorporated by reference.

In the methods described herein, the acts can be carried out in any order, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

Definitions

The term "about" as used herein can allow for a degree of variability in a value or range, for example, within 10%, within 5%, or within 1% of a stated value or of a stated limit of a range, and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%. The term "substantially free of" as used herein can mean having none or having a trivial amount of, such that the amount of material present does not affect the material properties of the composition including the material, such that the composition is about 0 wt % to about 5 wt % of the material, or about 0 wt % to about 1 wt %, or about 5 wt % or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less. The term "substantially free of" can mean having a trivial amount of, such that a composition is about 0 wt % to about 5 wt % of the material, or about 0 wt % to about 1 wt %, or about 5 wt % or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less, or about 0 wt %.

The term "organic group" as used herein refers to any carbon-containing functional group. Examples can include an oxygen-containing group such as an alkoxy group, aryloxy group, aralkyloxy group, oxo(carbonyl) group; a carboxyl group including a carboxylic acid, carboxylate, and a carboxylate ester; a sulfur-containing group such as an alkyl and aryl sulfide group; and other heteroatom-containing groups. Non-limiting examples of organic groups include OR, OOR, OC(O)N(R)$_2$, CN, CF$_3$, OCF$_3$, R, C(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, C(=NOR)R, and substituted or unsubstituted (C$_1$-C$_{100}$)hydrocarbyl, wherein R can be hydrogen (in examples that include other carbon atoms) or a carbon-based moiety, and wherein the carbon-based moiety can be substituted or unsubstituted.

The term "substituted" as used herein in conjunction with a molecule or an organic group as defined herein refers to the state in which one or more hydrogen atoms contained therein are replaced by one or more non-hydrogen atoms. The substitution can be direct substitution, whereby the hydrogen atom is replaced by a functional group or substituent, or an indirect substitution, whereby an intervening linker group replaces the hydrogen atom, and the substituent or functional group is bonded to the intervening linker group. A non-limiting example of direct substitution is: RR—H→RR—Cl, wherein RR is an organic moiety/fragment/molecule. A non-limiting example of indirect substitution is: RR—H→RR-(LL)$_{zz}$-Cl, wherein RR is an organic moiety/fragment/molecule, (LL)$_{zz}$ is an intervening linker group, and 'zz' is an integer from 0 to 100 inclusive. When zz is 0, LL is absent, and direct substitution results. LL is at each occurrence independently selected from the group consisting of —H, —O—, —OR, —S—, —S(=O)—, —S(=O)$_2$—, —SR, —N(R)—, —NR$_2$, —CR—, —CH$_2$—, —CHR—, —CR$_2$—, —CH$_3$, —C(=O)—, —C(=NR)—, and combinations thereof. (LL)$_{zz}$ can be linear, branched, cyclic, and/or combinations thereof.

The term "functional group" or "substituent" as used herein refers to a group that can be or is substituted onto a molecule or onto an organic group. Examples of substituents or functional groups include, but are not limited to, a halogen (e.g., F, Cl, Br, and I); an oxygen atom in groups such as hydroxy groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxyamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, and C(=NOR)R, wherein R can be hydrogen or a carbon-based moiety; for example, R can be hydrogen, (C$_1$-C$_{100}$)hydrocarbyl, alkyl, acyl, cycloalkyl, aryl, aralkyl, heterocyclyl, heteroaryl, or heteroarylalkyl; or wherein two R groups bonded to a nitrogen atom or to adjacent nitrogen atoms can together with the nitrogen atom or atoms form a heterocyclyl.

The term "alkyl" as used herein refers to straight chain and branched alkyl groups and cycloalkyl groups having from 1 to 40 carbon atoms, 1 to about 20 carbon atoms, 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to straight and branched chain and cyclic alkyl groups as defined herein, except that at least one double bond exists between two carbon atoms. Thus, alkenyl groups have from 2 to 40 carbon atoms, or 2 to about 20 carbon atoms, or 2 to 12 carbon atoms or, in some embodiments, from 2 to 8 carbon atoms. Examples include, but are not limited to vinyl, —CH=C=CCH$_2$, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl among others.

The term "alkynyl" as used herein refers to straight and branched chain alkyl groups, except that at least one triple bond exists between two carbon atoms. Thus, alkynyl groups have from 2 to 40 carbon atoms, 2 to about 20 carbon atoms, or from 2 to 12 carbons or, in some embodiments, from 2 to 8 carbon atoms. Examples include, but are not limited to —C≡CH, —CC(CH$_3$), —C≡C(CH$_2$CH$_3$), —CH$_2$C≡CH, —CH$_2$C≡C(CH$_3$), and —CH$_2$C≡C(CH$_2$CH$_3$) among others.

The term "acyl" as used herein refers to a group containing a carbonyl moiety wherein the group is bonded via the carbonyl carbon atom. The carbonyl carbon atom is bonded to a hydrogen forming a "formyl" group or is bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. An acyl group can include 0 to about 12, 0 to about 20, or 0 to about 40 additional carbon atoms bonded to the carbonyl group. An acyl group can include double or triple bonds within the meaning herein. An acryloyl group is an example of an acyl group. An acyl group can also include heteroatoms within the meaning herein. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "cycloalkyl" as used herein refers to cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined herein. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The term "heterocycloalkyl" as used herein refers to a cycloalkyl group as defined herein in which one or more carbon atoms in the ring are replaced by a heteroatom such as O, N, S, P, and the like, each of which may be substituted as described herein if an open valence is present, and each may be in any suitable stable oxidation state.

The term "aryl" as used herein refers to cyclic aromatic hydrocarbon groups that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, a phenyl group substituted at any one or more of 2-, 3-, 4-, 5-, or 6-positions of the phenyl ring, or a naphthyl group substituted at any one or more of 2- to 8-positions thereof.

The term "aralkyl" as used herein refers to alkyl groups as defined herein in which a hydrogen or carbon bond of an alkyl group is replaced with a bond to an aryl group as defined herein. Representative aralkyl groups include benzyl and phenylethyl groups and fused (cycloalkylaryl)alkyl groups such as 4-ethyl-indanyl. Aralkenyl groups are alkenyl groups as defined herein in which a hydrogen or carbon bond of an alkyl group is replaced with a bond to an aryl group as defined herein.

The term "heterocyclyl" as used herein refers to aromatic and non-aromatic ring compounds containing three or more ring members, of which one or more is a heteroatom such as, but not limited to, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms equals the total number of ring atoms. A heterocyclyl ring can also include one or more double bonds. A heteroaryl ring is an embodiment of a heterocyclyl group. The phrase "heterocyclyl group" includes fused ring species including those that include fused aromatic and non-aromatic groups. For example, a dioxolanyl ring and a benzdioxolanyl ring system (methylenedioxyphenyl ring system) are both heterocyclyl groups within the meaning herein. The phrase also includes polycyclic ring systems containing a heteroatom such as, but not limited to, quinuclidyl. Heterocyclyl groups can be unsubstituted, or can be substituted as discussed herein. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups such as those listed herein.

The term "heteroaryl" as used herein refers to aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure. A heteroaryl group designated as a $C_2$-heteroaryl can be a 5-ring with two carbon atoms and three heteroatoms, a 6-ring with two carbon atoms and four heteroatoms and so forth. Likewise a $C_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed herein. Representative substituted heteroaryl groups can be substituted one or more times with groups such as those listed herein.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

The term "heterocyclylalkyl" as used herein refers to alkyl groups as defined herein in which a hydrogen or carbon bond of an alkyl group as defined herein is replaced with a bond to a heterocyclyl group as defined herein. Representative heterocyclyl alkyl groups include, but are not limited to, furan-2-yl methyl, furan-3-yl methyl, pyridine-3-yl methyl, tetrahydrofuran-2-yl ethyl, and indol-2-yl propyl.

The term "heteroarylalkyl" as used herein refers to alkyl groups as defined herein in which a hydrogen or carbon bond of an alkyl group is replaced with a bond to a heteroaryl group as defined herein.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include about 1 to about 12, about 1 to about 20, or about 1 to about 40 carbon atoms bonded to the oxygen atom, and can further include double or triple bonds, and can also include heteroatoms. For example, an allyloxy group or a methoxyethoxy group is also an alkoxy group within the meaning herein, as is a methylenedioxy group in a context where two adjacent atoms of a structure are substituted therewith.

The term "thioalkyl" as used herein refers to a sulfur atom connected to an alkyl group, as defined herein. The alkyl group in the thioalkyl can be straight chained or branched. Examples of linear thioalkyl groups include but are not limited to thiomethyl, thioethyl, thiopropyl, thiobutyl, thiopentyl, thiohexyl, and the like. Examples of branched alkoxy include but are not limited to iso-thiopropyl, sec-thiobutyl, tert-thiobutyl, iso-thiopentyl, iso-thiohexyl, and the like. The sulfur atom can appear at any suitable position in the alkyl chain, such as at the terminus of the alkyl chain or anywhere within the alkyl chain.

The term "aminoalkyl" as used herein refers to amine connected to an alkyl group, as defined herein. The amine group can appear at any suitable position in the alkyl chain, such as at the terminus of the alkyl chain or anywhere within the alkyl chain.

The term "amine" as used herein refers to primary, secondary, and tertiary amines having, e.g., the formula N(group)$_3$ wherein each group can independently be H or non-H, such as alkyl, aryl, and the like. Amines include but are not limited to R—NH$_2$, for example, alkylamines, arylamines, alkylarylamines; R$_2$NH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form —NH$_2$, —NHR, —NR$_2$, —NR$_3^+$, wherein each R is independently selected, and protonated forms of each, except for —NR$_3^+$, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino, dialkylamino, and trialkylamino group.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

The terms "epoxy-functional" or "epoxy-substituted" as used herein refers to a functional group in which an oxygen atom, the epoxy substituent, is directly attached to two adjacent carbon atoms of a carbon chain or ring system. Examples of epoxy-substituted functional groups include, but are not limited to, 2,3-epoxypropyl, 3,4-epoxybutyl, 4,5-epoxypentyl, 2,3-epoxypropoxy, epoxypropoxypropyl, 2-glycidoxyethyl, 3-glycidoxypropyl, 4-glycidoxybutyl, 2-(glycidoxycarbonyl)propyl, 3-(3,4-epoxycylohexyl)propyl, 2-(3,4-epoxycyclohexyl)ethyl, 2-(2,3-epoxycylopentyl) ethyl, 2-(4-methyl-3,4-epoxycyclohexyl)propyl, 2-(3,4-epoxy-3-methylcylohexyl)-2-methylethyl, and 5,6-epoxyhexyl.

The term "monovalent" as used herein refers to a substituent connecting via a single bond to a substituted molecule. When a substituent is monovalent, such as, for example, F or Cl, it is bonded to the atom it is substituting by a single bond.

The term "hydrocarbon" or "hydrocarbyl" as used herein refers to a molecule or functional group that includes carbon and hydrogen atoms. The term can also refer to a molecule or functional group that normally includes both carbon and hydrogen atoms but wherein all the hydrogen atoms are substituted with other functional groups.

As used herein, the term "hydrocarbyl" refers to a functional group derived from a straight chain, branched, or cyclic hydrocarbon, and can be alkyl, alkenyl, alkynyl, aryl, cycloalkyl, acyl, or any combination thereof. Hydrocarbyl groups can be shown as $(C_a-C_b)$hydrocarbyl, wherein a and b are integers and mean having any of a to b number of carbon atoms. For example, $(C_1-C_4)$hydrocarbyl means the hydrocarbyl group can be methyl $(C_1)$, ethyl $(C_2)$, propyl $(C_3)$, or butyl $(C_4)$, and $(C_0-C_b)$hydrocarbyl means in certain embodiments there is no hydrocarbyl group. In certain embodiments, the hydrocarbyl is an alkyl group.

As used herein, the term "$C_{6-10}$-5-6 membered heterobiaryl" means a $C_{6-10}$ aryl moiety covalently bonded through a single bond to a 5- or 6-membered heteroaryl moiety. The $C_{6-10}$ aryl moiety and the 5-6-membered heteroaryl moiety can be any of the suitable aryl and heteroaryl groups described herein. Non-limiting examples of a $C_{6-10}$-5-6 membered heterobiaryl include

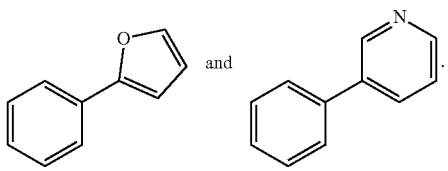 [SMILES: c1ccc(-c2ccco2)cc1 ; c1ccc(-c2cccnc2)cc1]

When the $C_{6-10}$-5-6 membered heterobiaryl is listed as a substituent (e.g., as an "R" group), the $C_{6-10}$-5-6 membered heterobiaryl is bonded to the rest of the molecule through the $C_{6-10}$ moiety.

As used herein, the term "5-6 membered-$C_{6-10}$ heterobiaryl" is the same as a $C_{6-10}$-5-6 membered heterobiaryl, except that when the 5-6 membered-$C_{6-10}$ heterobiaryl is listed as a substituent (e.g., as an "R" group), the 5-6 membered-$C_{6-10}$ heterobiaryl is bonded to the rest of the molecule through the 5-6-membered heteroaryl moiety.

As used herein, the term "$C_{6-10}$—$C_{6-10}$ biaryl" means a $C_{6-10}$ aryl moiety covalently bonded through a single bond to another $C_{6-10}$ aryl moiety. The $C_{6-10}$ aryl moiety can be any of the suitable aryl groups described herein. Non-limiting example of a $C_{6-10}$—$C_{6-10}$ biaryl include biphenyl and binaphthyl.

The term "solvent" as used herein refers to a liquid that can dissolve a solid, liquid, or gas. Non-limiting examples of solvents are silicones, organic compounds, water, alcohols, ionic liquids, and supercritical fluids.

The term "independently selected from" as used herein refers to referenced groups being the same, different, or a mixture thereof, unless the context clearly indicates otherwise. Thus, under this definition, the phrase "$X^1$, $X^2$, and $X^3$ are independently selected from noble gases" would include the scenario where, for example, $X^1$, $X^2$, and $X^3$ are all the same, where $X^1$, $X^2$, and $X^3$ are all different, where $X^1$ and $X^2$ are the same but $X^3$ is different, and other analogous permutations.

The term "room temperature" as used herein refers to a temperature of about 15° C. to 28° C.

The term "standard temperature and pressure" as used herein refers to 20° C. and 101 kPa.

As used herein, the term "composition" or "pharmaceutical composition" refers to a mixture of at least one compound described herein with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "efficacy" refers to the maximal effect (Emax) achieved within an assay. As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the language "pharmaceutically acceptable salt" refers to a salt of the administered compounds prepared from pharmaceutically acceptable non-toxic acids or bases, including inorganic acids or bases, organic acids or bases, solvates, hydrates, or clathrates thereof.

Suitable pharmaceutically acceptable acid addition salts may be prepared from an inorganic acid or from an organic acid. Examples of inorganic acids include hydrochloric, hydrobromic, hydriodic, nitric, carbonic, sulfuric (including sulfate and hydrogen sulfate), and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, malonic, saccharin, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Suitable pharmaceutically acceptable base addition salts of compounds described herein include, for example, ammonium salts, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methyl-glucamine) and procaine. All of these salts may be prepared from the corresponding compound by reacting, for example, the appropriate acid or base with the compound.

As used herein, the term "pharmaceutically acceptable carrier" or "pharmaceutically acceptable excipient" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound described herein within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound(s) described herein, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound(s) described herein, and are physiologically acceptable to the patient. Supplementary active compounds may also be incorporated into the compositions. The "pharmaceutically acceptable carrier" may further include a pharmaceutically acceptable salt of the compound(s) described herein. Other additional ingredients that may be included in the pharmaceutical compositions used with the methods or compounds described herein are known in the art and described, for example in Remington's Pharmaceutical Sciences (Genaro, Ed., Mack Publishing Co., 1985, Easton, PA), which is incorporated herein by reference.

The terms "patient," "subject," or "individual" are used interchangeably herein, and refer to any animal, or cells thereof whether in vitro or in situ, amenable to the methods described herein. In a non-limiting embodiment, the patient, subject or individual is a human.

As used herein, the term "potency" refers to the dose needed to produce half the maximal response ($ED_{50}$).

A "therapeutic" treatment is a treatment administered to a subject who exhibits signs of pathology, for the purpose of diminishing or eliminating those signs.

As used herein, the term "treatment" or "treating" is defined as the application or administration of a therapeutic agent, i.e., a compound or compounds as described herein (alone or in combination with another pharmaceutical agent), to a patient, or application or administration of a therapeutic agent to an isolated tissue or cell line from a patient (e.g., for diagnosis or ex vivo applications), who has a condition contemplated herein or a symptom of a condition contemplated herein, with the purpose to cure, heal, alleviate, relieve, alter, remedy, ameliorate, improve or affect a condition contemplated herein, or the symptoms of a condition contemplated herein. Such treatments may be specifically tailored or modified, based on knowledge obtained from the field of pharmacogenomics.

Preparation of Compounds

Compounds of Formula I or otherwise described herein can be prepared by the general schemes described herein, using the synthetic method known by those skilled in the art. The following examples illustrate non-limiting embodiments of the compound(s) described herein and their preparation.

Compounds numbered 2-15, as shown below, were prepared according to the general approach illustrated with the synthetic route for Compound 12 in Scheme 1.

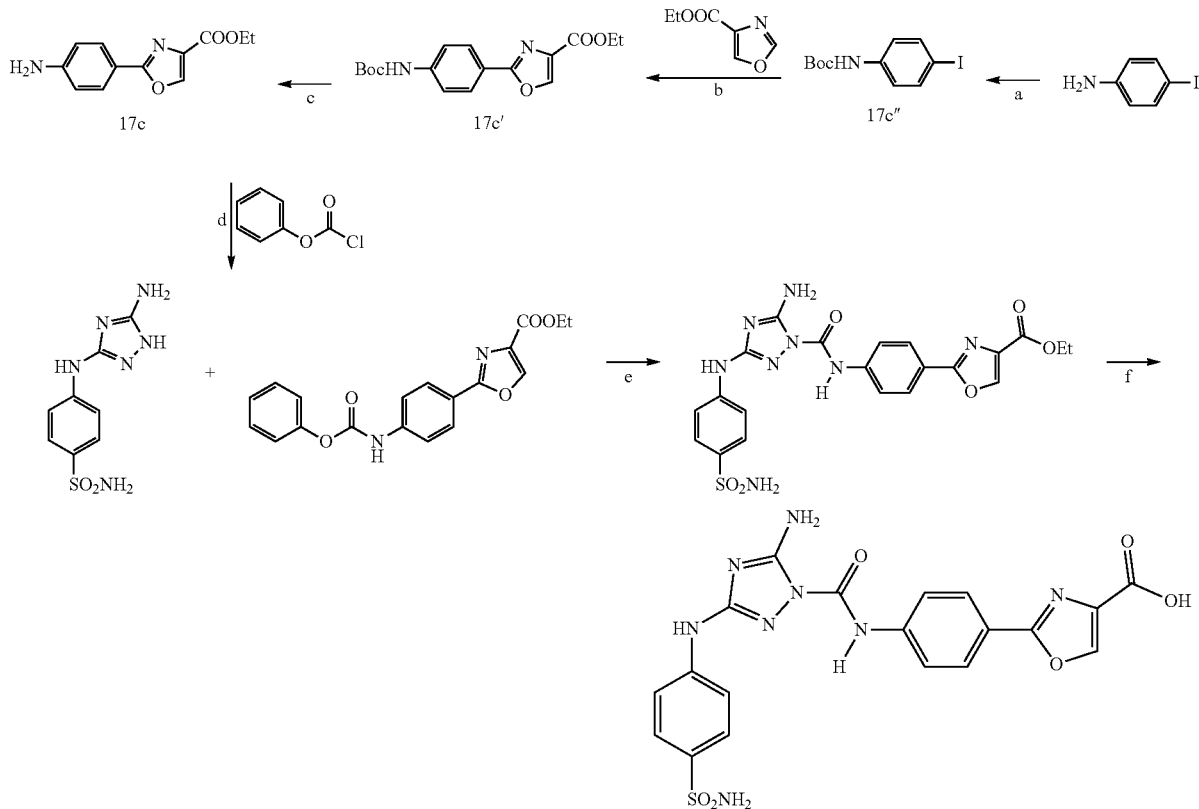

[a]Reagents and conditions:
(a) Boc$_2$O, Et$_3$N, iPrOH, r.t., 14 h;
(b) 10 mol % Pd(OAc)$_2$, 20 mol % JohnPhos, Cs$_2$CO$_3$, dioxane, 110° C., 19 h;
(c) TFA, DCM, 0° C. to r.t., 30 min;
(d) NaHCO$_3$, H$_2$O/THF, 0° C., 1 h;
(e) Et$_3$N, dioxane, 110° C., 50 min;
(f) DBN, LiBr, MeCN, 2 vol % H$_2$O, r.t., 68 h.

A coupling step in this synthetic scheme is the regioselective acylation of a 1H-[1,2,4]triazole-3,5-diamine with a phenylcarbamate. One challenge observed in the synthesis of compounds of Formula I appeared to be associated with the poor solubility in organic solvents for the polar diaminotriazole precursor and the presence of its tautomeric 2—H form, which leads to the undesirable (and difficult-to-separate) regioisomeric 2—H byproduct. In some embodiments, a phenyl carbamate is coupled to a diaminotriazole to provide compounds of Formula I. This approach is effective in generating the desired products when dioxane was used as the solvent, but the yields were not optimal since the problems with the diaminotriazole precursor remained. Better results were obtained by increasing the reaction temperature from 80 to 110° C., extending the reaction time, and diluting the mixture from 1.0 to 0.5 M to improve dissolution of the diaminotriazole.

In various embodiments, the reaction temperature for step 'e' in Scheme 1 is equal to, at least, or greater than about 85° C., 90° C., 95° C., 100° C., 105° C., 110° C., or 115° C. In various embodiments, the reaction temperature for step 'e' in Scheme 1 is about 85° C. to 115° C., 90° C. to 115° C., 95° C. to 115° C., or about 100° C. to 115° C. In some embodiments, the concentration of the diaminotriazole precursor in the reaction mixture prior to reaction with the phenyl carbamate is about 0.25 M, 0.3 M, 0.35 M, 0.4 M, 0.45 M, 0.5 M, 0.55 M, 0.6 M, 0.65 M, 0.7 M, or about 0.75 M. In various embodiments, the concentration of the diaminotriazole precursor in the reaction mixture prior to reaction with the phenyl carbamate is about 0.25 M to 0.75 M, 0.35 M to about 0.7 M, or 0.4 M to about 0.6 M.

In several cases preparation of the carbamates also proved challenging. For 12, the original plan to prepare the 2-aryloxazole 17c was to utilize regioselective, palladium-catalyzed direct arylation of the commercially available ethyl oxazole-4-carboxylate with unprotected 4-iodo aniline, under previously described conditions. However, these conditions (5 mol % Pd(OAc)$_2$, 10 mol % JohnPhos) proved inefficient, affording the desired product in single-digit yields. Consequently, it was decided to protect the aniline and repeat the arylation with increased catalyst and ligand loading (10 mol % Pd(OAc)$_2$, 20 mol % JohnPhos). This approach allowed access to 17c' in a viable yield (30%). And, finally, hydrolysis of the ester in the last step required care. Standard conditions using strong, nucleophilic bases led to decomposition of the urea. Fortunately, heteroatoms were present in the α or β-position of most ester precursors, which allowed use of the mild ester hydrolysis method introduced by Mattsson et al. In this transformation, lithium coordination to the carbonyl group and the neighboring heteroatom increases the electrophilicity and thus selectivity of the ester toward nucleophilic attack, allowing hydrolysis by water at room temperature. However, long reaction times were required due to the low solubility of the compounds in the reaction media.

In the compound of Formula I,

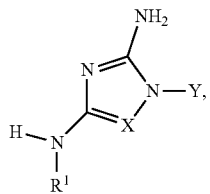

Formula I wherein,
Y is selected from the group consisting of —CH$_2$—R$^2$, —C(=O)NR$^2$R$^3$, optionally substituted C$_{5-10}$ heteroaryl, and optionally substituted C$_{5-6}$ heterocycloalkyl;
wherein the optional substitution is independently at least one substituent selected from the group consisting of C$_{1-5}$ alkyl, C$_{1-5}$ alkoxy, C$_{1-5}$ thioalkyl, C$_{1-5}$ aminoalkyl, C$_{5-10}$ aryl, C$_{5-10}$ heteroaryl, =O (oxo), F, Cl, Br, I, C(=O)OR, NHC(=O)R, and OH;
R$^1$ and R$^2$ are each independently selected from the group consisting of C$_{2-6}$ alkenyl, C$_{3-7}$ cycloalkyl, C$_{6-10}$ aryl, 5-10 membered heteroaryl, 4-10 membered heterocycloalkyl, C$_{6-10}$-5-6 membered heterobiaryl, 5-6 membered-C$_{6-10}$ heterobiaryl, and C$_{6-10}$—C$_{6-10}$ biaryl,
each independently optionally substituted by at least one substituent selected from the group consisting of F, Cl, Br, I, OR, OC(=O)N(R)$_2$, CN, NO$_2$, CF$_3$, OCF$_3$, R, N(R)$_2$, SR, SOR, SO$_2$R, SO$_2$N(R)$_2$, SO$_3$R, C(=O)R, C(=O)OR, OC(=O)R, O(CH$_2$)$_{0-2}$C(=O)OR, C(=O)N(R)$_2$, OC(=O)N(R)$_2$, (CH$_2$)$_{0-2}$N(R)C(=O)R, N(R)SO$_2$R, N(R)C(=O)OR, N(R)C(=O)R, N(R)C(=O)N(R)$_2$, and C(=NH)N(R)$_2$,
wherein each occurrence of R is independently selected from the group consisting of hydrogen and (C$_1$-C$_6$) hydrocarbyl; or wherein two R groups bonded to a nitrogen atom or to adjacent nitrogen atoms can together with the nitrogen atom or atoms form a heterocyclyl;
R$^3$ is H or C$_{1-4}$ hydrocarbyl;
X is N or C—R$^4$, wherein R$^4$ is H or C$_{1-4}$ hydrocarbyl optionally substituted by 1 to 3 substituents selected from the group consisting of OR', NHR', and NR'$_2$,
wherein each occurrence of R' is independently selected from the group consisting of hydrogen and (C$_1$-C$_6$)hydrocarbyl; or wherein two R' groups bonded to a nitrogen atom or to adjacent nitrogen atoms can together with the nitrogen atom or atoms form a heterocyclyl.

In various embodiments, R$^1$ is C$_{6-10}$ aryl. In various embodiments, Y is —C(=O)NR$^2$R$^3$.

In some embodiments, R$^2$ is C$_{6-10}$ aryl, 5-10 membered heteroaryl, C$_{6-10}$-5-6 membered heterobiaryl, 5-6 membered-C$_{6-10}$ heterobiaryl, or C$_{6-10}$—C$_{6-10}$ biaryl.

In various embodiments, X is N. In some embodiments, R$^3$ is H.

In various embodiments, R$^1$ has the structure:

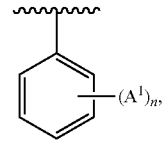

each occurrence of A$^1$ is independently selected from the group consisting of F, Cl, Br, I, OR, OC(=O)N(R)$_2$, CN, NO$_2$, CF$_3$, OCF$_3$, R, N(R)$_2$, SR, SOR, SO$_2$R, SO$_2$N(R)$_2$, SO$_3$R, C(=O)R, C(=O)OR, OC(=O)R, O(CH$_2$)$_{0-2}$C(=O)OR, C(=O)N(R)$_2$, OC(=O)N(R)$_2$, (CH$_2$)$_{0-2}$N(R)C(=O)R, N(R)SO$_2$R, N(R)C(=O)OR, N(R)C(=O)R, N(R)C(=O)N(R)$_2$, and C(=NH)N(R)$_2$, wherein each occurrence of R is independently selected from the group consisting of hydrogen and (C$_1$-C$_6$)hydrocarbyl; or wherein two R groups bonded to a nitrogen atom or to adjacent nitrogen atoms can together with the nitrogen atom or atoms form a heterocyclyl; and n is an integer from 0 to 5.

The compound can be a compound of Formula Ia:

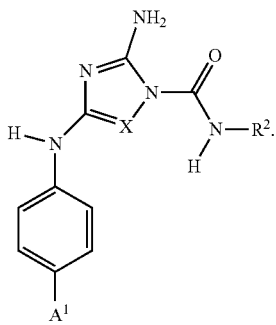

Formula Ia

In certain embodiments, $A^1$ is $SO_2NH_2$. In other embodiments, $A^1$ is CN. In some emobdiments, $A^1$ is CN, $OCF_3$, $SO_2NH_2$ or $C(=O)NHCH_3$. In some embodiments, $A^1$ is $C(=O)$— morpholynyl, where the morpholine group is bonded to the carbonyl through the morpholine nitrogen atom.

In some embodiments, $R^2$ has the structure

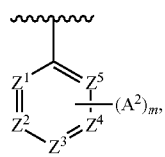

wherein
each of $Z^1$-$Z^5$ is independently $CA^2$ or N, wherein zero, one, or two of $Z^1$-$Z^5$ are N;
each occurrence of $A^2$ is independently selected from the group consisting of

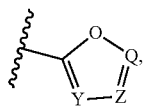

F, Cl, Br, I, OR, $OC(=O)N(R)_2$, CN, $NO_2$, $CF_3$, $OCF_3$, R, $N(R)_2$, SR, SOR, $SO_2R$, $SO_2N(R)_2$, $SO_3R$, $C(=O)R$, $C(=O)OR$, $OC(=O)R$, $C_{2-6}$ alkenyl-COOR, $C_{2-6}$ alkenyl-$CONR_2$, $O(CH_2)_{0-2}C(=O)OR$, $C(=O)N(R)_2$, $OC(=O)N(R)_2$, $(CH_2)_{0-2}N(R)C(=O)R$, $N(R)SO_2R$, $N(R)C(=O)OR$, $N(R)C(=O)R$, $N(R)C(=O)N(R)_2$, and $C(=NH)N(R)_2$;
wherein zero, one, or two $A^2$ can be independently

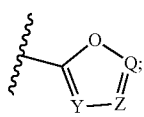

wherein Y, Z, and Q are each independently C—$R^5$ or N, wherein each $R^5$ is independently selected from the group consisting of H, F, Cl, Br, I, OR, $OC(=O)N(R)_2$, CN, $NO_2$, $CF_3$, $OCF_3$, R, $N(R)_2$, SR, SOR, $SO_2R$, $SO_2N(R)_2$, $SO_3R$, $C(=O)R$, $C(=O)OR$, $OC(=O)R$, $O(CH_2)_{0-2}C(=O)OR$, $C(=O)N(R)_2$, $OC(=O)N(R)_2$, $(CH_2)_{0-2}N(R)C(=O)R$, $N(R)SO_2R$, $N(R)C(=O)OR$, $N(R)C(=O)R$, $N(R)C(=O)N(R)_2$, and $C(=NH)N(R)_2$;
wherein each occurrence of R is independently selected from the group consisting of hydrogen and $(C_1$-$C_6)$ hydrocarbyl; and m is an integer from 0 to 5.

In various embodiments, $Z^1$ is N and $Z^2$-$Z^5$ are CH. In some embodiments, $Z^2$ is N and $Z^1$ and $Z^3$-$Z^5$ are CH. In various embodiments, m is 1.

The compound can be a compound of Formula Ib, Formula Ic, or Formula Id:

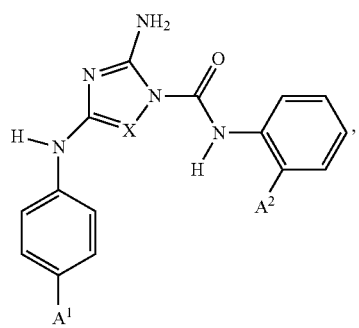

Formula Ib

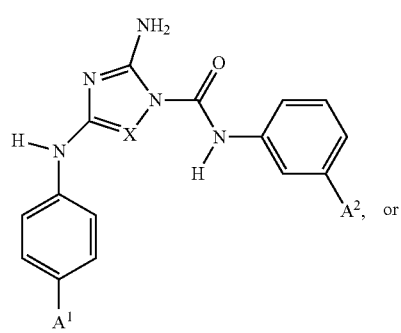

Formula Ic

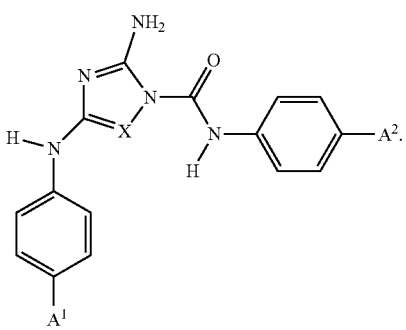

Formula Id

In various embodiments, $A^2$ is selected from the group consisting of

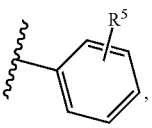 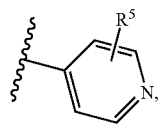 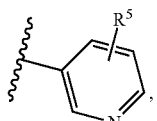

-continued
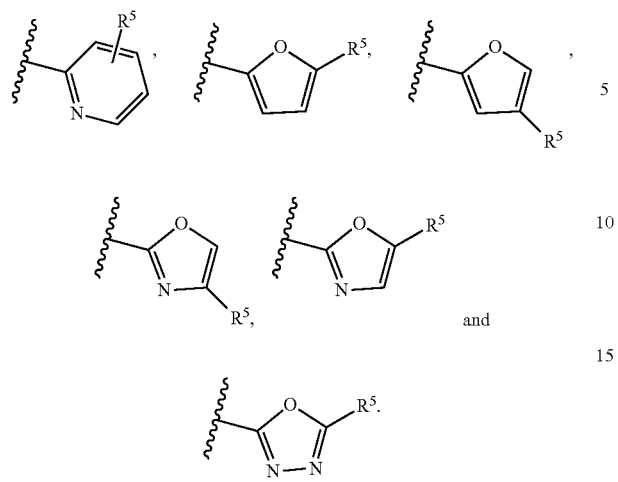
In various embodiments, $A^2$ is selected from the group cosisting of
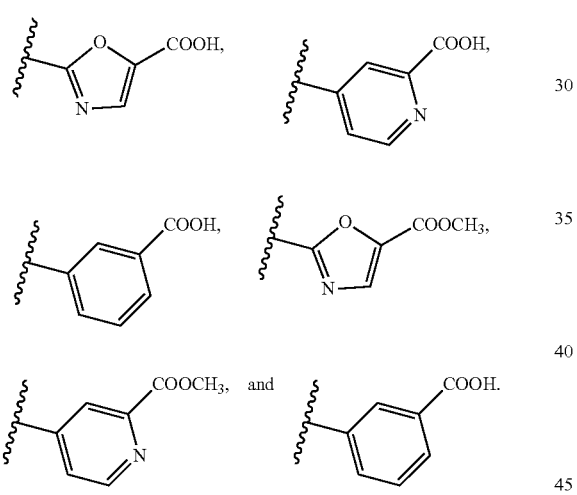
In some embodiments, $R^5$ is COOH or $COOCH_3$.
In various embodiments, the compound is selected from the group consisting of
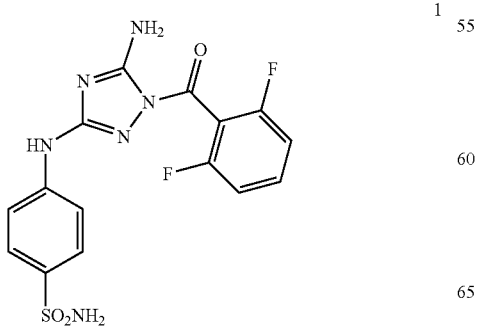
1
-continued
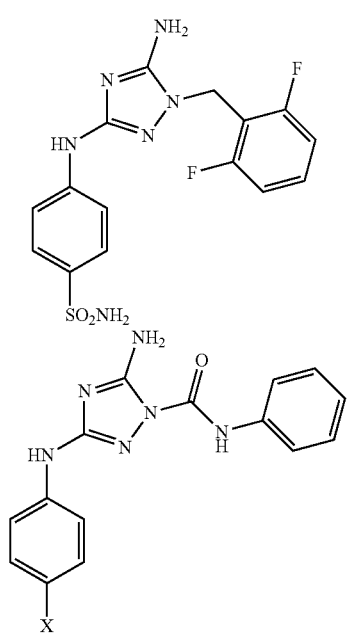
2
3 X = CN
4 X = $SO_2NH_2$
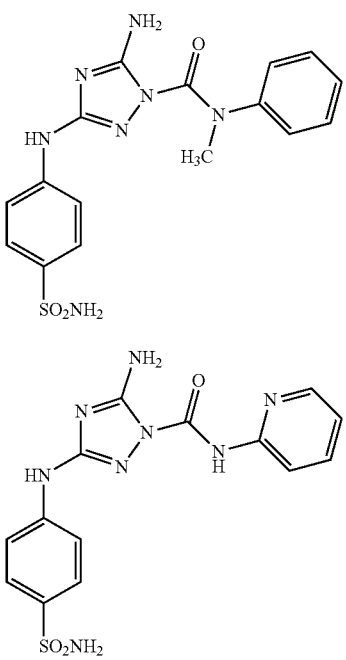
5
6
7

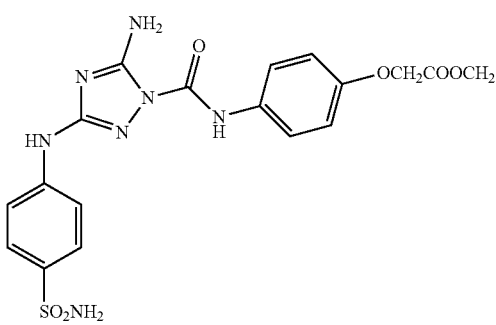
8
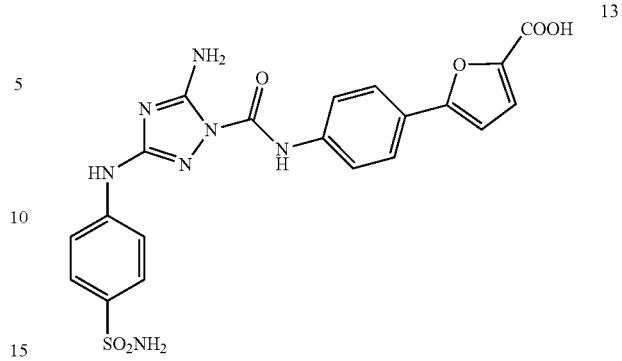
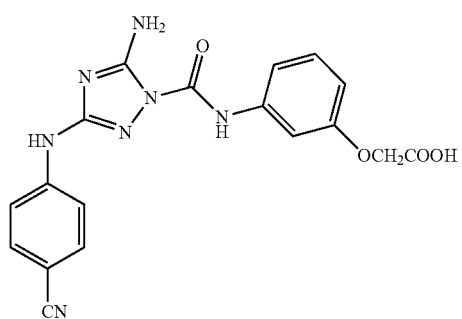
9 X = CN
10 X = SO₂NH₂
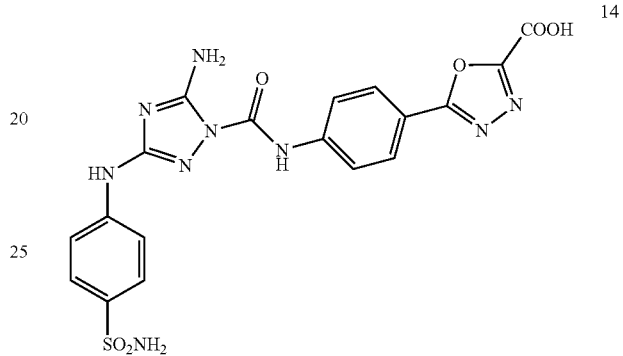
11
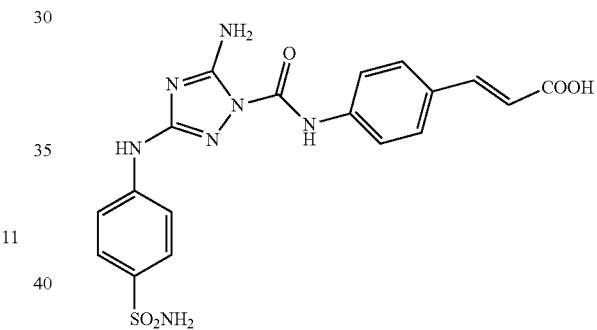
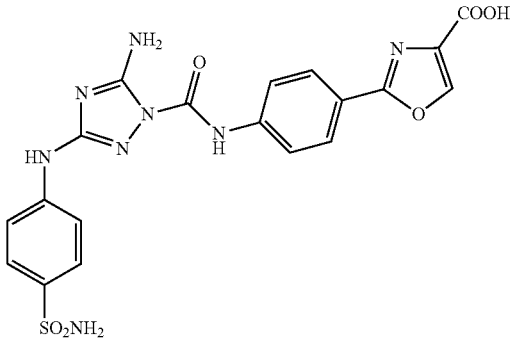
12
In Table 1, binding affinities are shown for comparative compound 1 and compounds of Formula I (2-15) as measured in a fluorescence polarization assay.
TABLE 1
| Binding Affinity for JAK2 JH2 ($K_d$, μM) from the FP Assay | |
|---|---|
| Cmpd | $K_d$ (μM)[a] |
| 1 | 0.456 ± 0.124 |
| 2 | 16.7 ± 5.4 |
| 4 | 4.7 ± 0.8 |
| 5 | 47.8 ± 9.2 |
| 6 | 30.5 ± 3.6 |
| 7 | 12.3 ± 0.6 |
| 8 | 1.9 ± 0.1 |
| 9 | 0.643 ± 0.019 |
| 10 | 0.571 ± 0.034 |
| 11 | 4.0 ± 0.3 |
| 12 | 0.346 ± 0.034 |
| 13 | 0.439 ± 0.064 |
| 14 | 7.0 ± 0.1 |
| 15 | 0.374 ± 0.013 |
[a]$K_d$ data from quadruplicate measurements in three independent assays. Mean ± SEM.

A method of making a compound of Formula I includes reacting a compound having the structure:

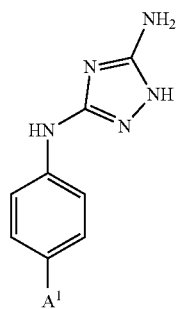

with a compound having the structure:

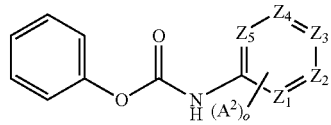

in a solvent to form a compound of Formula I, wherein $A^1$, $A^2$, and $Z_1$-$Z_5$ are as defined herein. In various embodiments, the solvent comprises dioxane. In some embodiments, the reacting is at a temperature of about 95° C. to about 115° C.

In some embodiments, the concentration of

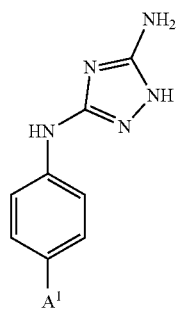

in the solvent is about 0.35 M to about 0.7 M.

Compounds of Formula I are, in various embodiments, selective inhibitors of the JAK2 JH2 domain. JAK1, JAK2, JAK3, and TYK2 are members of the Janus family of non-receptor tyrosine kinases, which are activated by and mediate the cellular responses induced by binding of a variety of cytokines to specific cytokine receptors. Cytokine-induced activation of the JAK-STAT signaling pathway and other intracellular pathways play important roles in the control of cell proliferation, hematopoiesis, and immune functions. In addition to a canonical tyrosine kinase domain (JH1) located in the N-terminal region, JAK proteins contain a pseudokinase domain designated JH2. Though JH2 domains have an ATP-binding site, they show little or no catalytic activity. However, JH2 domains do have a regulatory function for the JH1 kinase activity such that mutations in JH2 can cause hyperactivation leading to numerous diseases and cancer. In particular, the single point-mutation Val617Phe (V617F) in JAK2 JH2 is responsible for the majority of myeloproliferative disorders including polycythemia vera, myelofibrosis, and essential thrombocythemia. Though undesirable side effects such as anemia may occur upon inhibition of JAK2 JH1 kinase activity, mutagenesis studies have raised the possibility of selective reversal of the activating effect of V617F by displacement of ATP from JAK2 JH2.

In certain non-limiting embodiments of the invention, the compounds contemplated herein bind to the JAK2 JH2 ATP binding site with selectivity over the corresponding JAK2 JH1 ATP binding site. In certain embodiments, the compounds contemplated herein selectively reverse the activating effect of the V617F mutation in JAK2 JH2.

Figure 1B:
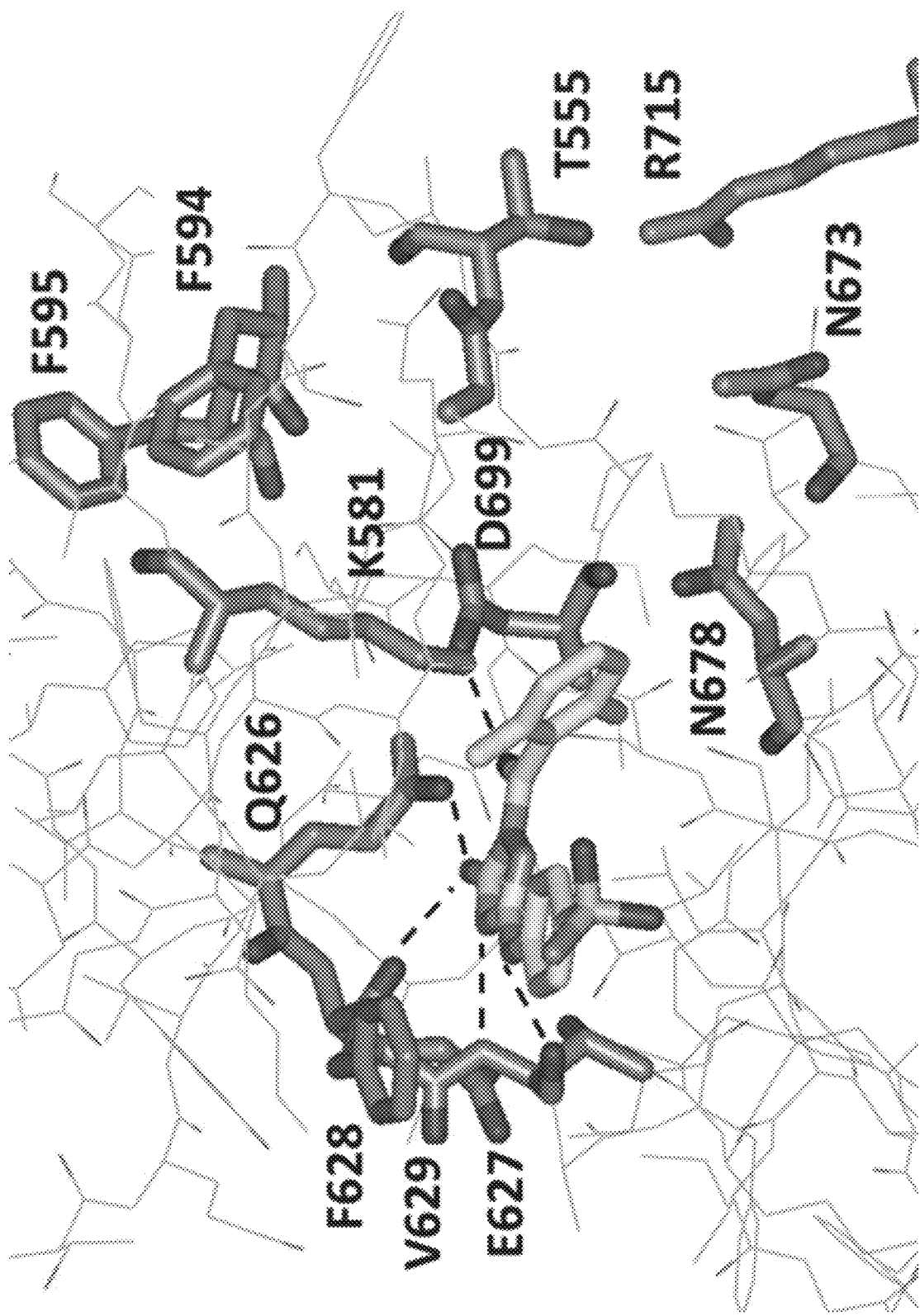

JNJ7706621 (1) is a known pan-CDK and pan-JAK inhibitor. Analysis by isothermal titration calorimetry (ITC) yielded binding constants $K_d$ of 106 nM and 31 nM with JAK2 JH2 and JH1, respectively, showing a greater than three-fold preference for binding JH1. These values are lower than an earlier $K_d$ report of 220 nM for 1 with a JH1-JH2 construct of JAK2 in a competition binding assay. Crystal structures for 1 with JAK2 JH2 and JH1 were also determined, as illustrated in FIGS. 1A-1B. The binding sites are similar in the hinge regions, Glu627-Phe628-Val629 for JH2, and Glu930-Tyr931-Leu932 for JH1; the diaminotriazole fragment of 1 engages in three hydrogen bonds with the backbone in both cases. In addition, for JAK2 JH2 there are hydrogen bonds between the amino group of 1 and the sidechain oxygen of the gatekeeper, Gln626, and between the carbonyl group of 1 and Lys581. The strong binding of 1 to both JAK2 JH1 and JH2 is consistent with the similar binding modes in the hinge regions and the limited contact of the difluorophenyl substituent. The molecule is U-shaped with the aryl group directed out of the binding site towards the solvent.

Figure 2:
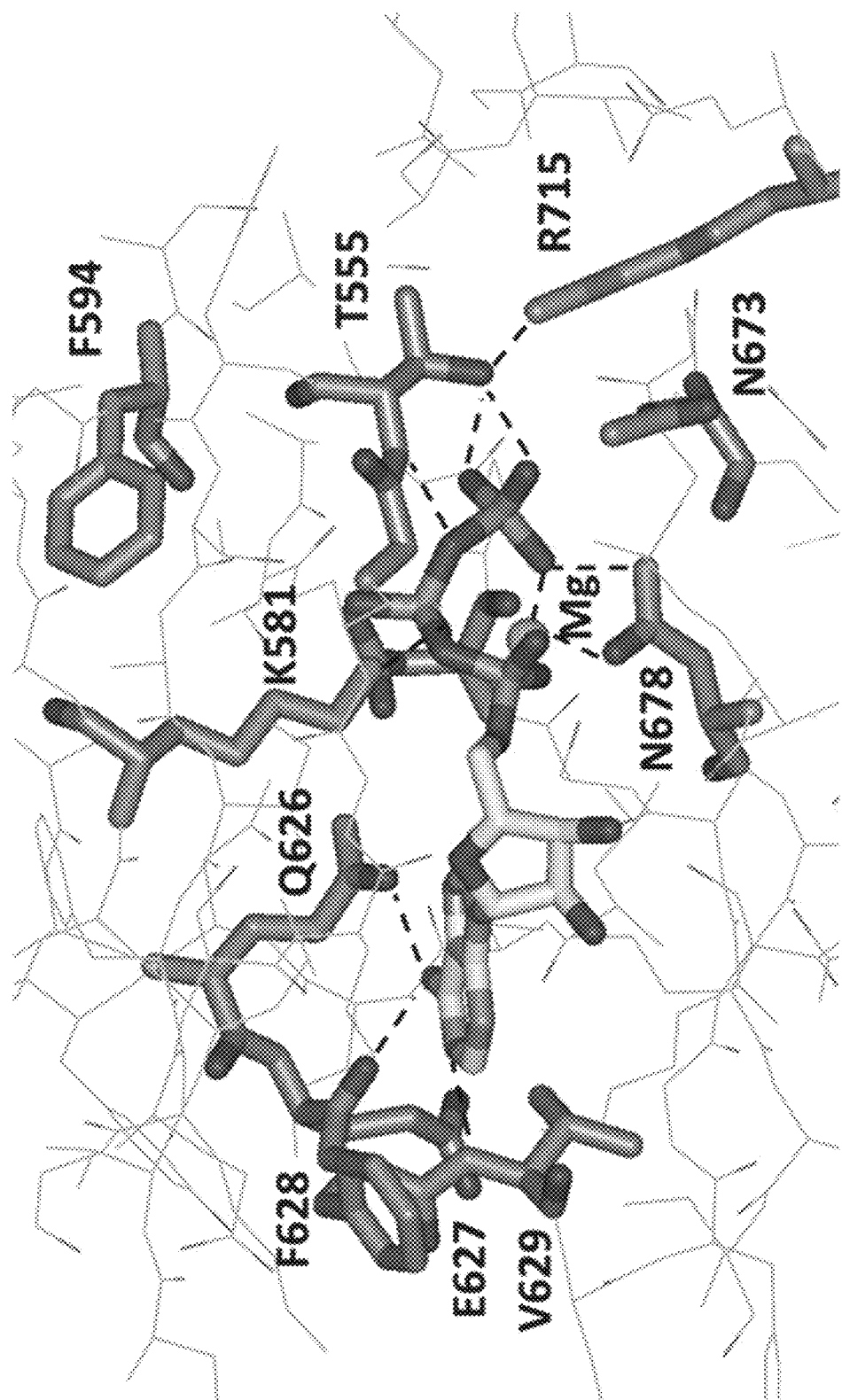
FIG. 2 shows a rendering from the crystal structure for ATP bound to JAK2 JH2 (PDB ID 4FVQ).

In order to seek molecules that may selectively bind to the ATP site in JAK2 JH2 and avoid inhibition of the kinase activity of wildtype (WT) JAK2, the compounds of Formula I were identified. In various embodiments, the compounds of Formula I have at least, or greater than about a 2, 3, 4, 5, 6, 7, 8, 9, 10, 15, 20, 25, 30, 35, 40, 45, 50, 75, 100, or 250-fold selectivity for JAK JH2 compared to JAK JH1. In viewing FIGS. 1A-1B, it is apparent that the desired selectivity needs to exploit differences in the eastern part of the binding clefts heading towards Thr555 and Arg715 in JAK2 JH2. However, this is the region where the triphosphate portion of ATP is bound with the terminal phosphate group in a hydrogen-bond cluster with Thr555, Asn678, and Arg715, as shown in FIG. 2. Thus, it is a very polar region with the concomitant targeting difficulties owing to the competition between an envisioned polar substituent being well-solvated in water and in the polar binding site. Nevertheless, the challenge was taken on with the notion that precise fit of a relatively rigid, polar substituent ending in an anionic mimic of the terminal phosphate might be successful. Competition with ATP is not expected to be problematic since its binding is relatively weak with binding constants of 1.3 μM for both WT JAK2 JH2 and the V617F mutant. It should also be noted that the principal structural changes for JAK2 V617F occur in this vicinity. Val617 is located just above Phe595 in FIGS. 1A-1B and upon mutation, Phe617-Phe595-Phe594 form an edge-face-edge stack with downward displacement of Phe594 towards the terminal phosphate in the ATP-bound structures. Phe595 has been shown to be important for the constitutive activity of JAK2 V617F; mutation to non-aromatic residues significantly decreases the activity.

Lead Optimization

An initial question that was addressed was the importance of the carbonyl group in 1 for binding to JAK2 JH2. Though the carbonyl oxygen atom participates in a hydrogen bond with the ammonium group of Lys581 ($r_{NO}$=3.16 Å), it is in repulsive contact, 3.06 Å, with the sidechain carbonyl oxygen atom of Gln626 (FIGS. 1A-1B). Thus, 2, the desoxy analog of 1, was prepared; it was found to yield a much reduced affinity for JAK2 JH2 with a $K_d$ of 16.7 µM in the FP assay (Table 1). Apparently, the hydrogen bond with the charged ammonium group more than offsets the repulsion with Gln626 and/or the reduced torsional flexibility of 1 compared to 2 is beneficial.

Figure 3:
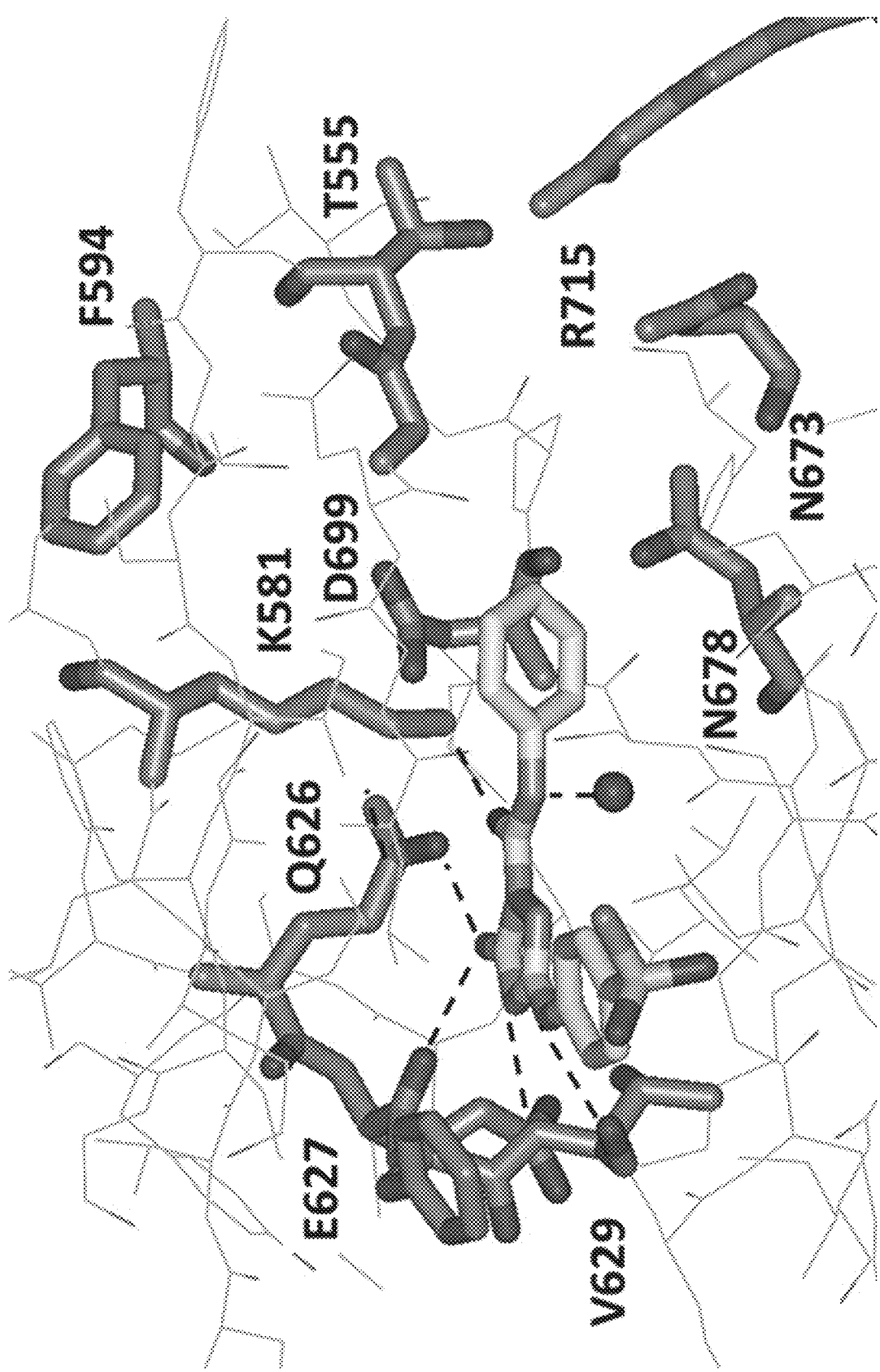
FIG. 3 shows a rendering from the 1.90-Å crystal structure for 4 bound to JAK2 JH2 (PDB ID 6OBB).

Having established the benefit of the carbonyl group, the next step was to append a substituent that should project eastwardly past Lys581 towards Thr555 rather than outward from the binding site as for 1. Though several alternatives were considered, a secondary amide linkage modeled well, especially with an N-phenyl substituent that might form a cation-π interaction with Lys581. This notion led to the synthesis of 3 and 4, which only differ by the p-anilinyl substituent being cyano or sulfamyl. In general, little difference was observed in binding affinity for these alternatives, but greater solubility for the sulfonamides. The FP result for the N-phenylamide 4 with a 3-fold improvement over 2 to 4.7 µM was encouraging in view of the fact that the phenyl ring is being placed in a polar environment. It was also possible to obtain crystal structures for the complexes of both 3 and 4 with JAK2 JH2 at 1.94-Å and 1.90-Å resolution, respectively. The structures clearly reveal the desired eastwardly projection and the cation-π interaction with Lys581, as illustrated in FIG. 3 for 4. The hydrogen-bond length between the amide carbonyl oxygen of 4 and the ammonium nitrogen atom of Lys581 is 2.85 Å, and the distances between the ammonium nitrogen and the carbon atoms of the phenyl ring are as short as 3.92 Å for the ipso carbon atom and 3.77 Å for the nearer ortho carbon atom, while the hydrogen bonding in the hinge region is essentially the same for 1, 3 and 4.

To expand the structure-activity data, 5, the tertiary methylamide corresponding to 4 was checked. Since there is a water molecule hydrogen-bonded to the amide NH in 4 ($r_{NO}$=3.11 Å, FIG. 3), it might seem likely that 4 and 5 would have similar $K_d$ values. However, a conformational issue should be noted for acetanilides. Though acetanilide prefers the Z-conformer, N-methylacetanilide prefers the E-conformer. This preference was confirmed with DFT B3LYP/6-31G(d) geometry optimizations and subsequent single-point energy evaluations at the MP2/6-311+G(d,p) level. The B3LYP and MP2 calculations favor the Z-conformer for acetanilide by 3.19 and 1.29 kcal/mol, respectively, while the E-conformer is preferred by 3.87 and 3.39 kcal/mol for N-methylacetanilide (Scheme 2). Assuming this preference carries over to 4 and 5, there would be a significant conformational penalty for 5 to achieve the Z-conformation that is needed for the cation-π interaction with Lys581. As listed in Table 2, FEP calculations were also performed for the conversion of Z-5 to Z-4; when adjusted for the conformational penalty, weaker binding is expected for 5. This was borne out by the measured $K_d$ of 47.8 µM for 5 in Table 1.

Scheme 2. Computed Conformational Preferences (kcal/mol) for Acetanilides

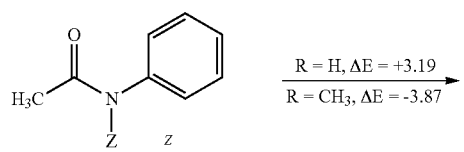

R = H, ΔE = +3.19
R = CH₃, ΔE = −3.87

-continued

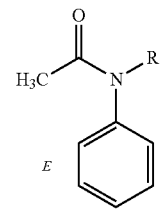

TABLE 2

Differences in Free Energies of Binding with JAK2 JH2 from FEP Calculations

| A → B | Transformation | $\Delta G_b$ (kcal/mol)[a] |
|---|---|---|
| 5 → 4 | (Z)—O=CNMePh → O=CNHPh | 1.47 ± 0.54 |
| 6 → 4 | 2-pyridinyl → phenyl | −0.43 ± 0.59 |
| 7 → 4 | 3-pyridinyl → phenyl | −1.44 ± 0.45 |
| 4-Pyr[b] → 4 | 4-pyridinyl → phenyl | −0.64 ± 0.16 |

[a] [a]4-pyridinyl analogue of 6 or 7.

Pyridinyl replacements 6 and 7 for the phenyl group were also considered. Initial structure building with BOMB indicated that constructive interaction of the pyridinyl nitrogen atoms with Lys581 might be possible with N—N contacts of 3.32 Å for 6 (FIG. 4) and 3.72 Å for 7. Energy minimizations with the force-field find a more favorable interaction with the protein by 3.0 kcal/mol for 6 than 7; however, this is offset by a 3.4 kcal/mol conformational penalty for placement of the pyridine nitrogen atom syn rather than anti to the carbonyl oxygen in 6, which is needed for the hydrogen bond with Lys581. B3LYP/6-31G(d) optimizations for the corresponding syn and anti conformers of N-(pyridine-2-yl) acetamide indicate an even higher conformational penalty to achieve the syn conformer of 6, 8.98 kcal/mol.

Figure 4:
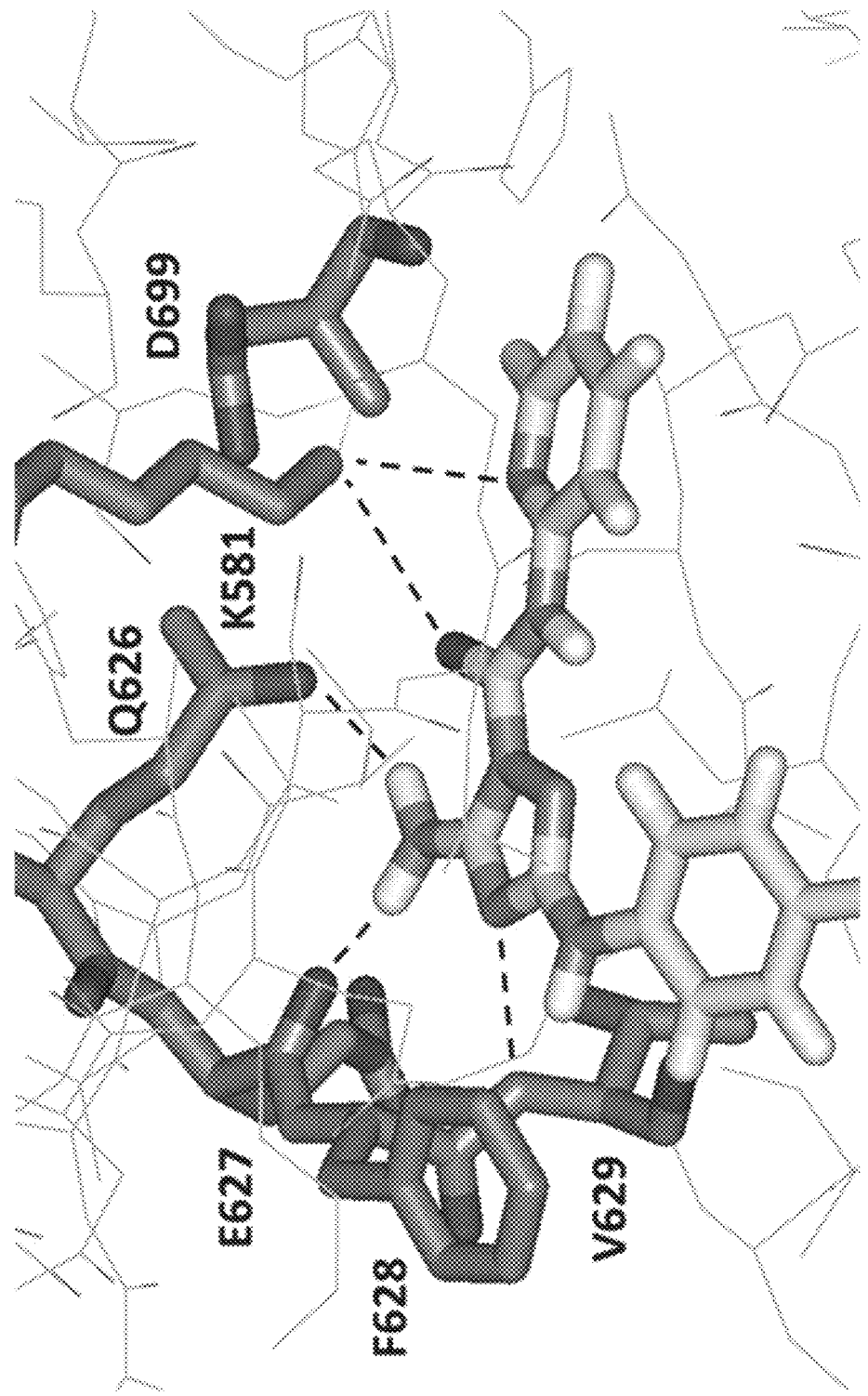
FIG. 4 shows a modeled structure illustrating the potential hydrogen bonding between Lys581 and the amide carbonyl oxygen atom and the pyridinyl nitrogen atom for 2-pyridinyl analogues of 3 and 4 such as 6.

For both 6 and 7, the azine ring is now basically in-plane with the amide group, which replaces the cation-π interaction found for 4 with Lys581 (FIG. 3) with a hydrogen bond (FIG. 4). Results of FEP calculations were also obtained for conversion of 6 and 7 to 4 with the predictions that the pyridinyl analogs would be weaker binders for JAK2 JH2 (Table 2). The FEP calculations for 6 considered multiple starting conformers; both conformers with the pyridine nitrogen syn or anti to the carbonyl group were stable and the results indicated that the syn conformer is favored by 0.7±0.2 kcal/mol. The compounds were synthesized and the $K_d$ results of 30.5 (6) and 12.3 (7) µM confirmed the weaker binding than for 4 (Table 1). These relatively simple changes illustrate well the complexities in making even qualitatively correct predictions for differences in protein-ligand binding owing to the complexities of the inter- and intra-molecular energetics and solvation.

The next step in the design was to consider substituents in the para position of the phenyl ring of 4 that would extend further towards Thr555 and Arg715 (FIG. 3). In view of the placement of the terminal phosphate of ATP in this region (FIG. 2), substituents terminating in an anionic group seemed desirable. Modeling was performed for various carboxyalkyl and carboxyalkoxy alternatives with the conclusion that carboxymethoxy should be particularly promising; the OCH₂ fragment should be in-plane with the phenyl ring, as in anisole, and the carboxylate group should be extended to form hydrogen bonds with Thr555. For comparison, both carboxyethyl and carboxyethoxy were expected to incorporate a gauche dihedral angle and be less extended. Thus, the carboxymethoxy analogues 9 and 10 were synthesized and assayed along with 8, the methyl-ester precursor of 10.

The results were gratifying with a ca. 8-fold boost in binding strength with JAK2 JH2 for 9 (0.64 μM) and 10 (0.57 μM) compared to 4. The corresponding result for the ester 8 (1.9 μM) confirmed the importance of an anionic terminus for the substituent, though it is not obvious intrinsically that a carboxylate group would yield any improvement in binding since it would be well hydrated unbound in water. 11, the meta-substituted isomer of 9 was also synthesized and showed reduced binding with a $K_d$ of 4.0 μM (Table 1). The modeling in this case predicted that the substituent would likely be directed into the solvent from the upper meta position in FIG. 3.

Figure 5:
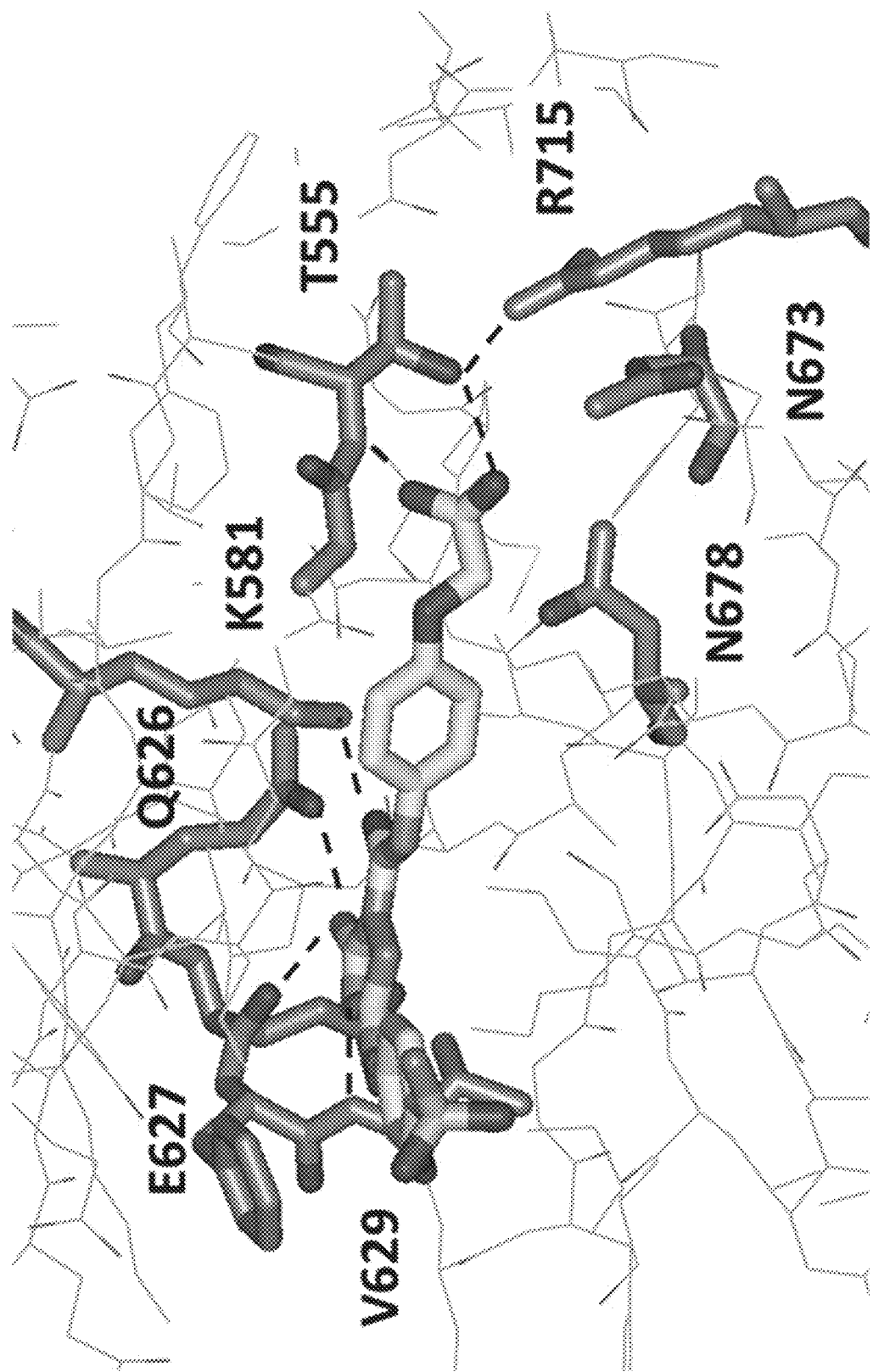
FIG. 5 shows a rendering from the 1.71-Å crystal structure for 10 bound to JAK2 JH2 (PDB ID 6OBF).

Crystal structures were obtained for the complexes of 9 and 10 with JAK2 JH2 at resolutions of 2.06 Å and 1.71 Å, respectively. As shown in FIG. 5, the carboxylate group of 10 is extended, as expected, with a COCC dihedral angle of 170°. It is positioned similarly to the terminal phosphate group of ATP in FIG. 2, and it forms hydrogen bonds with the backbone NH and side-chain OH of Thr555 with lengths of 3.06 and 2.83 Å. As expanded upon in FIG. 6, the carboxylate group also participates in an extensive network of hydrogen bonds with localized water molecules in the crystal structure including three hydrogen bonds between the carboxylate oxygen atoms and water molecules.

Figure 6:
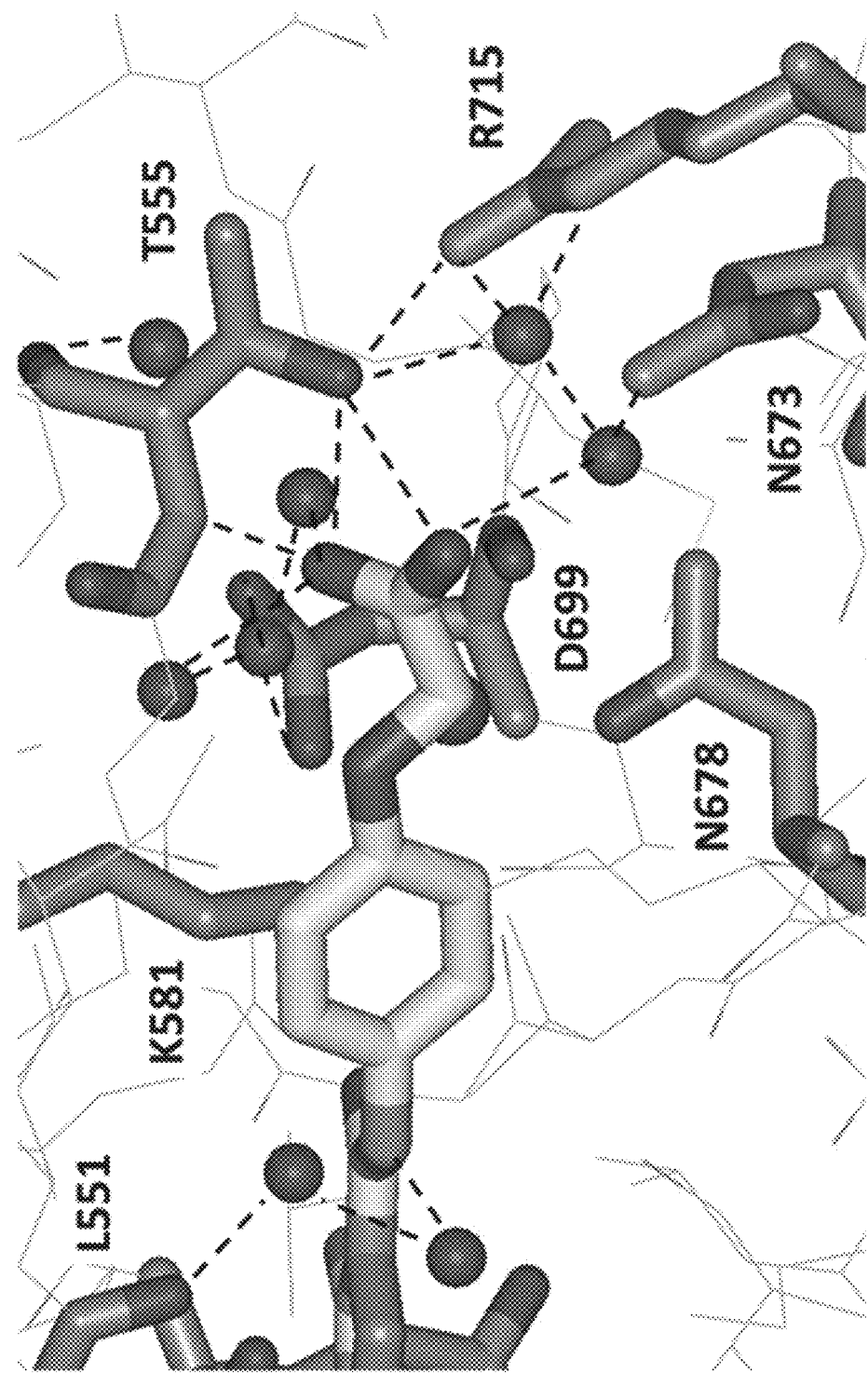
FIG. 6 shows an illustration of the hydrogen-bonding in the vicinity of the carboxylate group of 10 from the 1.71-Å crystal structure with JAK2 JH2 (PDB ID 6OBF). Red spheres represent oxygen atoms of localized water molecules.

In viewing the crystal structure for 10, it was felt that a 1-Å additional extension of the carboxylate group towards Arg715 to form a salt bridge would likely be beneficial for both binding and selectivity. Addition of a methylene group was not expected to be optimal based on the modeling noted above. Instead, replacement of the methoxy linking group with a five-membered heterocycle yielded computed structures that delivered the desired contact. The added rigidity of the heterocycle was also viewed as a desirable feature, though there were concerns about unfavorable disruption of the hydrogen-bonding networks (FIG. 6). More than 30 alternative structures were built with BOMB and visually inspected; our preference was for heterocycles with multiple hydrogen-bonding sites.

Figure 7:
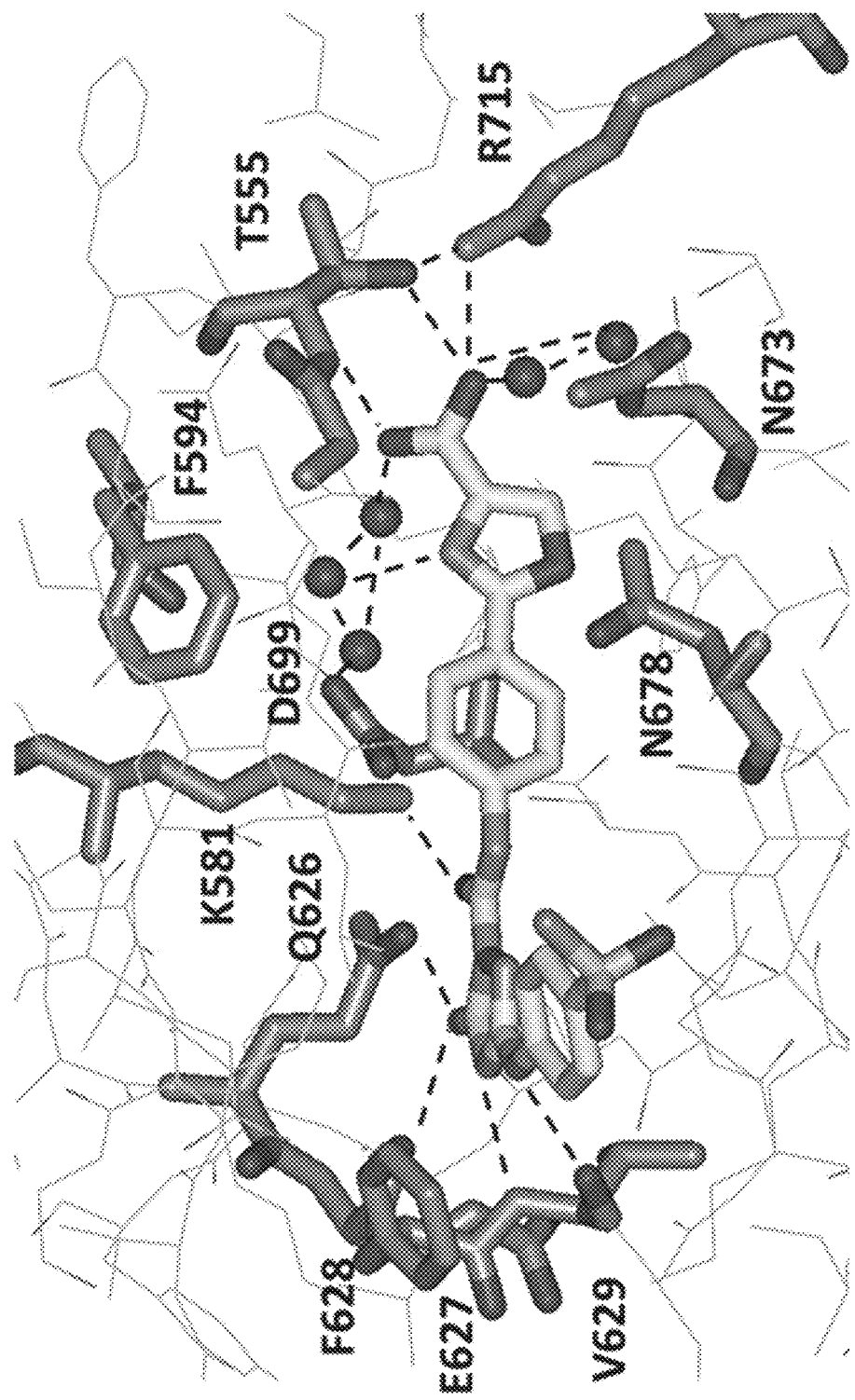
FIG. 7 shows a rendering from the 2.03-Å crystal structure for 12 bound to JAK2 JH2 (PDB ID 6OCC). Red spheres represent oxygen atoms of localized water molecules.

The syntheses brought new challenges; however, several illustrative compounds were prepared starting with the oxazole-4-carboxylic acid 12 (Scheme 1). The FP assay result of 0.346 ±0.03 μM showed the validity of the design and yielded the first compound that is a clearly stronger binder for JAK2 JH2 than JNJ7706621 (1). A crystal structure for this complex at a resolution of 2.03 Å (FIG. 7). The shortened contact with Arg715 was achieved with an O . . . N distance of 3.56 Å, while maintaining the hydrogen bonds with the NH (2.98 Å) and side-chain OH (2.70 and 3.58 Å) of Thr555. There are again three water molecules hydrogen-bonded to the carboxylate group with O . . . O separations of 2.28, 2.82, and 3.09 Å. The water molecule with the 2.28-Å contact is part of a striking triangle of hydrogen-bonded water molecules that bridges between the carboxylate groups of the ligand and Asp699. The central water molecule in the cluster is also hydrogen-bonded to the nitrogen atom of the oxazole at a distance of 2.79 Å. Furthermore, the cluster is in van der Waals contact with a meta carbon atom of Phe594 with separations of 3.37, 3.91, and 4.27 Å. Thus, this interesting water trimer is providing a carefully arranged molecular cushion between the ligand and JAK2 JH2 residues Asp699 and Phe594.

Among additional five-membered heterocycles as linking groups, the furan (13) and 1,3,4-oxadiazole (14) analogues of 12 were synthesized. These were expected to be less robust binders for JAK2 JH2 than the oxazole 12. First, furan-type oxygen atoms are weak hydrogen-bond acceptors and their replacement of the oxazole nitrogen atom in FIG. 7 would weaken the link to the water cluster. Furthermore, furan and thiophene are the most lipophilic five-membered heteroaromatic molecules with octanol/water log P values of 1.34 and 1.81 versus, for example, 0.12 for oxazole, 0.08 for isoxazole, and 0.44 for thiazole. Finally, the oxazole oxygen atom in the crystal structure for 12 (FIG. 7) does not participate in a hydrogen bond and, in fact, there is no room for a neighboring water molecule. Thus, if the oxadiazole ring in 14 is oriented as for 12 in FIG. 7, there would be a significant penalty for desolvation of one of the nitrogen atoms. The qualitative expectations were borne out by the measured $K_d$ values of 0.44 and 7.0 μM for 13 and 14 (Table 1).

From viewing the crystal structure for 10 (FIG. 6) and modeling with BOMB, the (E)-cinnamic acid analog 15 was also readily suggested with the vinyl group replacing the $OCH_2$ linker. This compound was synthesized and turned out to be a somewhat better binder than 10 with a $K_d$ of 0.37 μM. The improvement can be attributed to the greater rigidity of 15 stemming from removal of one torsional degree of freedom.

JH2/JH1 Selectivity

The selectivity of reference compound 1 and the potent new compounds 10 and 12 towards wild-type JAK2 JH1 and JH2, as well as the V617F JH2 variant, were studied. $K_d$ results were obtained in all cases via fluorescence polarization using the same tracer. As listed in Table 3, the pan-JAK inhibitor JNJ7706621 (1) shows no significant selectivity in the FP assays towards the three proteins, which is in accord with prior reports and expectations from the crystallography (FIGS. 1A-1B). However, as designed, compound 10 exhibits strong (ca. 75-fold) selectivity for binding the wild-type or V617F JH2 pseudokinase domain over the JH1 kinase domain. For the oxazole 12 there is also a 19-fold preference for binding wild-type JH2 over the kinase domain, and there is again little difference in binding for wild-type JH2 and the V617F variant.

In addition, several $K_d$ values were determined using microscale thermophoresis. Optimization of this assay was possible for the wild-type JH2 and JH2 V617F domains, but an adequate signal-to-noise ratio could not be obtained for JH1. MST was found to give close but mostly lower $K_d$ values than FP (Table 3); some differences could be expected in view of the variations in optimized buffer compositions. With MST, compounds 10 and 12 are found to have identical $K_d$ values within the error limits for JAK2 JH2 near 0.30 μM, which improves on the 0.49 μM result for 1. The binding constants for JAK2 JH2 and the V617F variant are again close. Finally, compound 15 is found with MST to be the most tenacious binder with $K_d$ values at the 200-nM level for both the JH2 and V617F JH2 domains.

TABLE 3

Binding Affinities ($K_d$, µM) from the FP and MST Assays for JAK2 Domains

| Cmpd | JH1 FP | JH2 FP | JH2 MST | V617F JH2 FP | V617F JH2 MST |
|---|---|---|---|---|---|
| 1  | 0.67 ± 0.18 | 0.46 ± 0.12 | 0.49 ± 0.08 | 0.60 ± 0.09 | 0.82 ± 0.12 |
| 10 | 42.3 ± 2.3  | 0.57 ± 0.03 | 0.31 ± 0.03 | 0.54 ± 0.13 | 0.40 ± 0.05 |
| 12 | 6.6 ± 0.9   | 0.35 ± 0.03 | 0.29 ± 0.07 | 0.48 ± 0.14 | 0.43 ± 0.03 |
| 15 | 6.0 ± 1.0   | 0.37 ± 0.01 | 0.20 ± 0.05 | 0.18 ± 0.08 | 0.23 ± 0.03 |

Results with Full-Length Wild-Type and V617F JAK2

The next step was to test compounds 1 and 10 for their influence on the autophosphorylation of wild-type and V617F JAK2 mutant. These compounds were chosen to contrast the non-selective JH1/JH2 binder 1 with the JH2-selective 10. The expectation was that 1 would be an inhibitor of the JH1-based kinase activity for both the WT and variant proteins, while the outcome with 10 was unclear. Though the mutational studies suggested that displacement of ATP from the JH2 domain by selective binders could deactivate V617F JAK2, the JH2 binders may also be viewed as potential ATP surrogates leading to no effect. Since activation of kinase activity with some mutations was also observed, this outcome is also possible with the present compounds.

As detailed in the Experimental Section, full-length cDNAs encoding human WT and V617F JAK2 (residues 1-1132) were amplified by PCR, cloned into an expression plasmid, and the JAK2 constructs were expressed in HEK293T cells grown at 37° C. The transfected cells were lysed and the JAK2 proteins were immunoprecipitated from the supernatant and used to measure kinase activity by treatment with [γ-$^{32}$P]ATP in the presence or absence of increasing concentrations of 1 and 10. The autophosphorylation reaction was stopped after 15 min at 30° C. and the extent of phosphorylation was gauged by autoradiography. Details of the protocols were worked out with compound 1 to establish good signal-to-noise and reproducibility in triplicate experiments.

Though 1 has previously been established to bind to the JH1 and JH2 domains of JAK2, its status as an inhibitor has not been determined until now. As shown in FIG. 11A, we do find that 1 is an inhibitor of the autophosphorylation of both WT and V617F JAK2. There are steady, dose-dependent decreases in phosphorylation in the presence of 1. It was possible to quantify the gel bands from the phosphor autoradiography to yield IC$_{50}$ values of 2.96±0.41 µM for 1 with WT JAK2 and 11.05±3.21 µM with V617F JAK2. These results seem consistent with the $K_d$ of 0.67 µM for 1 with the JH1 kinase domain of JAK2 (Table 3).

In contrast, with the JH2-selective 10 higher concentrations are needed to see clear effects (FIG. 11B). Inhibition of WT JAK2 is apparent above ca. 10 µM, and an IC$_{50}$ of 46.53±4.74 µM could be assigned. The weak inhibition of the kinase activity is consistent with the Kd of 42 µM that was found for 10 with JAK2 JH1 (Table 3). Thus, it is expected that 10 is binding to the JH2 domain at low concentrations, but it has negligible effects on the kinase kinetics until significant binding to the ATP-site in the JH1 domain sets in at concentrations above 10 For V617F JAK2, the effects of 10 are further diminished with little inhibition apparent below 25 µM, with an IC$_{50}$ in the 100-200 µM range. Although 10 is expected to be binding to the ATP-site in the pseudokinase JH2 domain at low concentrations (Table 3), it is not affecting the kinase kinetics. This result contrasts the expectations from the mutational studies,5 though it is consistent with an alternative view of JH2-selective 10 as an ATP surrogate. The present finding for the one compound 10 does not imply that all JH2-selective binders will yield qualitatively similar results. If sufficient structural variety in JH2-binders can be explored, there will be a range of structural effects on the JH2/JH1 interface that can be expected to provide alternative outcomes.

The compounds described herein can possess one or more stereocenters, and each stereocenter can exist independently in either the (R) or (S) configuration. In certain embodiments, compounds described herein are present in optically active or racemic forms. It is to be understood that the compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In certain embodiments, a mixture of one or more isomer is utilized as the therapeutic compound described herein. In other embodiments, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound(s) described herein, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In certain embodiments, the compounds described herein exist in solvated forms with pharmaceutically acceptable solvents such as water, and ethanol. In other embodiments, the compounds described herein exist in unsolvated form.

In certain embodiments, the compound(s) described herein can exist as tautomers. All tautomers are included within the scope of the compounds presented herein.

In certain embodiments, compounds described herein are prepared as prodrugs. A "prodrug" refers to an agent that is converted into the parent drug in vivo. In certain embodiments, upon in vivo administration, a prodrug is chemically converted to the biologically, pharmaceutically or therapeutically active form of the compound. In other embodiments, a prodrug is enzymatically metabolized by one or more steps or processes to the biologically, pharmaceutically or therapeutically active form of the compound.

In certain embodiments, sites on, for example, the aromatic ring portion of compound(s) described herein are susceptible to various metabolic reactions. Incorporation of appropriate substituents on the aromatic ring structures may reduce, minimize or eliminate this metabolic pathway. In certain embodiments, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In certain embodiments, isotopically-labeled compounds are useful in drug and/or substrate tissue distribution studies. In other embodiments, substitution with heavier isotopes such as deuterium affords greater metabolic stability (for example, increased in vivo half-life or reduced dosage requirements). In yet other embodiments, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser & Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry $4^{th}$ Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

In certain embodiments, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In other embodiments, each protective group is removable by a different means. Protective groups that are cleaved under totally disparate reaction conditions fulfill the requirement of differential removal.

In certain embodiments, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as t-butyl carbamate, or with carbamates that are both acid and base stable but hydrolytically removable.

In certain embodiments, carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxybenzyl, while co-existing amino groups are blocked with fluoride labile silyl carbamates.

Allyl blocking groups are useful in the presence of acid- and base-protecting groups since the former are stable and are subsequently removed by metal or pi-acid catalysts. For example, an allyl-blocked carboxylic acid is deprotected with a palladium-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups may be selected from:

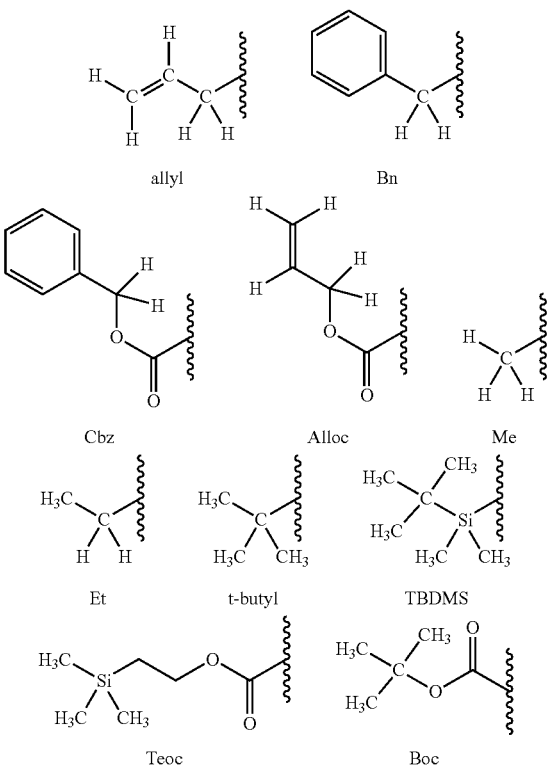

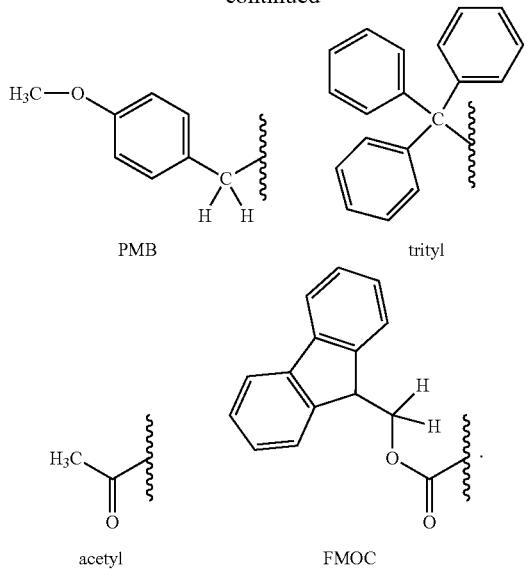

PMB    trityl acetyl    FMOC

Other protecting groups, plus a detailed description of techniques applicable to the creation of protecting groups and their removal are described in Greene & Wuts, Protective Groups in Organic Synthesis, 3rd Ed., John Wiley & Sons, New York, NY, 1999, and Kocienski, Protective Groups, Thieme Verlag, New York, NY, 1994, which are incorporated herein by reference for such disclosure.

Compositions

The compositions containing the compound(s) described herein include a pharmaceutical composition comprising at least one compound as described herein and at least one pharmaceutically acceptable carrier. In certain embodiments, the composition is formulated for an administration route such as oral or parenteral, for example, transdermal, transmucosal (e.g., sublingual, lingual, (trans)buccal, (trans) urethral, vaginal (e.g., trans- and perivaginally), (intra)nasal and (trans)rectal, intravesical, intrapulmonary, intraduodenal, intragastrical, intrathecal, subcutaneous, intramuscular, intradermal, intra-arterial, intravenous, intrabronchial, inhalation, and topical administration.

Methods of Treatment, Amelioration, and/or Prevention

The compounds of Formula I are useful for treating, ameliorating, and/or preventing myeloproliferative neoplasms (MPNs). Examples of MPNs that can be treated with the compounds of Formula I include chronic myelogenous leukemia (CML), polycythemia vera, primary myelofibrosis (also called chronic idiopathic myelofibrosis), essential thrombocythemia, chronic neutrophilic leukemia, and chronic eosinophilic leukemia.

The methods described herein include administering to the subject a therapeutically effective amount of at least one compound described herein, which is optionally formulated in a pharmaceutical composition. In various embodiments, a therapeutically effective amount of at least one compound described herein present in a pharmaceutical composition is the only therapeutically active compound in a pharmaceutical composition. In certain embodiments, the method further comprises administering to the subject an additional therapeutic agent that treats myeloproliferative neoplasms.

In certain embodiments, administering the compound(s) described herein to the subject allows for administering a lower dose of the additional therapeutic agent as compared to the dose of the additional therapeutic agent alone that is required to achieve similar results in treating a myeloproliferative neoplasm in the subject. For example, in certain embodiments, the compound(s) described herein enhance(s) the activity of the additional therapeutic compound, thereby allowing for a lower dose of the additional therapeutic compound to provide the same effect.

In certain embodiments, the compound(s) described herein and the therapeutic agent are co-administered to the subject. In other embodiments, the compound(s) described herein and the therapeutic agent are coformulated and co-administered to the subject.

In certain embodiments, the subject is a mammal. In other embodiments, the mammal is a human.

Combination Therapies

The compounds useful within the methods described herein can be used in combination with one or more additional therapeutic agents useful for treating myeloproliferative neoplasms, and/or with an additional therapeutic agents that reduce or ameliorate the symptoms and/or side-effects of therapeutic agent used in the treatment of a myeloproliferative neoplasms. These additional therapeutic agents may comprise compounds that are commercially available or synthetically accessible to those skilled in the art. When the additional therapeutic agents useful for treating myeloproliferative neoplasms are used, these additional therapeutic agents are known to treat, or reduce the symptoms of a myeloproliferative neoplasm.

In non-limiting examples, the compounds described herein can be used in combination with one or more of the following therapeutic agents useful for treating myeloproliferative neoplasms: Adriamycin PFS (Doxorubicin Hydrochloride), Adriamycin RDF (Doxorubicin Hydrochloride), Arsenic Trioxide, Azacitidine Cerubidine (Daunorubicin Hydrochloride), Clafen (Cyclophosphamide), Cyclophosphamide, Cytarabine, Cytosar-U (Cytarabine), Cytoxan (Cyclophosphamide), Dacogen (Decitabine), Dasatinib, Daunorubicin Hydrochloride, Decitabine Doxorubicin Hydrochloride, Etoposide Phosphate, Gleevec (Imatinib Mesylate), Imatinib Mesylate, Jakafi (Ruxolitinib Phosphate), Nilotinib, Rubidomycin (Daunorubicin Hydrochloride), Ruxolitinib Phosphate, Sprycel (Dasatinib), Tarabine PFS (Cytarabine), Tasigna (Nilotinib), Trisenox (Arsenic Trioxide), and Vidaza (Azacitidine).

In certain embodiments, the compounds described herein can be used in combination with radiation therapy. In other embodiments, the combination of administration of the compounds described herein and application of radiation therapy is more effective in myeloproliferative neoplasms than application of radiation therapy by itself. In yet other embodiments, the combination of administration of the compounds described herein and application of radiation therapy allows for use of lower amount of radiation therapy in treating the subject.

In various embodiments, a synergistic effect is observed when a compound as described herein is administered with one or more additional therapeutic agents or compounds. A synergistic effect may be calculated, for example, using suitable methods such as, for example, the Sigmoid-$E_{max}$ equation (Holford & Scheiner, 1981, Clin. Pharmacokinet. 6:429-453), the equation of Loewe additivity (Loewe & Muischnek, 1926, Arch. Exp. Pathol Pharmacol. 114:313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations The regimen of administration may affect what constitutes an effective amount. The therapeutic formulations may be administered to the subject either prior to or after the onset of a myeloproliferative neoplasm. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions described herein to a patient, preferably a mammal, more preferably a human, may be carried out using known procedures, at dosages and for periods of time effective to treat a myeloproliferative neoplasm in the patient. An effective amount of the therapeutic compound necessary to achieve a therapeutic effect may vary according to factors such as the state of the disease or disorder in the patient; the age, sex, and weight of the patient; and the ability of the therapeutic compound to treat a myeloproliferative neoplasm in the patient. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound described herein is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions described herein may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds described herein employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the compound(s) described herein are dictated by and directly dependent on (a) the unique characteristics of the therapeutic compound and the particular therapeutic effect to be achieved, and (b) the limitations inherent in the art of compounding/formulating such a therapeutic compound.

In certain embodiments, the compositions described herein are formulated using one or more pharmaceutically acceptable excipients or carriers. In certain embodiments, the pharmaceutical compositions described herein comprise a therapeutically effective amount of a compound described herein and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

In certain embodiments, the compositions described herein are administered to the patient in dosages that range from one to five times per day or more. In other embodiments, the compositions described herein are administered to the patient in range of dosages that include, but are not limited to, once every day, every two, days, every three days to once a week, and once every two weeks. It is readily apparent to one skilled in the art that the frequency of administration of the various combination compositions described herein varies from individual to individual depending on many factors including, but not limited to, age, disease or disorder to be treated, gender, overall health, and other factors. Thus, administration of the compounds and compositions described herein should not be construed to be limited to any particular dosage regime and the precise dosage and composition to be administered to any patient is determined by the attending physician taking all other factors about the patient into account.

The compound(s) described herein for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 350 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In some embodiments, the dose of a compound described herein is from about 1 mg and about 2,500 mg. In some embodiments, a dose of a compound described herein used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, a composition as described herein is a packaged pharmaceutical composition comprising a container holding a therapeutically effective amount of a compound described herein, alone or in combination with a second pharmaceutical agent; and instructions for using the compound to treat, or reduce one or more symptoms of a disease or disorder in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions described herein include oral, nasal, rectal, intravaginal, parenteral, buccal, sublingual or topical. The compounds for use in the compositions described herein can be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions described herein are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compound(s) described herein can be in the form of tablets or capsules prepared by conventional means with pharmaceutically acceptable excipients such as binding agents (e.g., polyvinylpyrrolidone, hydroxypropylcellulose or hydroxypropyl methylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Compositions as described herein can be prepared, packaged, or sold in a formulation suitable for oral or buccal administration. A tablet that includes a compound as described herein can, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, dispersing agents, surface-active agents, disintegrating agents, binding agents, and lubricating agents.

Suitable dispersing agents include, but are not limited to, potato starch, sodium starch glycollate, poloxamer 407, or poloxamer 188. One or more dispersing agents can each be individually present in the composition in an amount of about 0.01% w/w to about 90% w/w relative to weight of the dosage form. One or more dispersing agents can each be individually present in the composition in an amount of at least, greater than, or less than about 0.01%, 0.05%, 0.1%, 0.5%, 1%, 2%, 3%, 4%, 5%, 10%, 15%, 20%, 25%, 30%, 35%, 40%, 45%, 50%, 55%, 60%, 65%, 70%, 75%, 80%, 85%, or 90% w/w relative to weight of the dosage form.

Surface-active agents (surfactants) include cationic, anionic, or non-ionic surfactants, or combinations thereof. Suitable surfactants include, but are not limited to, behentrimonium chloride, benzalkonium chloride, benzethonium chloride, benzododecinium bromide, carbethopendecinium bromide, cetalkonium chloride, cetrimonium bromide, cetrimonium chloride, cetylpyridine chloride, didecyldimethylammonium chloride, dimethyldioctadecylammonium bromide, dimethyldioctadecylammonium chloride, domiphen bromide, lauryl methyl gluceth-10 hydroxypropyl dimonium chloride, tetramethylammonium hydroxide, thonzonium bromide, stearalkonium chloride, octenidine dihydrochloride, olaflur, N-oleyl-1,3-propanediamine, 2-acrylamido-2-methylpropane sulfonic acid, alkylbenzene sulfonates, ammonium lauryl sulfate, ammonium perfluorononanoate, docusate, disodium cocoamphodiacetate, magnesium laureth sulfate, perfluorobutanesulfonic acid, perfluorononanoic acid, perfluorooctanesulfonic acid, perfluorooctanoic acid, potassium lauryl sulfate, sodium alkyl sulfate, sodium dodecyl sulfate, sodium laurate, sodium laureth sulfate, sodium lauroyl sarcosinate, sodium myreth sulfate, sodium nonanoyloxybenzenesulfonate, sodium pareth sulfate, sodium stearate, sodium sulfosuccinate esters, cetomacrogol 1000, cetostearyl alcohol, cetyl alcohol, cocamide diethanolamine, cocamide monoethanolamine, decyl glucoside, decyl polyglucose, glycerol monostearate, octylphenoxypolyethoxyethanol CA-630, isoceteth-20, lauryl glucoside, octylphenoxypolyethoxyethanol P-40, Nonoxynol-9, Nonoxynols, nonyl phenoxypolyethoxylethanol (NP-40), octaethylene glycol monododecyl ether, N-octyl beta-D-thioglucopyranoside, octyl glucoside, oleyl alcohol, PEG-10 sunflower glycerides, pentaethylene glycol monododecyl ether, polidocanol, poloxamer, poloxamer 407, polyethoxylated tallow amine, polyglycerol polyricinoleate, polysorbate, polysorbate 20, polysorbate 80, sorbitan, sorbitan monolaurate, sorbitan monostearate, sorbitan tristearate, stearyl alcohol, surfactin, Triton X-100, and Tween 80. One or more surfactants can each be individually present in the composition in an amount of about 0.01% w/w to about 90% w/w relative to weight of the dosage form. One or more surfactants can each be individually present in the composition in an amount of at least, greater than, or less than about 0.01%, 0.05%, 0.1%, 0.5%, 1%, 2%, 3%, 4%, 5%, 10%, 15%, 20%, 25%, 30%, 35%, 40%, 45%, 50%, 55%, 60%, 65%, 70%, 75%, 80%, 85%, or 90% w/w relative to weight of the dosage form.

Suitable diluents include, but are not limited to, calcium carbonate, magnesium carbonate, magnesium oxide, sodium carbonate, lactose, microcrystalline cellulose, calcium phosphate, calcium hydrogen phosphate, and sodium phosphate, Cellactose® 80 (75% α-lactose monohydrate and 25% cellulose powder), mannitol, pre-gelatinized starch, starch, sucrose, sodium chloride, talc, anhydrous lactose, and granulated lactose. One or more diluents can each be individually present in the composition in an amount of about 0.01% w/w to about 90% w/w relative to weight of the dosage form. One or more diluents can each be individually present in the composition in an amount of at least, greater than, or less than about 0.01%, 0.05%, 0.1%, 0.5%, 1%, 2%, 3%, 4%, 5%, 10%, 15%, 20%, 25%, 30%, 35%, 40%, 45%, 50%, 55%, 60%, 65%, 70%, 75%, 80%, 85%, or 90% w/w relative to weight of the dosage form.

Suitable granulating and disintegrating agents include, but are not limited to, sucrose, copovidone, corn starch, microcrystalline cellulose, methyl cellulose, sodium starch glycollate, pregelatinized starch, povidone, sodium carboxy methyl cellulose, sodium alginate, citric acid, croscarmellose sodium, cellulose, carboxymethylcellulose calcium, colloidal silicone dioxide, crosspovidone and alginic acid. One or more granulating or disintegrating agents can each be individually present in the composition in an amount of about 0.01% w/w to about 90% w/w relative to weight of the dosage form. One or more granulating or disintegrating agents can each be individually present in the composition in an amount of at least, greater than, or less than about 0.01%, 0.05%, 0.1%, 0.5%, 1%, 2%, 3%, 4%, 5%, 10%, 15%, 20%, 25%, 30%, 35%, 40%, 45%, 50%, 55%, 60%, 65%, 70%, 75%, 80%, 85%, or 90% w/w relative to weight of the dosage form.

Suitable binding agents include, but are not limited to, gelatin, acacia, pre-gelatinized maize starch, polyvinylpyrrolidone, anhydrous lactose, lactose monohydrate, hydroxypropyl methylcellulose, methylcellulose, povidone, polyacrylamides, sucrose, dextrose, maltose, gelatin, polyethylene glycol. One or more binding agents can each be individually present in the composition in an amount of about 0.01% w/w to about 90% w/w relative to weight of the dosage form. One or more binding agents can each be individually present in the composition in an amount of at least, greater than, or less than about 0.01%, 0.05%, 0.1%, 0.5%, 1%, 2%, 3%, 4%, 5%, 10%, 15%, 20%, 25%, 30%, 35%, 40%, 45%, 50%, 55%, 60%, 65%, 70%, 75%, 80%, 85%, or 90% w/w relative to weight of the dosage form.

Suitable lubricating agents include, but are not limited to, magnesium stearate, calcium stearate, hydrogenated castor oil, glyceryl monostearate, glyceryl behenate, mineral oil, polyethylene glycol, poloxamer 407, poloxamer 188, sodium laureth sulfate, sodium benzoate, stearic acid, sodium stearyl fumarate, silica, and talc. One or more lubricating agents can each be individually present in the composition in an amount of about 0.01% w/w to about 90% w/w relative to weight of the dosage form. One or more lubricating agents can each be individually present in the composition in an amount of at least, greater than, or less than about 0.01%, 0.05%, 0.1%, 0.5%, 1%, 2%, 3%, 4%, 5%, 10%, 15%, 20%, 25%, 30%, 35%, 40%, 45%, 50%, 55%, 60%, 65%, 70%, 75%, 80%, 85%, or 90% w/w relative to weight of the dosage form.

Tablets can be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent, a preservative, or some combination of these in order to provide for pharmaceutically elegant and palatable preparation.

Tablets can also be enterically coated such that the coating begins to dissolve at a certain pH, such as at about pH 5.0 to about pH 7.5, thereby releasing a compound as described herein. The coating can contain, for example, EUDRAGIT® L, S, FS, and/or E polymers with acidic or alkaline groups to allow release of a compound as described herein in a particular location, including in any desired section(s) of the intestine. The coating can also contain, for example, EUDRAGIT® RL and/or RS polymers with cationic or neutral groups to allow for time controlled release of a compound as described hrein by pH-independent swelling.

Parenteral Administration

For parenteral administration, the compounds as described herein may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Sterile injectable forms of the compositions described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1, 3-butanediol. Among the acceptable vehicles and solvents that may be employed are water, Ringer's solution and isotonic sodium chloride solution. Sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as Ph. Helv or similar alcohol.

Additional Administration Forms

Additional dosage forms suitable for use with the compound(s) and compositions described herein include dosage forms as described in U.S. Pat. Nos. 6,340,475; 6,488,962; 6,451,808; 5,972,389; 5,582,837; and 5,007,790. Additional dosage forms suitable for use with the compound(s) and compositions described herein also include dosage forms as described in U.S. Patent Applications Nos. 20030147952; 20030104062; 20030104053; 20030044466; 20030039688; and 20020051820. Additional dosage forms suitable for use with the compound(s) and compositions described herein also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; 98/11879; WO 97/47285; WO 93/18755; and WO 90/11757.

Controlled Release Formulations and Drug Delivery Systems

In certain embodiments, the formulations described herein can be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use with the method(s) described herein may be administered in the form of microparticles, for example, by injection or in the form of wafers or discs by implantation.

In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions described herein. Thus, single unit dosage forms suitable for oral administration, such as tablets, capsules, gelcaps, and caplets, that are adapted for controlled-release are encompassed by the compositions and dosage forms described herein.

Most controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood level of the drug, and thus can affect the occurrence of side effects.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

Controlled-release of an active ingredient can be stimulated by various inducers, for example pH, temperature, enzymes, water, or other physiological conditions or compounds. The term "controlled-release component" is defined herein as a compound or compounds, including, but not limited to, polymers, polymer matrices, gels, permeable membranes, liposomes, or microspheres or a combination thereof that facilitates the controlled-release of the active ingredient. In some embodiments, the compound(s) described herein are administered to a patient, alone or in combination with another pharmaceutical agent, using a sustained release formulation. In some embodiments, the compound(s) described herein are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound described herein depends on the age, sex and weight of the patient, the current medical condition of the patient and the progression of a myeloproliferative neoplasm in the patient being treated. The skilled artisan is able to determine appropriate dosages depending on these and other factors.

A suitable dose of a compound described herein can be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the compound(s) described herein is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced to a level at which the improved disease is retained. In certain embodiments, patients require intermittent treatment on a long-term basis upon any recurrence of symptoms and/or infection.

The compounds described herein can be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

Examples

Various embodiments of the present application can be better understood by reference to the following Examples which are offered by way of illustration. The scope of the present application is not limited to the Examples given herein.

Generation of Recombinant Baculoviruses

The isolated JH1 and JH2 domains of human JAK2 were expressed in baculovirus-infected Sf9 insect cells and purified similar to the procedure reported previously. The two reported JH2 domain constructs contained residues 536-812 (with either mutations W659A, W777A, F794H, or mutations W777A, F794H, V617F), followed by a C-terminal thrombin cleavage site and 6×His-tag. The reported JH1 domain construct included an N-terminal 6×His-tag, followed by a TEV cleavage site and residues 840-1132. Recombinant bacmid and baculoviruses were generated using the Bac-to-Bac baculovirus expression system (Invitrogene). DH10Bac competent cells were transformed with recombinant pFastBac plasmid containing the gene of interest to generate the recombinant expression bacmid. P1, P2 and P3 baculovirus stocks were produced according to the manufacturer's instructions. Sf9 cells were grown in HyClone SFX-Insect cell culture media (GE Healthcare) at 27° C.

JAK2 Protein Expression and Purification

Sf9 cells were grown in HyClone SFX-Insect cell culture media to a density of 2.5-4.0×10$^6$ cells/mL, followed by transfection with P3 baculovirus stock. After incubation for 48 h at 27° C., cells were harvested and separated from the supernatant by centrifugation (4000 rpm, 30 mins). Purification of the JH1 and JH2 domains of JAK2 was performed in an identical manner. Cell pellets were resuspended in lysis buffer composed of 20 mM Tris pH 8.0, 500 mM NaCl, 20% glycerol, 0.25 mM TCEP, and cOmplete EDTA free protease inhibitor (Roche). Cells were lysed by sonication, followed by pressure homogenization using an Emulsiflux cell disruptor (Avestin). Lysate was separated from cell debris by centrifugation (45 min, 16,500 rpm). Ni-NTA agarose beads (Qiagen) were added in batch mode, and incubated for 2 h at 4° C. Beads were washed with lysis buffer containing 10 mM imidazole, and JAK2 protein was eluted with lysis buffer containing 200 mM imidazole. The eluate was dialyzed overnight at 4° C. using a MWCO 3.5 kDa Slide-A-Lyzer dialysis cassette (Thermo Fisher Scientific) against a low salt dialysis buffer composed of 20 mM Tris pH 8.0, 25 mM NaCl, 20% glycerol, and 0.25 mM TCEP. The dialysis product was filtered through a 0.45 μm membrane and loaded onto a pre-equilibrated Mono Q HR 16/19 column (GE Healthcare) linked to an ÄKTA pure protein purification system (GE Healthcare). Protein was eluted applying a linear gradient starting with dialysis buffer and ending with dialysis buffer containing 500 mM NaCl. JAK2 fractions were pooled and applied to a Superdex 75 10/300 (GE Healthcare) pre-equilibrated with a buffer composed of 20 mM Tris pH 8.0, 100 mM NaCl, 10% glycerol, and 1.0 mM TCEP. Purified protein was aliquoted, flash-frozen in liquid nitrogen, and stored at −80° C.

Fluorescence Polarization (FP) Assays

Determination of Tracer Affinity with JAK2-JH2-WT, JAK2-JH2-V617F, and JAK2-JH1

Figure 8A:
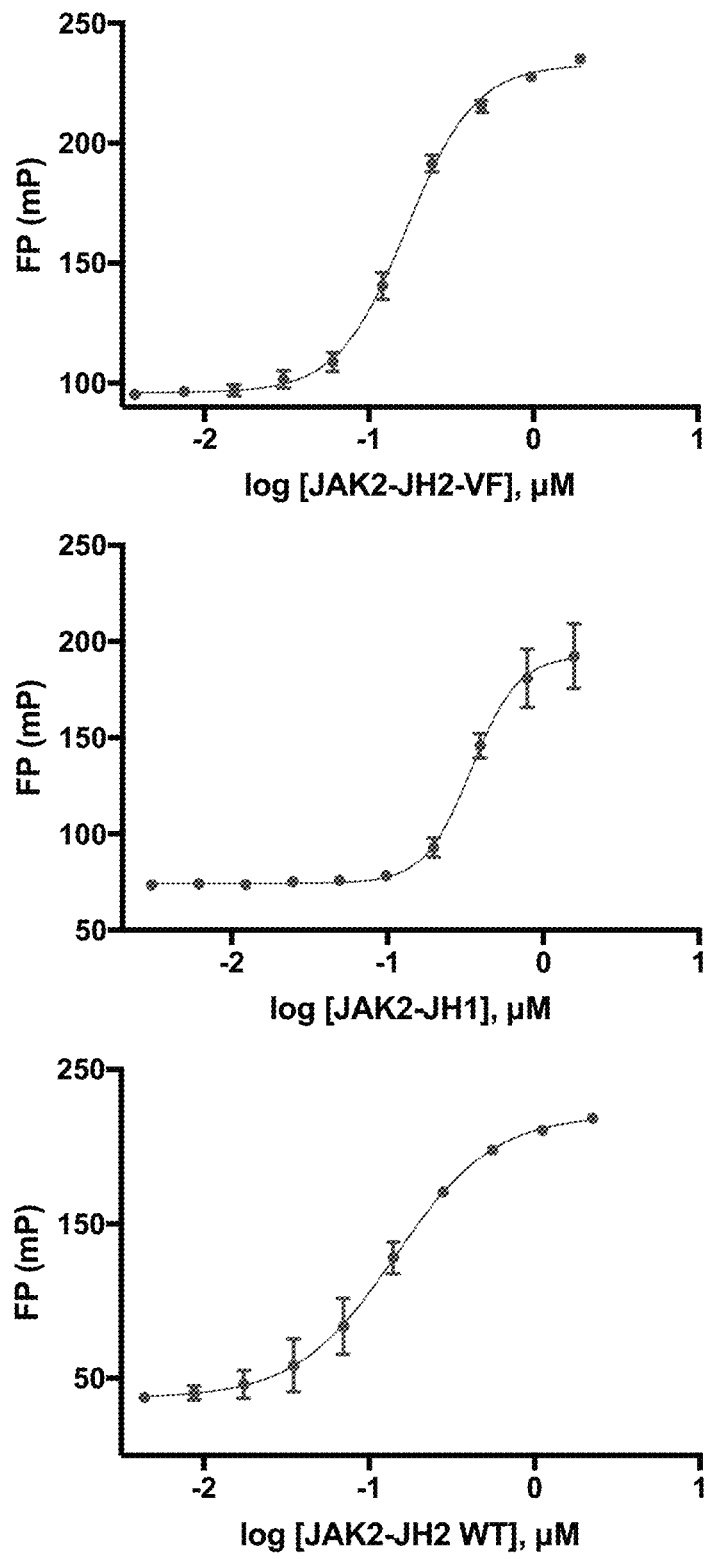
FIGS. 8A-8B show the determination of binding affinities for tracer (6 nM) through saturation experiments.
Figure 8B:
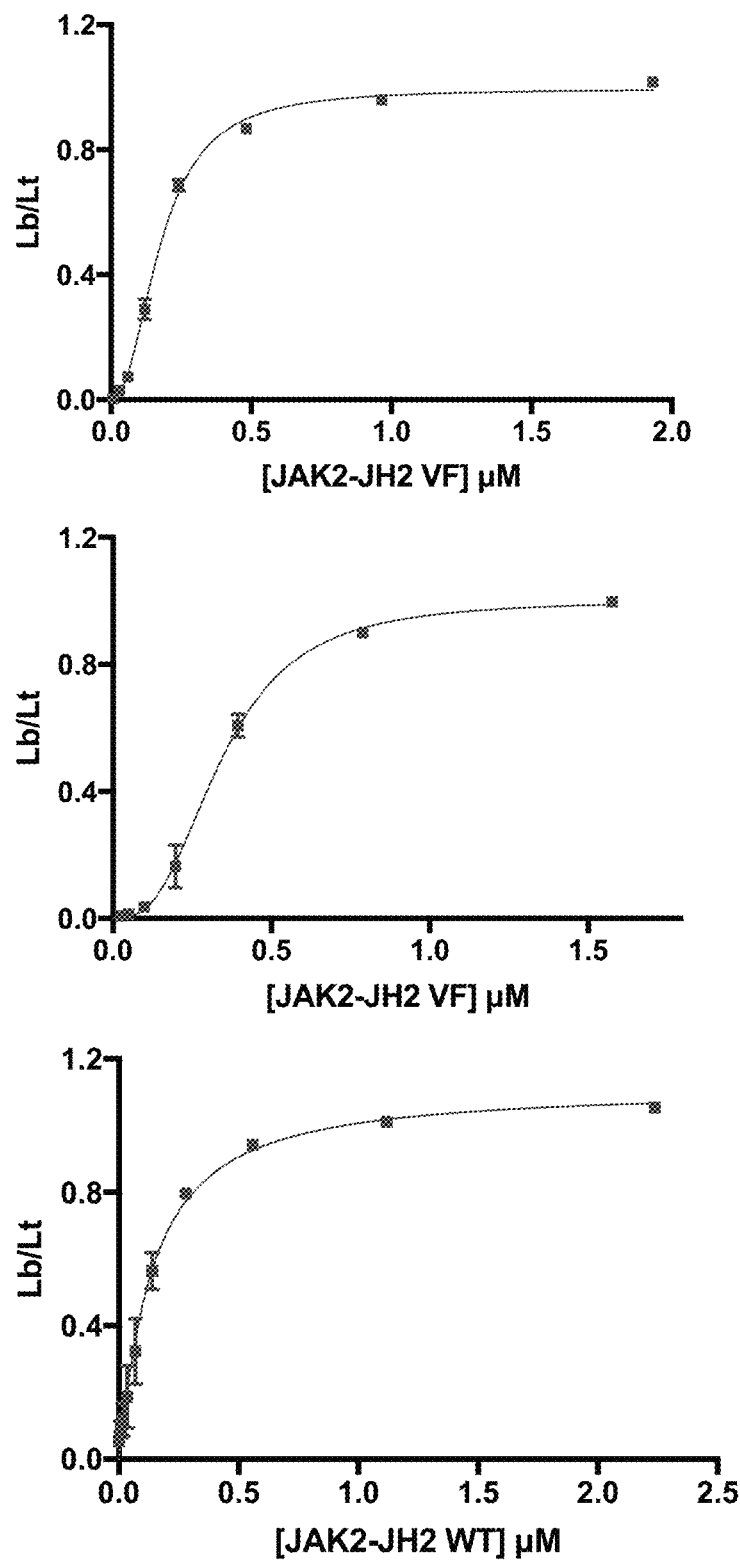
Figure 9A:
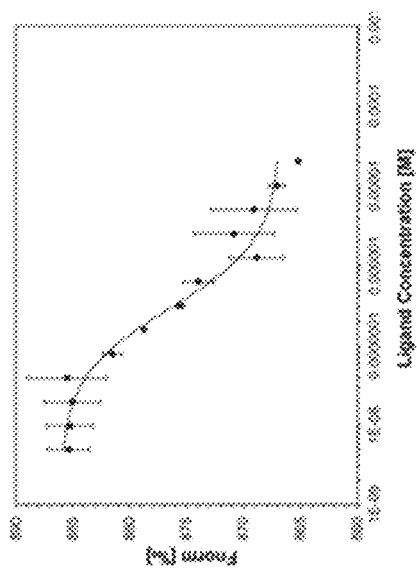
FIGS. 9A-9E show the MST dose-response curves for the binding reaction between JAK2 JH2 mutant W659A, W777A, F794H and (FIG. 9A) 1, (FIG. 9B) 10, and (FIG. 9C) 12. MST dose-response curves for the binding reaction between JAK2 JH2 mutant W777A, F794H, V617F and (FIG. 9D) 10, and (FIG. 9E) 12.
Figure 9B:
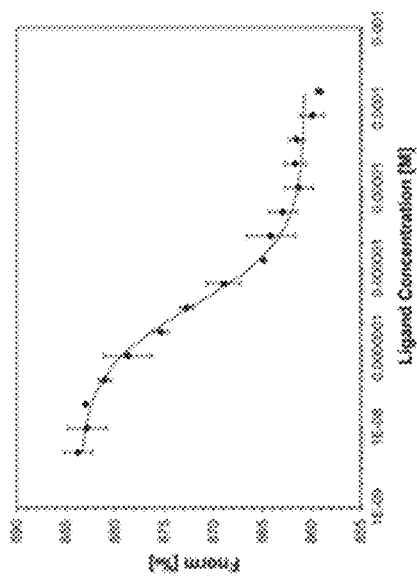
Figure 9C:
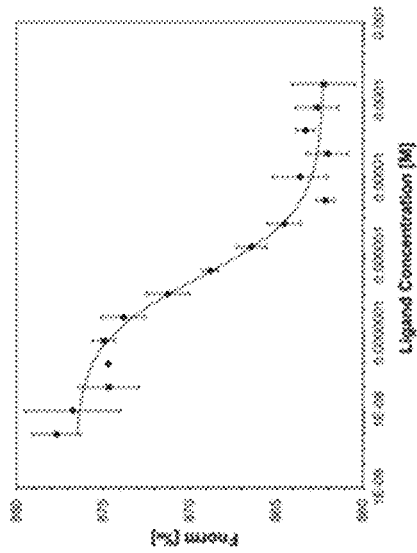
Figure 9D:
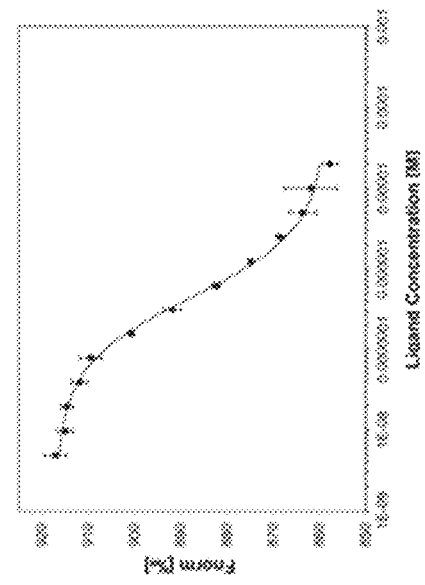
Figure 9E:
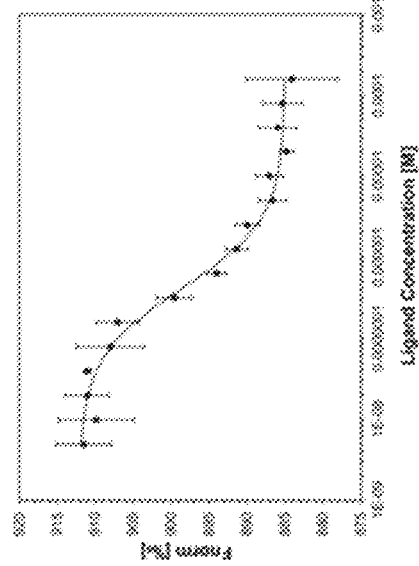
Figure 10C:
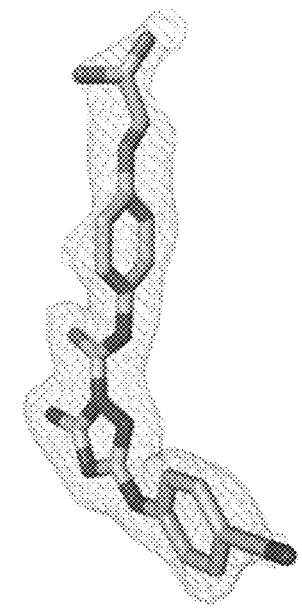
FIGS. 10A-10E show the Polder omit electron density maps of small-molecule ligands (FIG. 10A) 3 (3.2 σ), (FIG. 10B) 4 (4.0 σ), (FIG. 10C) 9 (3.0 σ), (FIG. 10D) 10 (4.5 σ), and (FIG. 10E) 12 (3.5 σ). Ligands are shown with light orange carbon atoms and color-coded heteroatoms.
Figure 10B:
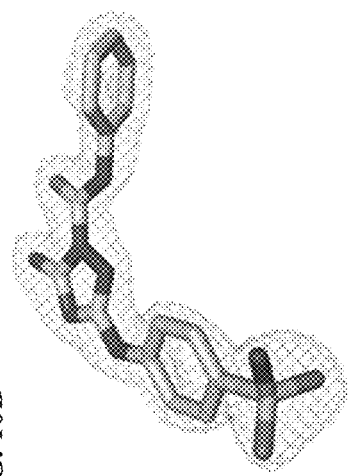
Figure 10A:
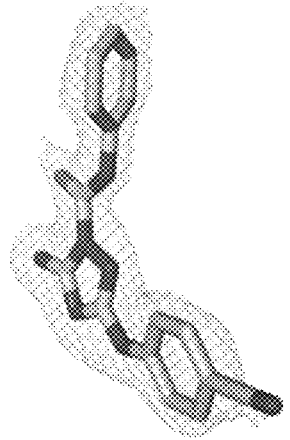
Figure 10E:
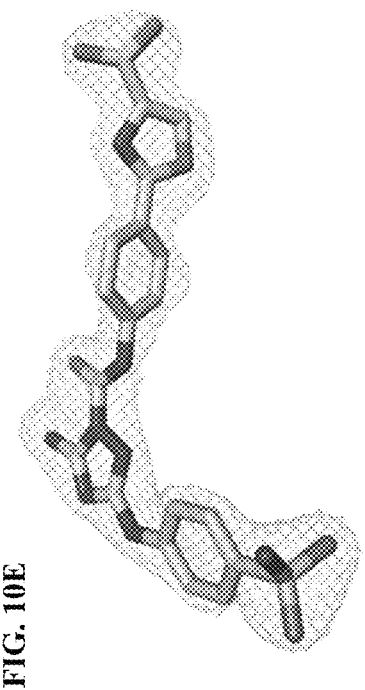
Figure 10D:
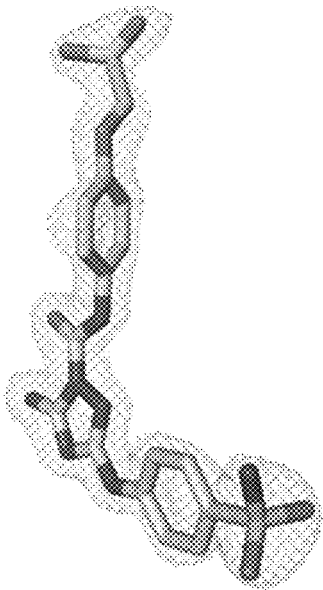

In a flat black bottom 96 well plate (Corning), the buffer (20 mM Tris-HCl pH 8.0, 150 mM NaCl, 20% Glycerol, 0.5 mM TCEP, 0.01% Tween 20) is added—200 μL to column 1 (blank), 295 μL to column 2, 150 μL to columns 3-12. 5 μL of protein (179.0 μM JAK2-JH2-WT, 154.7 μM JAK2-JH2-V617F, 126.3 μM JAK2-JH1) were added to column 2. 150 μL was transferred, using a multichannel pipette, from column 2 to 3, 3 to 4, 4 to 5, until reaching the last column to make a serial dilutions (1:2). 50 μl of 24.0 nM tracer were added from columns 2-12 and fluorescence polarization was measured at $\lambda_{exc}$=485±20 nm, $\lambda_{em}$=535±25 nm using an Infinite F500 plate reader until no FP variation was observed. From the lowest and highest FP values (tracer free and tracer fully bound to JAK) fraction of ligand bound to the protein to ligand total ($L_b/L_t$) was calculated for each concentration of the JAK2-JH2-WT, JAK2-JH2-V617F, and JAK2-JH1 (FIGS. 8A-8B). Experiments were carried out by quadruplicates in three independent experiments. The data provided a typical saturation-binding curve and $K_d$ was calculated fitting the results to the Hill equation using Prism 7.

Competitive FP Assay

In a flat black bottom 96 well plate (Corning), 200 μL of FP buffer were added to column 1 (blank), 150 μL to column 2, and 140 μL to columns 3-12. 10 μL of 2.96 μM of JAK2-JH2 WT (3.52 μM for JAK2-JH2-VF, and 6.93 μM for JAK2-JH1), were added to columns 3-12, followed by the addition of 2 μL of DMSO to columns 1-3. 2 μL of inhibitor in DMSO at different concentrations were added from column 4 to 12. 50 μL of 24 nM of tracer were added to columns 2-12. Fluorescence polarization was measured at $\lambda_{exc}$=485±20 nm, $\lambda_{em}$=535±25 nm for 1 hour. Experiments were carried out by quadruplicates in three independent experiments. Data were analyzed by a least-squares non-linear fit, generated using Prism 7 in order to determine the compound's $IC_{50}$. $K_d$ values for each inhibitor are calculated using the following equation based on the $IC_{50}$, $K_d$ of the tracer ($K_d^t$), total ($L_t$) and bound ($L_b$) tracer, as well as total protein concentration ($P_t$)[13]

$$K_d^I = \frac{L_b IC_{50} K_d^t}{P_t L_t + L_b(P_t - L_t + L_b - K_d^t)}$$

Microscale Thermophoresis Assay

MST measurements were performed with a Monolith NT.115Pico device (NanoTemper Technologies). JH2 domain protein (triple mutant W659A, W777A, F794H, or triple mutant W777A, F794H, V617F) was fluorescently labeled with the His-tag labeling kit RED-tris-NTA 2nd generation. All dilutions were prepared with a buffer composed of 20 mM HEPES pH 8.0, 150 mM NaCl, 5% glycerol, and 0.05% Tween. Protein was labeled by incubating a mixture of 150 nM protein and 50 nM dye for 30 min at ambient temperature. MST measurements were performed with protein and dye concentrations adjusted to 30 nM and 10 nM, respectively. The serial dilution of 1 and 10 ranged from 160 μM to 0.00488 for 12 from 20 μM to 0.00488 and for 15 from 20 to 0.00061 μM. The serial dilution of 1 and 10 ranged from 160 μM to 0.00488 and for 12 from 20 μM to 0.00488 μM. All measurement samples contained a constant DMSO concentration of 3%. Measurements were performed with standard capillaries (mutant W659A, W777A, F794H) or premium capillaries (mutant W777A, F794H, V617F), medium MST power, and 5% excitation power at ambient temperature. All measurements were performed in triplicate, and were analyzed with the MO.Affinity Analysis software (NanoTemper). Curves are displayed in FIGS. 9A-9E.

Protein Crystallization

Crystals of JAK2 JH2 were grown by hanging drop vapor diffusion at 4° C. Crystals were prepared by adding 1 μL of protein (6 mg/mL) in a solution composed of 20 mM Tris pH 8.0, 100 mM NaCl, 10% glycerol, and 1 mM TCEP to 1 μL of reservoir solution composed of 0.1 M Tris pH 8.0, 0.2 M sodium acetate, 12-24% PEG4000, and 1 mM TCEP. Crystallization was induced by streak seeding, and crystals grew to full size within a week. Complexes of JH2 with small-molecule ligands were prepared by ligand soaking. Therefore, crystals were transferred into a solution of 0.1 M Tris pH 8.0, 0.2 M sodium acetate, 22% PEG4000, 1 mM TCEP, 8% DMSO, and 4 mM of the respective small-molecule ligand. After 24 h of incubation, crystals were briefly exposed to a cryobuffer (0.1 M Tris pH 8.0, 0.2 M sodium acetate, 22% PEG4000, 1 mM TCEP, 8% DMSO, 4 mM of the respective small-molecule ligand, and 20% glycerol), and flash-frozen in liquid nitrogen.

Crystal structures for complexes of five of the new compounds (3, 4, 9, 10,12) with JAK2 JH2 were also obtained at 1.7-2.1 Å resolution using an in-house X-ray diffractometer or the Advanced Photon Source at Argonne National Laboratories.

TABLE 4

Crystallographic data collection and refinement statistics of JAK2 JH2-ligand complexes[a]

| | small-molecule ligand | | | | |
| --- | --- | --- | --- | --- | --- |
| | 3 | 4 | 9 | 10 | 12 |
| PDB ID | 6OAV | 6OBB | 6OBL | 6OBF | 6OCC |
| Data collection and processing | | | | | |
| space group unit cell parameters: | $P2_1$ | $P2_1$ | $P2_1$ | $P2_1$ | $P2_1$ |
| a, b, c (Å) | 44.1, 57.4, 60.7 | 44.7, 58.0, 61.0 | 43.6, 57.8, 61.0 | 44.2, 57.4, 60.6 | 44.7, 57.6, 61.7 |
| α, β, γ(°) | 90.0, 110.4, 90.0 | 90.0, 110.6, 90.0 | 90.0, 110.7, 90.0 | 90.0, 111.2, 90.0 | 90.0, 111.1, 90.0 |
| Matthews coefficient (Å³/Da)[b] | 2.3 | 2.3 | 2.3 | 2.3 | 2.3 |
| solvent content (%)[b] | 47 | 47 | 47 | 47 | 47 |

TABLE 4-continued

Crystallographic data collection and refinement statistics of JAK2 JH2-ligand complexes[a]

| | small-molecule ligand | | | | |
|---|---|---|---|---|---|
| | 3 | 4 | 9 | 10 | 12 |
| Diffraction data | | | | | |
| resolution range (Å) | 200.00-1.94 | 50.00-1.90 | 200.00-2.06 | 50.00-1.71 | 50.00-2.03 |
| | (2.06-1.94) | (1.93-1.90) | (2.19-2.06) | (1.74-1.71) | (2.07-2.03) |
| unique reflections | 20958 (3331) | 22636 (953) | 17135 (2489) | 31289 (1569) | 18725 (855) |
| $R_{sym}$ (%) | 10.3 (87.2) | 10.7 (70.2) | 10.5 (75.5) | 9.5 (92.4) | 12.7 (52.7) |
| CC1/2 | 0.997 (0.867) | 0.956 (0.752) | 0.996 (0.847) | 0.958 (0.822) | 0.945 (0.723) |
| $<I/\sigma(I)>$ | 11.65 (2.05) | 17.5 (1.4) | 9.9 (2.1) | 18.6 (2.1) | 12.9 (2.0) |
| completeness (%) | 98.6 (97.1) | 98.8 (82.2) | 96.9 (87.7) | 99.9 (99.8) | 99.6 (94.6) |
| redundancy | 5.9 (5.6) | 8.3 (3.7) | 5.0 (4.4) | 6.8 (5.8) | 5.8 (3.7) |
| WilsonB factor (Å$^2$) | 29.7 | 24.5 | 32.8 | 21.3 | 24.9 |
| Refinement | | | | | |
| resolution range (Å) | 41.34-1.94 | 41.82-1.90 | 57.10-2.06 | 41.25-1.71 | 33.76-2.03 |
| reflections used (work/free) | 19874/1048 | 21367/1173 | 16247/853 | 29074/1506 | 17467/930 |
| $R_{work}/R_{free}$ (%) | 20.0/23.6 | 19.6/22.5 | 19.8/23.9 | 19.8/22.2 | 22.48/27.18 |
| protein residues | 272 | 272 | 272 | 272 | 268 |
| inhibitor atoms | 24 | 26 | 29 | 31 | 34 |
| water molecules | 103 | 118 | 42 | 142 | 49 |
| RMSD from ideality: | | | | | |
| bond lengths (Å) | 0.007 | 0.007 | 0.006 | 0.006 | 0.007 |
| bond angles (°) | 0.8 | 0.8 | 0.8 | 0.8 | 0.9 |
| Ramachandran plot:[c] | | | | | |
| Ramachandran favored (%) | 98.2 | 98.9 | 96.7 | 98.9 | 97.0 |
| Ramachandran outliers (%) | 0.4 | 0.0 | 0.0 | 0.0 | 0.0 |
| Mean B factors (Å$^2$): | | | | | |
| protein | 32.0 | 26.9 | 35.4 | 27.0 | 28.0 |
| inhibitor | 35.3 | 26.9 | 30.9 | 27.4 | 27.2 |
| water molecules | 35.0 | 29.7 | 35.7 | 31.2 | 26.7 |

[a]Values in parenthesis describe the highest resolution shell.
[b]Computed with CCP4 Matthews_coef.
[c]Computed with MolProbity.

Collection of X-ray Diffraction Data and Data Processing

All datasets were collected at 100K. Datasets of JH2 in complex with 4, 10, and 12 were collected in-house on a Rigaku MicroMax-007HF X-ray generator (Cu rotating anode; λ=1.54 Å) with a Dectris Pilatus 200K detector. The dataset of JH2 in complex with 3 was collected at the Advanced Photon Source (APS; Argonne, Illinois, USA) on beamline 24-ID-E with a Dectris Eiger 16M detector (λ=0.97918 Å). The dataset of JH2 in complex with 9 was collected at the APS beamline 24-ID-C with a Dectris Pilatus 6M detector (λ=0.97910 Å). Datasets of 4, 10, and 12 were indexed, integrated, and scaled with HKL2000. Datasets of 3 and 9 were indexed, integrated, and scaled with XDS. Diffraction data and refinement statistics are listed in Table 4.

Crystal Structure Determination and Refinement

All datasets were phased by molecular replacement using Phaser. The model with PDB ID 5USZ was used as a search model. Crystal structure refinement was performed with PHENIXREFINE (version 1.11.1-2575). For cross-validation of the model, 5% of the reflections (randomly selected and excluded from the refinement) were used for the calculation of Rfree. Cartesian simulated annealing was performed during the first refinement cycle. All subsequent refinement cycles included refinement of XYZ coordinates and refinement of isotropic ADPs. Manual model building was performed with Coot. SMILES codes of small-molecule ligands were created with MOLINSPIRATION, and ligands were built and restraints were generated with eLBOW. Omit maps of the electron densities of the ligands are displayed in FIGS. 10A-10E.

Molecular Design and Assays

Molecular design emphasized inspection of hundreds of trial structures for JAK2 JH2 complexes built with the BOMB (Biochemical and Organic Model Builder) program and energy-minimized with MCPRO using the OPLS-AA/M force field for proteins and OPLS/CM1A for ligands. Free energy perturbation (FEP) calculations were also carried out in some cases to better predict potential differences in free energies of binding for analogues; these calculations included ca. 2000 explicit water molecules and extensive sampling of configurations for the JAK2 JH2 protein, ligands and water. The principal assays measured binding constants with JAK2 JH2, V617F JH2, and JH1 via fluorescence polarization (FP) using a fluorescein-conjugate of 1 as the tracer. The assay followed the previous description with minor changes to the buffer composition, as fully described in the Supporting Information (SI). For several compounds, microscale thermophoresis was carried out as an additional approach for obtaining $K_d$ values. The present measurements like the prior ITC and FP assays were carried out at pH 8.0, which provided more consistent results than current tests at pH 7.0 and 8.5.

For the FP assays with JAK2 JH2, 1 was used as a control compound so multiple $K_d$ results were obtained yielding an average value of 0.456±0.124 µM (Table 1). The result from the MST measurements, 0.489±0.084 µM, was notably consistent given the differences in the utilized buffers. These values are somewhat lower than the previous FP result of 0.80±0.05 µM, and they are significantly higher than the ITC result of 0.106 µM, and of a recent report of 0.094 µM from intrinsic tryptophan fluorescence.

Cloning and Expression of Full-Length JAK2

Full-length cDNA encoding human JAK2 (residues 1-1132) wild-type (NP_001309123) and V617F mutant with C-terminal FLAG-Tag (DYKDDDDK) were amplified by PCR, and subcloned into a modified pOptiVec expression vector (Invitrogen). JAK2 constructs were expressed in HEK293T cells grown at 37° C. at 5% $CO_2$ in DMEM (Gibco) supplemented with 10% (v/v) FBS (Gibco) and 1% (v/v) penicillin-streptomycin (Gibco). HEK-293T cells were transiently transfected using Lipofectamin 2000 (Invitrogen) according to manufacturer's instructions. 36 h post-transfection, cells were washed twice with ice-cold PBS, and lysed with ice-cold lysis buffer (50 mM HEPES pH 7.4, 150 mM NaCl, 10% (v/v) glycerol, 1% (v/v) Triton-X 100, 1 mM EDTA, 1 mM EGTA, 25 mM NaF, 1.5 mM $MgCl_2$, 1.0 mM $Na_3VO_4$, Roche complete mini EDTA-free protease inhibitor cocktail mixture). The lysate was centrifuged (20 min, 13000×g), and the lysate supernatant was flash-frozen in liquid nitrogen and stored at −80° C.

Immunoprecipitation and In Vitro Kinase Assay

JAK2 protein was immunoprecipitated from the lysate supernatant by adding anti-FLAG M2 antibody (Sigma-Aldrich, no. F1804) and protein G-PLUS agarose (Santa Cruz Biotechnology, no. sc-2002) followed by incubation overnight while rocking at 4° C. Immunoprecipitates were washed four times with wash buffer (50 mM HEPES pH 7.4, 150 mM NaCl, 10% (v/v) glycerol, 0.1% (v/v) Triton-X 100, 1 mM EDTA, 1 mM EGTA, 25 mM NaF, 1.5 mM $MgCl_2$, 1.0 mM $Na_3VO_4$, Roche complete mini EDTA-free protease inhibitor cocktail mixture), and once with kinase reaction buffer (50 mM HEPES pH 7.4, 150 mM NaCl, 0.5 mM DTT, 5 mM $MnCl_2$). The [λ-$^{32}$P]ATP in vitro kinase activity assay was performed based on a previously published protocols. Washed immunoprecipitates were divided into equal parts, centrifuged, their residual solvent was removed, and the resulting pellets were resuspended in 25 µL kinase reaction buffer containing different concentrations of 1 or 10, followed by incubation for 1 h at 4° C. The autophosphorylation reaction of JAK2 was initiated by adding 25 µL of phosphorylation mixture consisting of kinase reaction buffer supplemented with 10 µM cold ATP, and 2 µCi (for JAK2 V617F) or 5 µCi (for JAK2 wild-type) of [λ-$^{32}$P]ATP (EasyTides, PerkinElmer) per reaction. The mixture was allowed to react for 15 min at 30° C. (within the linear range of kinase activity), and stopped by putting on ice and adding 18 µL of reducing Laemmli sample buffer (4×). Samples were heated at 95° C. for 5 min, and run by 7.5% SDS-PAGE. Gels were rocked in a solution of 10% glycerol, 20% ethanol for 30 min, dried with a vacuum drier, and autoradiographed using a phosphor imager. To calculate $IC_{50}$ values, phosphor autoradiography was quantified using ImageJ, and curves were plotted with Prism 8.0 (GraphPad Software Inc., La Jolla, CA).

General Synthetic Methods

All purchased compounds were used as received from vendors without further purification. Reactions were conducted under a nitrogen atmosphere and monitored by thin layer chromatography on Merck silica gel plates pre-coated with fluorescent indicator F254. Visualization of plates was achieved with UV light or potassium permanganate stain. Mass analysis of intermediates was done with an Agilent 6120 Quadrupole LC/MS instrument via electrospray ionization. Chromatographic purification was performed with a Teledyne ISCO CombiFlash automated system employing RediSep (particle size: 35-70 µm; pore size: 60 Å) or RediSep Gold (particle size: 20-40 µm; pore size: 60 Å disposable cartridge columns. In some cases, additional purification by preparatory TLC was done (SiliaPlate, F254-coated, 2000 µm). $^1$H and $^{13}$C NMR spectra were recorded on Agilent $DD_2$ 400 MHz, $DD_2$ 500 MHz, or $DD_2$ 600 MHz instruments. HRMS analysis of final products was done on a Waters Xevo QTOF with a Z-spray electrospray ionization source. Purity of all assayed compounds was determined on a Shimadzu Prominence HPLC equipped with an Agilent Poroshell 120 SB-C18 2.7 µm column, using 0.1% TFA in water and 0.1% TFA in acetonitrile as the mobile phase. The compounds (2-4, 6-10, 12, 14, 15) were >95% pure by analytical HPLC, while the purities of three non-key compounds, 5, 11, and 13, were 94%, 91%, and 90%, respectively. The HPLC traces of all compounds showed no minor peaks above 3%. Furthermore, the NMR spectra presented below for the compounds indicate that the compounds may be of higher purity. It is possible that the HPLC results may be affected by formation of dimers of the carboxylic acids or alternative protonation patterns. The systematic SAR data and multiple crystal structures reported here including for 12 bound to JAK2 JH2 demonstrate that the reported binding data for this series is reflective of the compounds themselves.

Scheme 3. Synthesis of 17a-b[a]

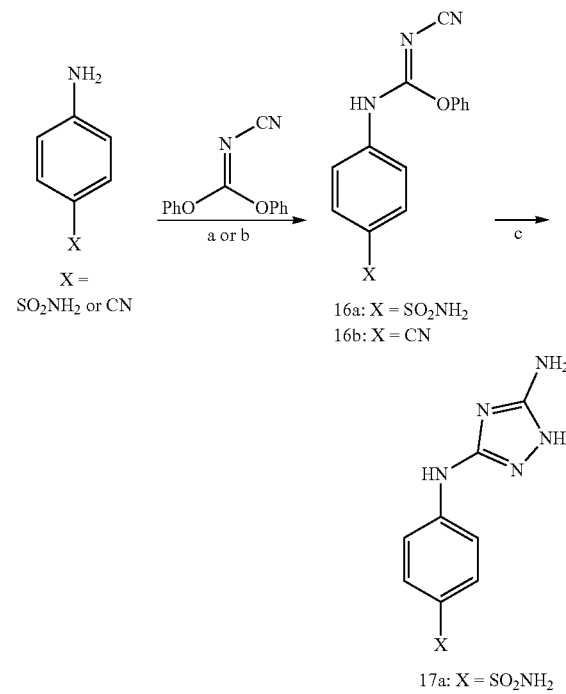

17a: X = $SO_2NH_2$
17b: X = CN

[a] Reagents and conditions:
(a) THF, reflux, 24 h;
(b) NaH, THF, reflux, 24 h;
(c) Hydrazine, reflux, 8-19 h.

Synthesis of Phenyl-N'-cyano-N-(4-sulfamoylphenyl)carbamimidate (16a)

Sulfanilamide (4.0 g, 23.2 mmol) was combined with diphenyl cyanocarbonimidate (5.5 g, 23.2 mmol) in anhydrous tetrahydrofuran (26 mL, 0.9 M). The reaction mixture was stirred at reflux for 24 h and afterwards was concentrated under reduced pressure. The residue was suspended in dichloromethane, filtered, washed with dichloromethane, and dried overnight to provide the title product as a pale white solid (6.2 g, 84% yield). $^1$H NMR (500 MHz, DMSO-$d_6$) δ 11.12 (s, 1H), 7.83 (d, J=8.5 Hz, 2H), 7.66 (d, J=8.5 Hz, 2H), 7.46 (t, J=7.8 Hz, 2H), 7.36 (s, 2H), 7.35-7.29 (m, 3H). $^{13}$C NMR (126 MHz, DMSO-$d_6$) δ 151.43, 140.97, 139.12, 129.85, 127.39, 126.51, 126.39, 123.32, 120.79, 112.39. ESI-MS m/z: [M+H]$^+$: 317.1.

Synthesis of Phenyl-N'-cyano-N-(4-cyanophenyl)carbamimidate (16b)

Sodium hydride (760 mg (60% dispersion in mineral oil), 19.0 mmol) was added at 0° C. to a mixture of 4-aminobenzonitrile (2.2 g, 19.0 mmol) in anhydrous tetrahydrofuran (65 mL, 0.3 M). The mixture was stirred at 60° C. for 45 min, followed by portion-wise addition of diphenyl cyanocarbonimidate (4.0 g, 17.0 mmol). The reaction was brought to reflux and allowed to run for 24 h. The crude mixture was quenched with methanol and solvent was evaporated under reduced pressure. Hot acetone was added until complete dissolution of the residue, at which point hexanes were added until the solution became cloudy. The precipitate was filtered to provide the title product as a white, fluffy solid (3.11 g, 70% yield). $^1$H NMR (400 MHz, DMSO-$d_6$) δ 11.21 (s, 1H), 7.86 (d, J=8.1 Hz, 2H), 7.66 (d, J=8.1 Hz, 2H), 7.46 (t, J=7.6 Hz, 2H), 7.37-7.28 (m, 3H). $^{13}$C NMR (151 MHz, DMSO-$d_6$) δ 157.71, 155.53, 154.16, 132.12, 128.84, 124.11, 123.67, 121.98, 121.78, 120.32, 100.73. ESI-MS m/z: [M+H]$^+$: 263.1.

Synthesis of 4-((5-amino-1H-1,2,4-triazol-3-yl)amino)benzenesulfonamide (17a)

Compound 16a (5.0 g, 15.9 mmol) was suspended in anhydrous tetrahydrofuran (18 mL, 0.9 M) and hydrazine (17.5 mL (1 M in THF), 17.5 mmol) was added at 0° C. The reaction mixture was warmed to room temperature and stirred at reflux for 7.5 h. The mixture was then filtered, washed three times with tetrahydrofuran, and dried overnight to afford the title product as white solid (3.4 g, 84.5% yield). $^1$H NMR (600 MHz, DMSO-$d_6$) δ 11.30 (s, 1H), 9.19 (s, 1H), 7.60 (q, J=9.0 Hz, 4H), 7.03 (s, 2H), 5.95 (s, 2H). $^{13}$C NMR (151 MHz, DMSO-$d_6$) δ 157.22, 155.50, 145.46, 133.07, 126.72, 114.55. ESI-MS m/z: [M+H]$^+$: 255.1.

Synthesis of 4-((5-amino-1H-1,2,4-triazol-3-yl)amino)benzonitrile (17b)

Compound 16b (1.0 g, 3.8 mmol) was suspended in dry tetrahydrofuran (11 mL, 0.3 M) and combined with hydrazine (7.6 mL (1 M in THF), 7.6 mmol) at 0° C. The reaction mixture was brought to reflux and stirred for 19 h, then was concentrated and purified by column chromatography (DCM/MeOH) to afford a yellow solid (461 mg, 61% yield). $^1$H NMR (400 MHz, DMSO-$d_6$) δ 11.38 (s, 1H), 9.40 (s, 1H), 7.60 (q, J=8.9 Hz, 4H), 5.97 (s, 2H). $^{13}$C NMR (151 MHz, DMSO-$d_6$) δ 155.23, 147.97, 146.51, 133.04, 120.16, 115.49, 99.10. ESI-MS m/z: [M+H]$^+$: 201.1.

Scheme 4. Synthesis of 18a-b$^a$

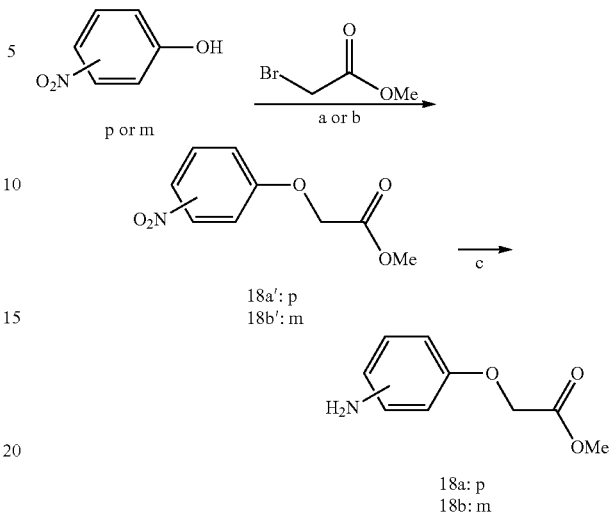

$^a$Reagents and conditions:
(a) K$_2$CO$_3$, MeCN, r.t., 16.5 h;
(b) K$_2$CO$_3$, acetone, reflux, 5 h;
(c) H$_2$, Pd/C, THF:MeOH, 20 h.

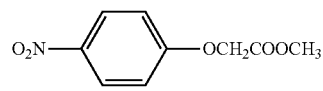

Synthesis of Methyl 2-(4-nitrophenoxy)acetate (18a')

Para-nitrophenol (1.5 g, 10.8 mmol) was suspended in dry acetonitrile (50 mL, 0.2 M) and followed by addition of potassium carbonate (2.98 g, 21.6 mmol). The mixture was allowed to stir until homogenized, methyl-2-bromoacetate (1.0 mL, 10.8 mmol) was added, and stirring continued for 16.5 h at room temperature. The crude mixture was concentrated and diluted with ethyl acetate (50 mL), washed with water (2×20 mL) and brine (2×15 mL), and was dried over anhydrous sodium sulfate. Solvent was evaporated under vacuum to afford the title compound as a white solid (2.0 g, 89% yield). $^1$H NMR (400 MHz, DMSO-$d_6$) δ 8.21 (d, J=9.3 Hz, 2H), 7.17 (d, J=9.3 Hz, 2H), 5.01 (s, 2H), 3.71 (s, 3H). $^{13}$C NMR (101 MHz, DMSO-$d_6$) δ 168.47, 162.78, 141.35, 125.78, 115.23, 65.02, 52.01. ESI-MS m/z: [M+H]$^+$: 212.1.

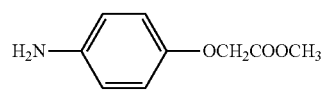

Synthesis of Methyl 2-(4-aminophenoxy)acetate (18a)

Pd/C (10% Pd basis, 565 mg) was added to a solution of 18a' (1.85 g, 8.8 mmol) in 1:1 tetrahydrofuran:methanol (50 mL). The mixture stirred under hydrogen atmosphere for 20 h. The mixture was then filtered through celite and purified by column chromatography (Hexanes/EtOAc) to provide the title compound as an orange solid (1.3 g, 82% yield). $^1$H NMR (400 MHz, DMSO-$d_6$) δ 6.64 (d, J=8.8 Hz, 2H), 6.49 (d, J=8.8 Hz, 2H), 4.65 (s, 2H), 4.59 (s, 2H), 3.67 (s, 3H). $^{13}$C NMR (101 MHz, DMSO-$d_6$) δ 169.71, 148.93, 143.08, 115.49, 114.75, 65.52, 51.60. ESI-MS m/z: [M+H]$^+$: 182.1.

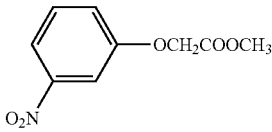

Synthesis of Methyl 2-(3-nitrophenoxy)acetate (18b')

Potassium carbonate (2.0 g, 14.5 mmol) was added to a mixture of m-nitrophenol (1.5 g, 10.8 mmol) in dry acetone (5 mL, 2 M). The mixture was allowed to stir until homogenized, and then methyl-2-bromoacetate (1.3 mL, 14.1 mmol) was added. The reaction refluxed for 5 h, then was cooled to room temperature and poured into water (25 mL). The precipitate was filtered and dried in a Buchner funnel under house vacuum overnight to provide the title compound as a pale white solid (2.2 g, 96% yield). $^1$h NMR (400 MHz, DMSO-$d_6$) δ 7.85 (dd, J=8.1, 2.0 Hz, 1H), 7.73 (t, J=2.3 Hz, 1H), 7.59 (t, J=8.2 Hz, 1H), 7.45 (dd, J=8.3, 2.5 Hz, 1H), 5.00 (s, 2H), 3.71 (s, 3H). $^{13}$C NMR (101 MHz, DMSO-$d_6$) δ 168.79, 158.15, 148.70, 130.79, 121.96, 116.22, 109.10, 65.01, 52.00. ESI-MS m/z: [M+H]$^+$: 212.1.

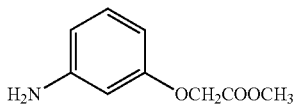

Synthesis of Methyl 2-(3-aminophenoxy)acetate (18b)

Pd/C (10% Pd basis, 565 mg) was added to a solution of 18b' (1.85 g, 8.8 mmol) in 1:1 THF:MeOH (50 mL). The reaction stirred under hydrogen atmosphere for 20 h. The mixture was then filtered through celite and purified by column chromatography (Hexanes/EtOAc) to provide the title compound as a pale white solid (1.5 g, 92% yield). $^1$H NMR (400 MHz, DMSO-$d_6$) δ 6.90 (t, J=8.0 Hz, 1H), 6.19 (d, J=7.9 Hz, 1H), 6.11 (s, 1H), 6.05 (d, J=8.1 Hz, 1H), 5.07 (s, 2H), 4.65 (s, 2H), 3.69 (s, 3H). $^{13}$C NMR (101 MHz, DMSO-$d_6$) δ 169.45, 158.62, 150.03, 129.58, 107.53, 101.65, 100.01, 64.31, 51.71. ESI-MS m/z: [M+H]$^+$: 182.1.

Scheme 5. Synthesis of 18c.$^a$

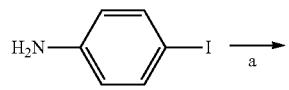

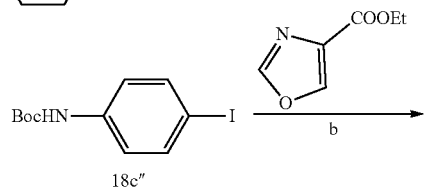

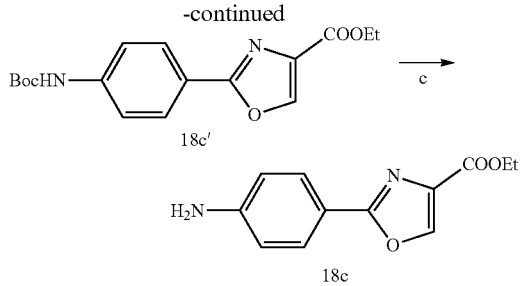

$^a$Reagents and Conditions: (a) Boc$_2$O, Et$_3$N, iPrOH, r.t., 14 h; (b) 10 mol % Pd(OAc)$_2$, 20 mol % JohnPhos, Cs$_2$CO$_3$, dioxane, 110° C., 19 h; (c) TFA, DCM, 0° C. to r.t., 30 min.

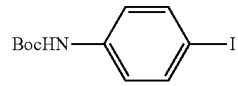 [SMILES: CC(C)(C)OC(=O)Nc1ccc(I)cc1]

Synthesis of N-Boc-4-iodoaniline (18c")

Triethylamine (1.27 mL, 9.1 mmol) was added to a mixture of 4-iodoaniline (1.0 g, 4.6 mmol) and Boc anhydride (997 mg, 4.6 mmol) in isopropanol (23 mL, 0.2 M). The reaction was stirred at room temperature for 14 h and then concentrated under reduced pressure. The crude mixture was purified by column chromatography (Hexanes/EtOAc) to provide the title product as a pale yellow solid (908 mg, 62% yield). $^1$H NMR (400 MHz, Chloroform-d) δ 7.57 (d, J=8.8 Hz, 2H), 7.14 (d, J=8.7 Hz, 2H), 6.43 (s, 1H), 1.51 (s, 9H). $^{13}$C NMR (101 MHz, Chloroform-d) δ 152.55, 138.31, 137.96, 120.49, 85.86, 81.07, 28.45. HRMS (ESI): calc. for [IC$_6$H$_4$NHCO$_2$H+H]+263.9521 found 263.9529.

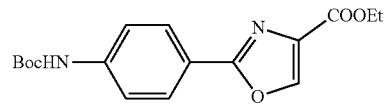 [SMILES: CCOC(=O)c1coc(-c2ccc(NC(=O)OC(C)(C)C)cc2)n1]

Synthesis of Ethyl 2-(4-((tert-butoxycarbonyl) amino)phenyl)oxazole-4-carboxylate (18c')

Ethyl 4-oxazole carboxylate (200 mg, 1.4 mmol), was combined with 18c" (452 mg, 1.4 mmol), palladium acetate (32 mg, 0.14 mmol), JohnPhos (85 mg, 0.28 mmol) and cesium carbonate (923 mg, 2.8 mmol) in dry dioxane (4 mL, 0.35 M). The reaction was sealed under N2 atm and heated at 110° C. for 19 h. The crude mixture was filtered through celite and purified by column chromatography (Hexanes/EtOAc) to provide the title product as a light yellow solid (141 mg, 30% yield). $^1$H NMR (500 MHz, Chloroform-d) δ 8.23 (s, 1H), 8.04 (d, J=8.6 Hz, 2H), 7.48 (d, J=8.4 Hz, 2H), 6.67 (s, 1H), 4.42 (q, J=7.1 Hz, 2H), 1.52 (s, 9H), 1.40 (t, J=7.1 Hz, 3H). ESI-MS m/z: [M+H]$^+$: 333.1.

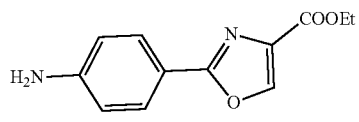 [SMILES: CCOC(=O)c1coc(-c2ccc(N)cc2)n1]

Synthesis of Ethyl 2-(4-aminophenyl)oxazole-4-carboxylate (18c)

Compound 18c' (101 mg, 0.3 mmol) was dissolved in anhydrous dichloromethane (0.8 mL, 0.38 M). The reaction mixture was cooled to 0° C. and trifluoroacetic acid (0.79 mL, 10.3 mmol) was added dropwise under vigorous stirring. The reaction was warmed to room temperature and stirred for 30 min. The pH was then adjusted to ~8 by adding sodium bicarbonate at 0° C. and the mixture was extracted with ethyl acetate. The combined organic phases were dried over anhydrous sodium sulfate, filtered, and concentrated to provide the product as a grey, shiny solid (71 mg, 100% yield). $^1$H NMR (400 MHz, Chloroform-d) δ 8.19 (s, 1H), 7.91 (d, J=8.5 Hz, 2H), 6.71 (d, J=8.4 Hz, 2H), 4.42 (q, J=7.1 Hz, 2H), 3.98 (s, 2H), 1.40 (t, J=7.1 Hz, 3H). $^{13}$C NMR (101 MHz, Chloroform-d) δ 163.26, 161.83, 149.31, 142.92, 134.48, 128.76, 116.76, 114.70, 61.32, 14.51. ESI-MS m/z: [M+H]$^+$: 233.1.

the reaction was cooled to room temperature, diluted with 5% Na$_2$S$_2$O$_3$ (200 mL) and stirred for 30 min. The resulting suspension was extracted with ethyl acetate (4×100 mL), washed with brine, and dried over sodium sulfate. Purification by column chromatography (Hexanes/EtOAc) followed by recrystallization from hot methanol afforded the title product as a yellow solid (277 mg, 12% yield over 2 steps). $^1$H NMR (400 MHz, DMSO-d$_6$) δ 7.71 (d, J=8.7 Hz, 2H), 6.69 (d, J=8.7 Hz, 2H), 6.13 (s, 2H), 4.42 (q, J=7.1 Hz, 2H), 1.35 (t, J=7.1 Hz, 3H). $^{13}$C NMR (151 MHz DMSO-d$_6$) δ 166.34, 155.26, 154.21, 153.26, 128.84, 113.62, 108.32, 62.65, 13.92. ESI-MS m/z: [M+H]$^+$: 234.1.

Scheme 7. Synthesis of phenyl carbamates 19a, c-j$^a$

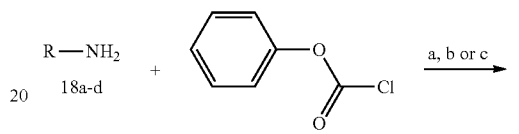

18a: R = p-PH-OCH$_2$COOCH$_3$
18b: R = m-Ph-OCH$_2$COOCH$_3$
18c: R = ethyl 2-(p-phenyl)oxazole-4-carboxylate
18d: R = ethyl 5-(p-phenyl)-1,3,4-oxadiazole-2-carboxylate Scheme 6. Synthesis of 18d.$^a$

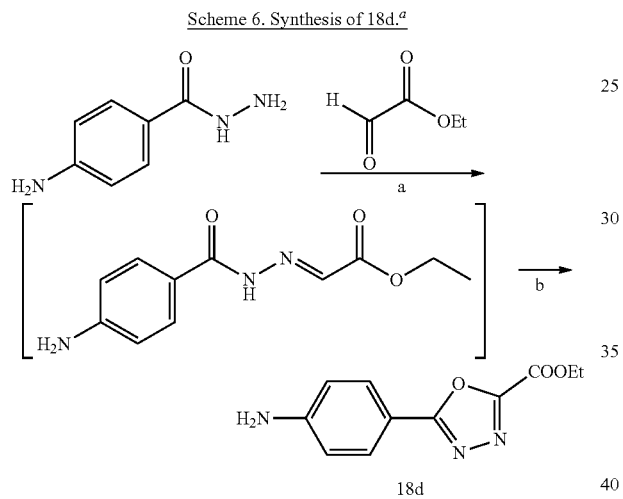

$^a$Reagents and conditions:
(a) EtOH, reflux, 10 min;
(b) K$_2$CO$_3$, I$_2$, DMSO, 100° C., 40 min.

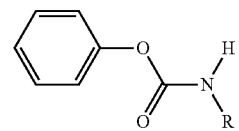

19a: R = Ph
19c: R = 2-pyridinyl
19d: R = 3-pyridinyl
19e: R = p-Ph-OCH$_2$COOCH$_3$
19f: R = m-Ph-OCH$_2$COOCH$_3$
19g: R = ethyl 2-(p-phenyl)oxazole-4-carboxylate
19h: R = methyl 5-(p-phenyl)furan-2-carboxylate
19i: R = ethyl 5-(p-phenyl)-1,3,4-oxadizaole-2-carboxylate
19j: R = p-[(E)-cinnamic acid]

$^a$Reagents and conditions:
(a) NaHCO$_3$, H$_2$O/THF, 0° C., 40 min-1 h;
(b) NaHCO$_3$, H$_2$O/THF, 0° C. to r.t., 45 h;
(c) pyridine, MeCN, r.t., 2.5 h.

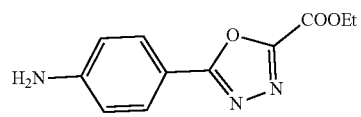 [SMILES: CCOC(=O)c1nnc(-c2ccc(N)cc2)o1]

Synthesis of Ethyl 5-(4-aminophenyl)-1,3,4-oxadiazole-2-carboxylate (18d)

Ethyl glyoxylate (1.98 mL (50% solution in THF), 10 mmol) in ethanol (100 mL, 0.1 M) was heated to reflux for 5 min. 4-aminobenzoic hydrazide (1.5 g, 10 mmol) was then added portion wise. After refluxing for 10-15 min, condensation was completed, as indicated by MS. The reaction mixture was concentrated under reduced pressure and the residue was dissolved in dimethylsulfoxide (50 mL). Potassium carbonate (4.2 g, 30 mmol) and iodine (3.0 g, 12 mmol) were added and then the reaction mixture was heated at 100° C. At 40 min MS indicated completion of the cyclization and

General Procedure A: Synthesis of Phenyl Carbamates 19a, e-j

The appropriate aromatic amine (1.0 eq.) was suspended in a mixture of tetrahydrofuran (2 M) and water (1 M) containing sodium bicarbonate (1.2 eq. for all except 19j; 2.2 eq. for 19j). The mixture was cooled to 0° C. and a solution of phenyl chloroformate (1.05 eq.) in tetrahydrofuran (1 M) was slowly added to the reaction mixture. The reaction was stirred at 0° C. unless otherwise stated until completion as determined by TLC and MS. Then the reaction mixture was diluted with ethyl acetate (20 mL), washed with water (3×5 mL) and brine (2×5 mL), and dried over sodium sulfate. The solvent was evaporated under reduced pressure to afford the corresponding phenyl carbamate without further purification, unless otherwise stated.

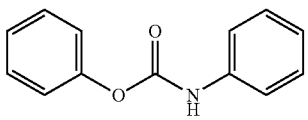 [SMILES: O=C(Nc1ccccc1)Oc1ccccc1]

Phenyl phenylcarbamate (19a). Aniline (0.3 mL, 3.3 mmol) was stirred for 40 min with phenyl chloroformate (0.44 mL, 3.5 mmol) as described in General Procedure A, to afford the title compound as a white solid (700 mg, 99% yield). $^1$H NMR (400 MHz, DMSO-$d_6$) δ 10.21 (s, 1H), 7.51 (d, J=7.7 Hz, 2H), 7.43 (t, J=7.8 Hz, 2H), 7.32 (t, J=7.8 Hz, 2H), 7.27 (d, J=7.5 Hz, 1H), 7.23 (d, J=8.4 Hz, 2H), 7.05 (t, J=7.3 Hz, 1H).$^{13}$C NMR (101 MHz, DMSO-$d_6$) δ 151.68, 150.50, 138.61, 129.41, 128.87, 125.41, 122.96, 121.95, 118.44. ESI-MS m/z: [M+H]$^+$: 214.1.

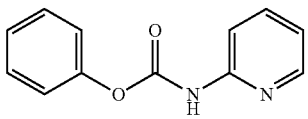 [SMILES: O=C(Nc1ccccn1)Oc1ccccc1]

Phenyl pyridin-2-ylcarbamate (19c). 2-amino pyridine (311 mg, 3.3 mmol) was combined with phenyl chloroformate (3.1 mL, 24.4 mmol) in the presence of sodium bicarbonate (2.3 g, 27.8 mmol), using the solvent composition mentioned in General Procedure A. The reaction was stirred at 0° C. for 2-3 h and then was warmed to r.t. and stirred 45 h. The reaction was extracted as in Procedure A, and subsequently purified by column chromatography (Hexanes/EtOAc) to afford the title product as a white solid (94 mg, 13% yield). $^1$H NMR (600 MHz, DMSO-$d_6$) δ 10.71 (s, 1H), 8.33-8.31 (m, 1H), 7.83-7.77 (m, 2H), 7.46-7.41 (m, 2H), 7.29-7.25 (m, 1H), 7.24-7.20 (m, 2H), 7.12-7.08 (m, 1H). ESI-MS m/z: [M+H]$^+$: 215.1.

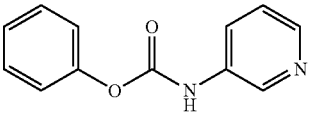 [SMILES: O=C(Nc1cccnc1)Oc1ccccc1]

Phenyl pyridin-3-ylcarbamate (19d).[8] 3-amino pyridine (941 mg, 10 mmol) was dissolved in mixture of acetonitrile (8 mL) and pyridine (0.9 mL, 11.0 mmol). The reaction mixture was cooled to 0° C., phenyl chloroformate (1.25 mL, 10.0 mmol) was added, and the reaction was warmed to room temperature and stirred for 2.5 h. Upon quenching with water (40 mL), the title product precipitated out of the reaction mixture, and was washed with water and dried under vacuum to give a reddish-brown solid (1.7 g, 79% yield). $^1$H NMR (400 MHz, DMSO-$d_6$) δ 10.47 (s, 1H), 8.69 (d, J=2.4 Hz, 1H), 8.27 (dd, J=4.7, 1.3 Hz, 1H), 7.93 (d, J=8.7 Hz, 1H), 7.44 (t, J=7.9 Hz, 2H), 7.37 (dd, J=8.3, 4.7 Hz, 1H), 7.31-7.21 (m, 3H).$^{13}$C NMR (101 MHz, DMSO-$d_6$) δ 151.87, 150.37, 144.04, 140.28, 135.42, 129.48, 125.64, 125.34, 123.74, 121.94. ESI-MS m/z: [M+H]$^+$: 215.1.

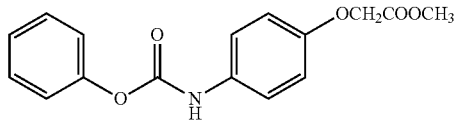

Methyl 2-(4-((phenoxycarbonyl)amino)phenoxy)acetate (19e). Amine 18a (600 mg, 3.3 mmol) reacted with phenyl chloroformate (0.44 mL, 3.5 mmol) for 40 min to afford a white, crystalline solid (919 mg, 92% yield). $^1$H NMR (400 MHz, DMSO-$d_6$) δ 10.08 (s, 1H), 7.46-7.36 (m, 4H), 7.25 (t, J=7.4 Hz, 1H), 7.21 (d, J=7.6 Hz, 2H), 6.91 (d, J=9.1 Hz, 2H), 4.75 (s, 2H), 3.69 (s, 3H). $^{13}$C NMR (151 MHz, DMSO-$d_6$) δ 169.30, 153.41, 151.81, 150.59, 132.26, 129.40, 125.34, 121.95, 119.95, 114.82, 64.80, 51.78. ESI-MS m/z: [M+H]$^+$: 302.1.

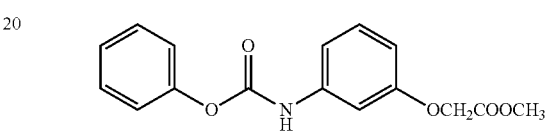

Methyl 2-(3-((phenoxycarbonyl)amino)phenoxy)acetate (19f). Amine 18b (600 mg, 3.3 mmol) reacted with phenyl chloroformate (0.44 mL, 3.5 mmol) for 40 min to afford a white solid (895 mg, 90% yield). $^1$HNMR (400 MHz, DMSO-$d_6$) δ 10.26 (s, 1H), 7.43 (t, J=7.7 Hz, 2H), 7.29-7.19 (m, 3H), 7.18-7.10 (m, 2H), 6.78-6.72 (m, 1H), 6.61 (dd, J=8.2, 2.3 Hz, 1H), 4.75 (s, 2H), 3.69 (s, 3H). ESI-MS m/z: [M+H]$^+$: 302.1.

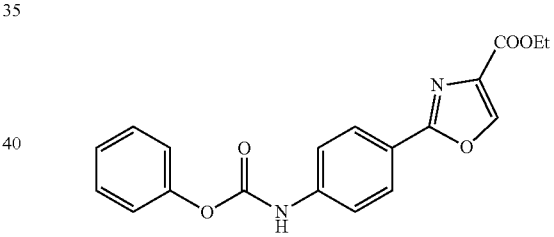

Ethyl 2-(4-((phenoxycarbonyl)amino)phenyl)oxazole-4-carboxylate (19g). Amine 18c (71 mg, 0.31 mmol) reacted with phenyl chloroformate (42 μL, 0.33 mmol) for 1 h to provide the title product as a light brown solid (99 mg, 91% yield). $^1$H NMR (600 MHz, DMSO-$d_6$) δ 10.62 (s, 1H), 8.90 (s, 1H), 7.99 (d, J=8.8 Hz, 2H), 7.70 (d, J=8.7 Hz, 2H), 7.45 (t, J=7.9 Hz, 2H), 7.30-7.24 (m, 3H), 4.31 (q, J=7.1 Hz, 2H), 1.31 (t, J=7.1 Hz, 3H). $^{13}$C NMR (151 MHz, DMSO-$d_6$) δ 161.25, 160.75, 151.58, 150.33, 145.32, 141.51, 133.60, 129.49, 127.44, 125.64, 121.94, 120.44, 118.51, 60.64, 14.20. ESI-MS m/z: [M+H]$^+$: 353.1.

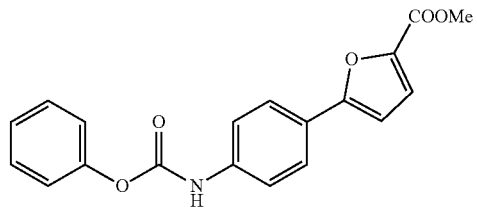 [SMILES: COC(=O)c1ccc(-c2ccc(NC(=O)Oc3ccccc3)cc2)o1]

Methyl 5-(4-((phenoxycarbonyl)amino)phenyl)furan-2-carboxylate (19h). Methyl 5-(4-aminophenyl)furan-2-carboxylate (719 mg, 3.3 mmol) reacted with phenyl chloroformate (0.44 mL, 3.5 mmol) for 1 h to afford the title product as a cream white solid (1.09 g, 97% yield). $^1$H NMR (600 MHz, DMSO-$d_6$) δ 10.48 (s, 1H), 7.79 (d, J=8.7 Hz, 2H), 7.63 (d, J=8.6 Hz, 2H), 7.44 (t, J=7.9 Hz, 2H), 7.40 (d, J=3.6 Hz, 1H), 7.27 (t, J=7.4 Hz, 1H), 7.25 (d, J=7.7 Hz, 2H), 7.07 (d, J=3.6 Hz, 1H), 3.83 (s, 3H). $^{13}$C NMR (151 MHz, DMSO-$d_6$) δ 158.31, 156.82, 151.62, 150.40, 142.51, 139.53, 129.46, 125.56, 125.42, 123.66, 121.96, 120.71, 118.66, 107.06, 51.76. ESI-MS m/z: [M+H]$^+$: 338.1.

Ethyl 5-(4-((phenoxycarbonyl)amino)phenyl)-1,3,4-oxadiazole-2-carboxylate (19i). Amine 18d (200 mg, 0.86 mmol) was reacted with phenyl chloroformate (115 μL, 0.91 mmol) for 50 min. The crude mixture was processed according to Procedure A. The product was further purified by column chromatography (Hexanes/EtOAc) to afford the title product as a yellow solid (117 mg, 39% yield). $^1$H NMR (600 MHz, DMSO-$d_6$) δ 10.74 (s, 1H), 8.05 (d, J=8.7 Hz, 2H), 7.77 (d, J=8.7 Hz, 2H), 7.45 (t, J=7.9 Hz, 2H), 7.28 (dd, J=16.7, 7.9 Hz, 3H), 4.45 (q, J=7.1 Hz, 2H), 1.37 (t, J=7.1 Hz, 3H). $^{13}$C NMR (151 MHz, DMSO-$d_6$) δ 165.66, 156.61, 154.51, 152.01, 150.70, 143.31, 129.94, 128.82, 126.14, 122.36, 119.12, 117.08, 63.30, 14.33. ESI-MS m/z: [M+H]$^+$: 354.4.

(E)-3-(4-((phenoxycarbonyl)amino)phenyl)acrylic acid (19j). (E)-4-amino cinnamic acid (540 mg, 3.3 mmol) was reacted with phenyl chloroformate (0.44 mL, 3.5 mmol) in the presence of 2.2 eq. sodium bicarbonate (612 mg, 7.3 mmol), for 1 h. The reaction mixture was acidified to pH 4, followed by an extraction workup, as described in Procedure A. The product was further purified by column chromatography (DCM/MeCN) to afford the title compound as a white solid (500 mg, 53% yield). $^1$H NMR (600 MHz, DMSO-$d_6$) δ 12.29 (s, 1H), 10.47 (s, 1H), 7.66 (d, J=8.7 Hz, 2H), 7.58-7.51 (m, 3H), 7.44 (t, J=7.9 Hz, 2H), 7.27 (t, J=7.6 Hz, 1H), 7.24 (d, J=7.6 Hz, 2H), 6.43 (d, J=16.0 Hz, 1H). $^{13}$C NMR (151 MHz, DMSO-$d_6$) δ 167.73, 151.56, 150.37, 143.53, 140.51, 129.47, 129.21, 128.85, 125.58, 121.96, 118.32, 117.40. ESI-MS m/z: [M+H]$^+$: 284.0.

Scheme 8. Synthesis of 2.$^a$ $^a$Reagents and conditions: (a) Cs$_2$CO$_3$, DMF, r.t., 16 h.

Synthesis of 4-((5-amino-1-(2,6-difluorobenzyl)-1H-1,2,4-triazol-3-yl)amino)benzenesulfonamide (2)

Compound 17a (150 mg, 0.6 mmol), 2-(bromomethyl)-1,3-difluorobenzene (75 μL, 0.6 mmol), and Cs$_2$CO$_3$ (192 mg, 0.6 mmol) were dissolved in dimethylformamide (2.4 mL, 0.25 M). The reaction was stirred 16 h at room temperature. The solvent was then evaporated and the residue purified by flash chromatography (DCM/MeOH) to afford 2 (54 mg, 24% yield). Purity 97%. $^1$H NMR (600 MHz, DMSO-$d_6$) δ 9.24 (s, 1H), 7.56 (d, J=8.9 Hz, 2H), 7.49 (d, J=8.9 Hz, 2H), 7.46-7.40 (m, 1H), 7.12 (t, J=7.9 Hz, 2H), 7.02 (s, 2H), 6.46 (s, 2H), 5.08 (s, 2H). $^{13}$C NMR (151 MHz, DMSO-$d_6$) δ 160.99 (dd, J=248.7, 7.9 Hz), 156.55, 154.20, 145.26, 133.28, 130.64 (t, J=10.3 Hz), 126.64, 114.56, 112.38 (t, J=19.2 Hz), 111.62 (dd, J=20.6, 4.7 Hz), 37.21 (t, J=3.4 Hz). HRMS (ESI): calc. for [M+H]$^+$ C$_{15}$H$_{15}$F$_2$N$_6$O$_2$S 381.0945 found 381.0956.

Scheme 9. Synthesis of compounds 3-4, 6-15.[a]

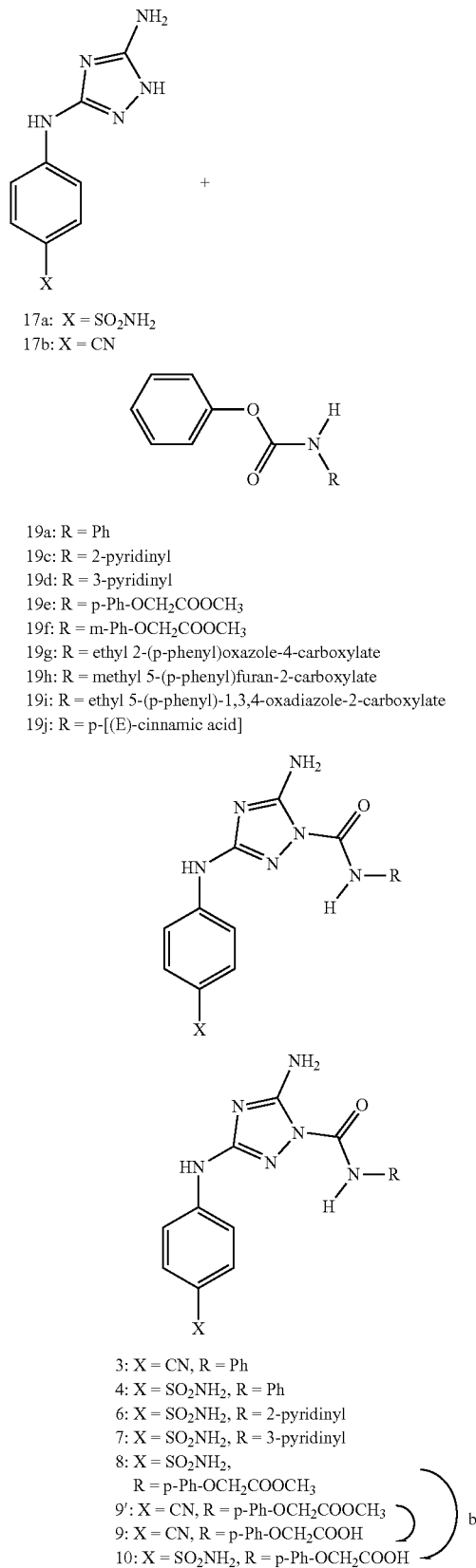

17a: X = SO₂NH₂
17b: X = CN

19a: R = Ph
19c: R = 2-pyridinyl
19d: R = 3-pyridinyl
19e: R = p-Ph-OCH₂COOCH₃
19f: R = m-Ph-OCH₂COOCH₃
19g: R = ethyl 2-(p-phenyl)oxazole-4-carboxylate
19h: R = methyl 5-(p-phenyl)furan-2-carboxylate
19i: R = ethyl 5-(p-phenyl)-1,3,4-oxadiazole-2-carboxylate
19j: R = p-[(E)-cinnamic acid]

3: X = CN, R = Ph
4: X = SO₂NH₂, R = Ph
6: X = SO₂NH₂, R = 2-pyridinyl
7: X = SO₂NH₂, R = 3-pyridinyl
8: X = SO₂NH₂, R = p-Ph-OCH₂COOCH₃
9': X = CN, R = p-Ph-OCH₂COOCH₃ ⎫ b
9: X = CN, R = p-Ph-OCH₂COOH ⎭
10: X = SO₂NH₂, R = p-Ph-OCH₂COOH
11': X = CN, R = m-Ph-OCH₂COOCH₃ ⎫ b
11: X = CN, R = m-Ph-OCH₂COOH ⎭
12': X = SO₂NH₂, R = ethyl 2-(p-phenyl)oxazole-4-carboxylate ⎫ b
12: X = SO₂NH₂, R = 2-(p-phenyl)oxazole-4-carboxylic acid ⎭
13': X = SO₂NH₂, R = methyl 5-(p-phenyl)furan-2-carboxylate ⎫ b
13: X = SO₂NH₂, R = 5-(p-phenyl)furan-2-carboxylic acid ⎭
14': X = SO₂NH₂, R = ethyl 5-(p-phenyl)-1,3,4-oxadiazole-2-carboxylate ⎫ b
14: X = SO₂NH₂, R = 5-(p-phenyl)-1,3,4-oxadiazole-2-carboxylic acid ⎭
15: X = SO₂NH₂, R = p-[(E)-cinnamic acid]

[a]Reagents and conditions:
(a) Et₃N, dioxane, 90° C-110° C., 35 min-2.5 h.;
(b) Base, LiBr, MeCN, 2 vol % H₂O, r.t., 11-288 h.

General Procedure B: Synthesis of Ureas 3, 4, 6-8, 9', 11'-14', 15

The appropriate phenyl carbamate (1.0 eq.), was dissolved in dry dioxane (0.4 M for 15, 0.5 M for 3, 8, 12', 13', and 14'; 1 M for 4, 6, 7, 9', and 11'), triethylamine (1.0 eq. for all except 15; 2.0 eq. for 15) was added, and the mixture was heated at 90-100° C. for five minutes. In a separate vial, a mixture of 17a or 17b (1.0 eq.) and triethylamine (1.0 eq.) in dry dioxane (0.2 M for 15, 0.5 M for 3, 8, 12', 13', and 14'; 1 M for 4, 6, 7, 9', and 11') was sonicated at 80-100° C. for 5-10 min and was added to the reaction mixture dropwise. The reaction vial was sealed under N₂ atmosphere and the mixture stirred for 1-3 h at 90-110° C. (90° C. for 11'; 100° C. for 3-4, 6-7, 9', and 15; 110° C. for 8, 12', 13', and 14').

Workup A (3, 8, 9',11' 14'). The reaction mixture was diluted with ethyl acetate (50 mL), was washed with water (2×15 mL) and brine (1×15 mL). The organic layer was collected, dried over sodium sulfate and, concentrated under reduced pressure. The crude mixture was purified by column chromatography, (DCM/MeOH).

Workup B (7, 12', 13'). Solvent was evaporated under reduced pressure and the reaction mixture was purified directly by chromatography (DCM/MeOH).

Workup C (4, 6). Solvent was evaporated under reduced pressure and the crude mixture was triturated with ethyl acetate (3×10 mL). The combined organic phases were purified by column chromatography (DCM/MeOH).

General Procedure C: Hydrolysis of Esters 8, 9', 11'-14'

Esters 8, 9', 11'-14' were suspended in a mixture of acetonitrile with 2 vol % water. Base (DBN, 3.0 eq. for 8, 12'-14'; Et₃N, 3.0 eq. for 9', 11') and lithium bromide (10 eq.) were then added and the reaction was allowed to run at r.t. for the indicated time.

Workup D (9, 11). Solvent was evaporated and sat. NaHCO3 was added to the reaction residue. The mixture was washed with ethyl acetate and the aqueous phase was acidified to pH ~4. The precipitate was collected, washed with small amounts of ethyl acetate and water, and dried under vacuum to provide the desired product.

Workup E (10, 12-14). Solvent was evaporated and a small amount of water was added to the residue. The pH was adjusted to ~4 and the mixture was kept at low temperature for 6-12 h. The mixture was centrifuged, and the precipitate was dried and purified by column chromatography (DCM/MeOH). For 10 and 14 the product was further purified by triturating with methanol.

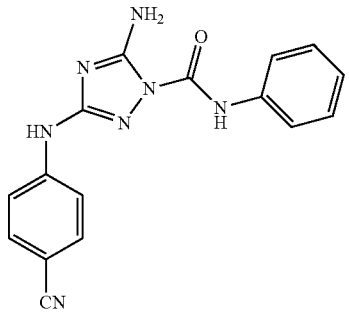 [SMILES: N#Cc1ccc(Nc2nc(N)n(C(=O)Nc3ccccc3)n2)cc1]

Synthesis of 5-amino-3((4(4-cyanophenyl)amino)-N-phenyl-1H-1,2,4-triazole-1-carboxamide (3)

Compound 19a (105 mg, 0.5 mmol) reacted with 17b (99 mg, 0.5 mmol) for 1.5 h to afford the title compound as a white, fluffy solid (45 mg, 29% yield). Purity: 99%. $^1$H NMR (600 MHz, DMSO-$d_6$) δ 9.87 (s, 1H), 9.64 (s, 1H), 7.85 (d, J=8.8 Hz, 2H), 7.67 (d, J=8.8 Hz, 2H), 7.66-7.63 (m, 2H), 7.45 (s, 2H), 7.42-7.37 (m, 2H), 7.18 (tt, J=7.3, 1.2 Hz, 1H). $^{13}$C NMR (151 MHz, DMSO-$d_6$) δ 156.38, 155.91, 149.08, 145.05, 137.06, 133.12, 128.65, 124.51, 121.84, 119.83, 116.99, 101.05. HRMS (ESI): calc. for [M+H]$^+$ $C_{16}H_{14}N_7O$ 320.1260 found 320.1245. [17b+H]$^+$201.0882 was also observed due to in-source fragmentation.

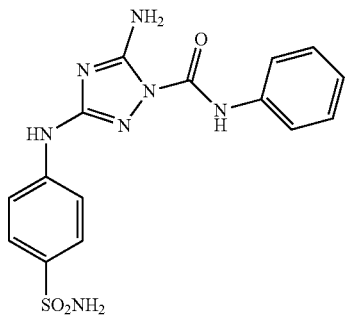 [SMILES: Nc1nc(Nc2ccc(S(N)(=O)=O)cc2)nn1C(=O)Nc1ccccc1]

Synthesis of 5-amino-N-phenyl-3((4(4-sulfamoylphenyl)amino)-1H-1,2,4-triazole-1-carboxamide (4)

Compound 19a (59 mg, 0.3 mmol) reacted with 17a (70 mg, 0.3 mmol) for 1 h to afford the title compound as a white, fluffy solid (39 mg, 38% yield). Purity: 99%. $^1$H NMR (600 MHz, DMSO-$d_6$) δ 9.68 (s, 1H), 9.59 (s, 1H), 7.82 (d, J=8.9 Hz, 2H), 7.71 (d, J=9.0 Hz, 2H), 7.65 (d, J=8.7 Hz, 2H), 7.46-7.37 (m, 4H), 7.20-7.16 (m, 1H), 7.14 (s, 2H). $^{13}$C NMR (151 MHz, DMSO-$d_6$) δ 156.69, 155.90, 149.14, 143.90, 137.10, 134.88, 128.70, 126.84, 124.54, 121.87, 116.24. HRMS (ESI): calc. for [M+H]$C_{15}H_{16}N_7O_3S$ 374.1035 found 374.1009. [17a+H]$^+$ 255.0645 was also observed due to in-source fragmentation.

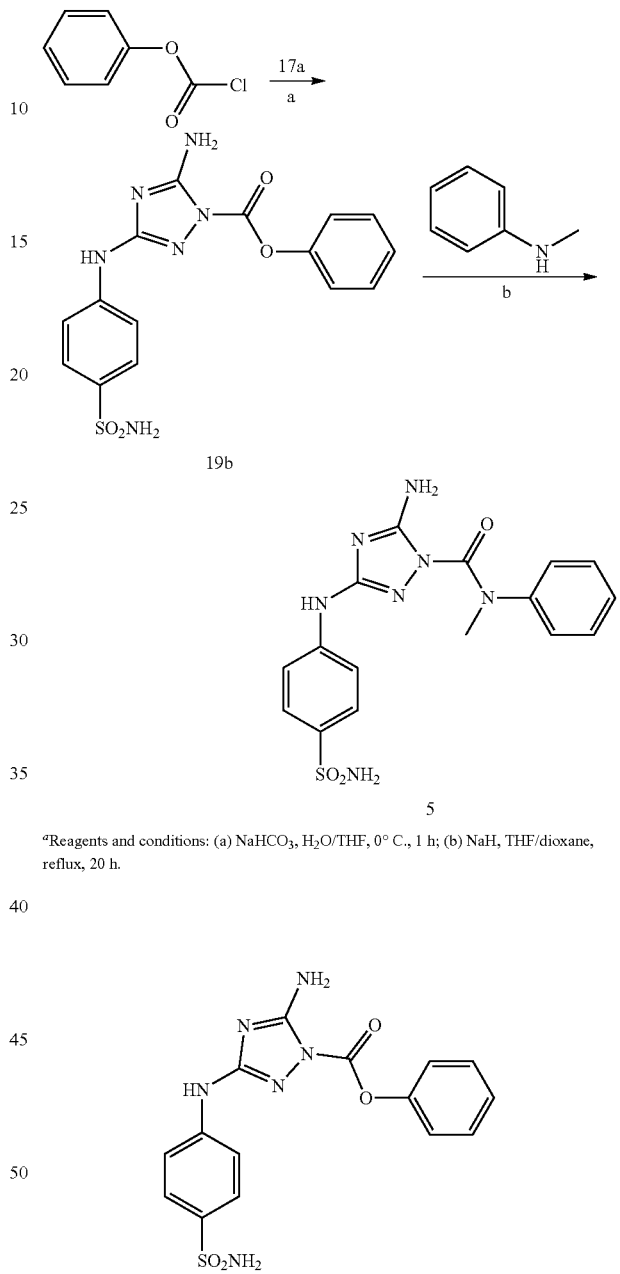

Scheme 10. Synthesis of compound 5$^a$ $^a$Reagents and conditions: (a) NaHCO$_3$, H$_2$O/THF, 0° C., 1 h; (b) NaH, THF/dioxane, reflux, 20 h.

Synthesis of Phenyl 5-amino-3((4(4-sulfamoylphenyl)amino)-1H-1,2,4-triazole-1-carboxylate (19b)

To a suspension of 17a (509 mg, 2.0 mmol) in tetrahydrofuran/water was added sodium bicarbonate (168 mg, 2.0 mmol). The mixture was cooled to 0° C. Phenyl chloroformate (0.25 mL, 2.0 mmol) was added, followed by additional sodium bicarbonate (168 mg, 2.0 mmol). The reaction was stirred at 0° C. for 1 h and the crude mixture was processed according to Procedure A. The product was further purified by column chromatography (DCM/MeOH) to afford the title product as a pale white solid (581 mg, 78% yield). ¹H NMR (600 MHz, DMSO-d₆) δ 9.78 (s, 1H), 7.69 (s, 4H), 7.57 (s, 2H), 7.52-7.48 (m, 2H), 7.41-7.34 (m, 3H), 7.14 (s, 2H). ¹³C NMR (151 MHz, DMSO-d₆) δ 158.11, 157.01, 149.91, 148.58, 143.93, 135.04, 129.70, 126.80, 126.61, 121.87, 115.89. ESI-MS m/z: [M+H]⁺: 375.0.

1H), 7.75-7.70 (m, 4H), 7.52 (s, 2H), 7.25-7.21 (m, 1H), 7.15 (s, 2H). ¹³C NMR (151 MHz, DMSO-d₆) δ 156.89, 155.90, 150.13, 148.34, 143.79, 138.61, 135.13, 126.81, 120.34, 116.16, 113.66, 109.56. HRMS (ESI): calc. for [M+H]C₁₄H₁₅N₈O₃S 375.0988 found 375.0410. [16a+H]⁺ 255.0290 was also observed due to in-source fragmentation.

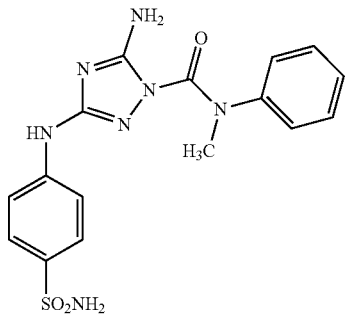 [SMILES: CN(C(=O)n1nc(Nc2ccc(S(N)(=O)=O)cc2)nc1N)c1ccccc1]

Synthesis of 5-amino-N-methyl-N-phenyl-3-((4-sulfamoylphenyl)amino)-1H-1,2,4-triazole-1-carboxamide (5)

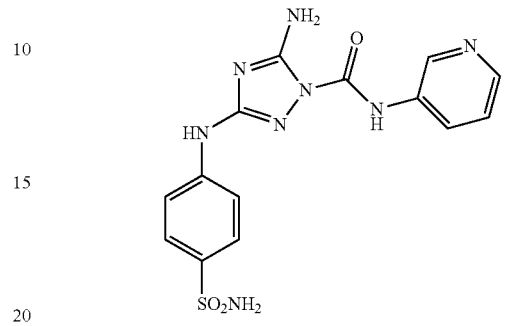

Synthesis of 5-amino-N-(pyridin-3-yl)-3((4-sulfamoylphenyl)amino)-1H-1,2,4-triazole-1-carboxamide (7)

N-methyl aniline (0.23 mL, 2.1 mmol) was dissolved in tetrahydrofuran (4.0 mL). Sodium hydride (51 mg, 2.1 mmol) was added at 0° C. and the mixture was allowed to stir for 1 h. Subsequently, this mixture was transferred dropwise to a separate vial containing 19b (400 mg, 1.1 mmol) in dioxane (2 mL) and the reaction was heated to reflux. After 20 h, solvent was evaporated and the crude mixture was purified by column chromatography (DCM/MeCN) to provide the product as a light brown solid (2 mg, Yield <1%). Purity: 94%. ¹H NMR (500 MHz, DMSO-d₆) δ 9.33 (s, 1H), 7.43 (dd, J=13.3, 7.9 Hz, 4H), 7.27 (dd, J=13.5, 7.5 Hz, 5H), 7.09 (s, 2H), 6.87 (d, J=8.5 Hz, 2H), 3.36 (s, 3H). ¹³C NMR (151 MHz, DMSO-d₆) δ 156.93, 155.37, 151.42, 145.19, 143.66, 134.31, 129.00, 126.30, 126.08, 125.79, 115.34, 29.62. HRMS (ESI): calc. for [M+H]C₁₆H₁₈N₇O₃S 388.1192 found 388.1156.

Compound 19d (59 mg, 0.3 mmol) was reacted with 17a (70 mg, 0.3 mmol) for 1 h to afford the title compound as a white, fluffy solid (20 mg, 20% yield). Purity: 100%. ¹H NMR (600 MHz, DMSO-d₆) δ 9.80 (s, 1H), 9.70 (s, 1H), 8.85 (d, J=2.5 Hz, 1H), 8.38 (dd, J=4.7, 1.4 Hz, 1H), 8.06 (ddd, J=8.3, 2.6, 1.5 Hz, 1H), 7.84-7.80 (m, 2H), 7.72-7.69 (m, 2H), 7.47-7.42 (m, 3H), 7.15 (s, 2H). ¹³C NMR (151 MHz, DMSO-d₆) δ 156.81, 155.91, 149.28, 145.35, 143.80, 143.55, 134.91, 133.94, 129.16, 126.77, 123.45, 116.21. HRMS (ESI): calc. for [M+H]⁺ C₁₄H₁₅N₈O₃S 375.0988 found 375.0970. [17a+H]⁺ 255.0662 was also observed due to in-source fragmentation.

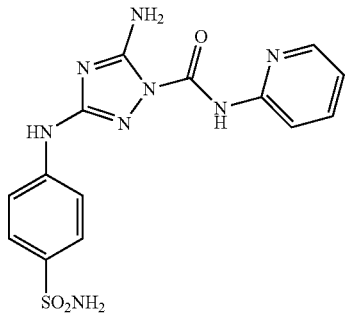 [SMILES: Nc1nc(Nc2ccc(S(N)(=O)=O)cc2)nn1C(=O)Nc1ccccn1]

Synthesis of 5-amino-N-(pyridin-2-yl)-3((4(4-sulfamoylphenyl)amino)-1H-1,2,4-triazole-1-carboxamide (6)

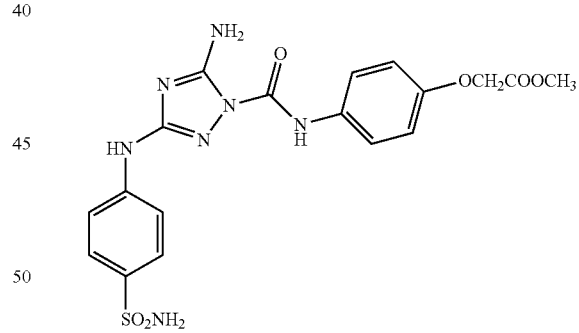

Synthesis of Methyl 2-(4-(5-amino-3((4-sulfamoylphenyl)amino)-1H-1,2,4-triazole-1-carboxamido)phenoxy)acetate(8)

Compound 19c (59 mg, 0.3 mmol) reacted with 17a (70 mg, 0.3 mmol) for 1 h, to afford the title compound as a white, fluffy solid (15 mg, 14% yield). Purity: 99%. ¹H NMR (600 MHz, DMSO-d₆) δ 9.76 (s, 1H), 9.42 (s, 1H), 8.41 (d, J=4.1 Hz, 1H), 7.95 (d, J=8.3 Hz, 1H), 7.92-7.88 (m, Compound 19e (331 mg, 1.1 mmol) reacted with 17a (280 mg, 1.1 mmol) for 1.5 h. The reaction was processed using Workup A with modified column chromatography (DCM/MeCN), to afford the title compound as a white, fluffy solid (209 mg, 41% yield). Purity: 98%. ¹H NMR (600 MHz, DMSO-d₆) δ 9.66 (s, 1H), 9.53 (s, 1H), 7.81 (d, J=8.8 Hz, 2H), 7.69 (d, J=8.7 Hz, 2H), 7.52 (d, J=9.0 Hz, 2H), 7.38 (s, 2H), 7.14 (s, 2H), 6.97 (d, J=9.0 Hz, 2H), 4.81 (s, 2H), 3.71 (s, 3H). ¹³C NMR (151 MHz, DMSO-d₆) δ 169.26, 156.61, 155.80, 154.60, 149.31, 143.88, 134.79, 130.47, 126.77, 123.89, 116.16, 114.49, 64.77, 51.81. HRMS (ESI): calc. for [M+H]⁺ C$_{18}$H$_{20}$N$_7$O$_6$S 462.1196 found 462.1172. [17a+H]⁺ 255.0659 was also observed due to in-source fragmentation.

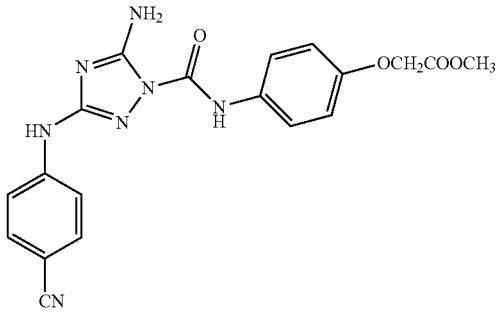

Synthesis Methyl 2-(4-(5-amino-3((4-cyanophenyl)amino)-1H-1,2,4-triazole-1-carboxamido)phenoxy)acetate(9')

Compound 19e (151 mg, 0.5 mmol) reacted with 17b (100 mg, 0.5 mmol) for 35 min to afford the title compound as a white fluffy solid. (65 mg, 32% yield). ¹H NMR (400 MHz, DMSO-d$_6$) δ 9.84 (s, 1H), 9.57 (s, 1H), 7.84 (d, J=8.8 Hz, 2H), 7.65 (d, J=8.9 Hz, 2H), 7.51 (d, J=9.1 Hz, 2H), 7.40 (s, 2H), 6.97 (d, J=9.1 Hz, 2H), 4.80 (s, 2H), 3.71 (s, 3H). ¹³C NMR (151 MHz, DMSO-d$_6$) δ 169.26, 156.34, 155.84, 154.62, 149.28, 145.07, 133.10, 130.45, 123.89, 119.85, 116.98, 114.49, 101.00, 64.76, 51.82. ESI-MS m/z: [M+H]⁺: 408.1.

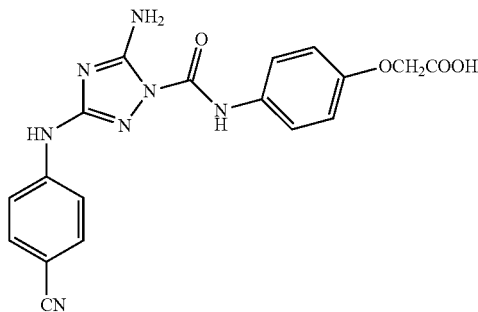

Synthesis of 2-(4-(5-amino-3((4-cyanophenyl)amino)-1H-1,2,4-triazole-1-carboxamido)phenoxy)acetic acid (9)

Compound 9' (14 mg, 35 μmol) was hydrolyzed according to the general procedure C (MeCN 0.2 M, Et$_3$N, 11 h) and the reaction was processed using Workup D to afford the title compound as a white solid (10 mg, 70% yield). Purity: 97%. ¹H NMR (600 MHz, DMSO-d$_6$) δ 12.94 (bs, 1H), 9.86 (s, 1H), 9.57 (s, 1H), 7.85 (d, J=8.5 Hz, 2H), 7.65 (d, J=8.5 Hz, 2H), 7.51 (d, J=8.7 Hz, 2H), 7.42 (s, 2H), 6.94 (d, J=8.7 Hz, 2H), 4.68 (s, 2H). ¹³C NMR (151 MHz, DMSO-d$_6$) δ 170.25, 156.38, 155.88, 154.85, 149.33, 145.11, 133.14, 130.25, 123.91, 119.90, 117.03, 114.45, 101.04, 64.73. HRMS (ESI): calc. for [M+H]⁺ C$_{18}$H$_{16}$N$_7$O$_4$ 394.1264 found 394.1285.

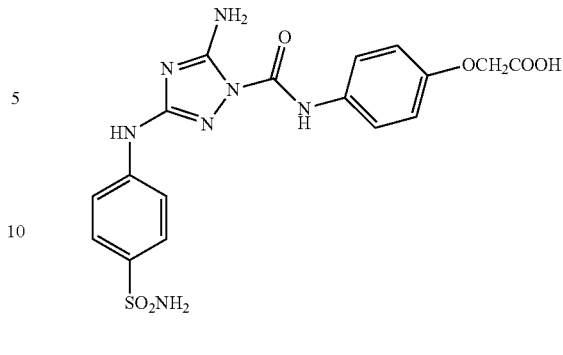

Synthesis of 2-(4-(5-amino-3((4-sulfamoylphenyl)amino)-1H-1,2,4-triazole-1-carboxamido)phenoxy)acetic acid (10)

Compound 8 (187 mg, 405 μmol) was hydrolyzed according to general procedure C (MeCN 0.03 M, DBN, 38 h) and the reaction was processed using Workup E to afford the title compound as a white solid (15.1 mg, 8% yield). Purity: 95%. ¹H NMR (600 MHz, DMSO-d$_6$) δ 12.95 (bs, 1H), 9.66 (s, 1H), 9.52 (s, 1H), 7.81 (d, J=8.8 Hz, 2H), 7.69 (d, J=8.8 Hz, 2H), 7.50 (d, J=8.9 Hz, 2H), 7.38 (s, 2H), 7.14 (s, 2H), 6.93 (d, J=8.9 Hz, 2H), 4.65 (s, 2H). ¹³C NMR (151 MHz, DMSO-d$_6$) δ 170.25, 156.60, 155.80, 154.89, 149.32, 143.89, 134.78, 130.17, 126.78, 123.85, 116.16, 114.40, 64.90. HRMS (ESI): calc. for [M+H]⁺ C$_{17}$H$_{18}$N$_7$O$_6$S 448.1039 found 448.1033. [17a+H]⁺ 255.0668 was also observed due to in-source fragmentation.

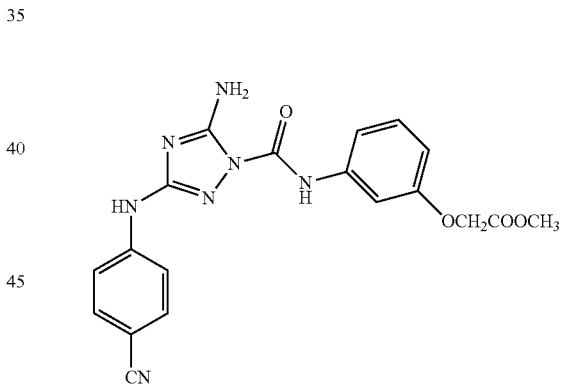

Synthesis of Methyl 2-(3-(5-amino-3((4-cyanophenyl)amino)-1H-1,2,4-triazole-1-carboxamido)phenoxy)acetate(11')

Compound 19f (151 mg, 0.5 mmol) was reacted with 17b (100 mg, 0.5 mmol) for 50 min to afford the title compound as a white fluffy solid. (59 mg, 29% yield). ¹H NMR (600 MHz, DMSO-d$_6$) δ 9.87 (s, 1H), 9.61 (s, 1H), 7.83 (d, J=8.9 Hz, 2H), 7.67 (d, J=9.0 Hz, 2H), 7.46 (s, 2H), 7.33-7.27 (m, 3H), 6.74 (dt, J=7.0, 2.3 Hz, 1H), 4.80 (s, 2H), 3.72 (s, 3H). ¹³C NMR (151 MHz, DMSO-d$_6$) δ 169.14, 157.78, 156.40, 155.92, 148.93, 145.03, 138.35, 133.14, 129.50, 119.83, 117.00, 114.41, 110.05, 108.17, 101.08, 64.59, 51.87. ESI-MS m/z: [M+H]⁺: 408.1.

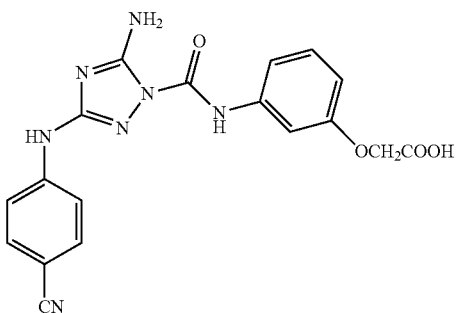

Synthesis of 2-(3-(5-amino-3((4-cyanophenyl)amino)-1H-1,2,4-triazole-1-carboxamido)phenoxy)acetic acid (11)

Compound 11' (16 mg, 39 µmol) was hydrolyzed according to General Procedure C (MeCN 0.2 M, Et$_3$N, 21 h) and the reaction was processed using Workup D to afford the title compound as a white solid (5 mg, 35% yield). Purity: 91%. $^1$H NMR (600 MHz, DMSO-d$_6$) δ 12.99 (bs, 1H), 9.87 (s, 1H), 9.60 (s, 1H), 7.83 (d, J=8.5 Hz, 2H), 7.67 (d, J=8.7 Hz, 2H), 7.45 (s, 2H), 7.32-7.27 (m, 3H), 6.74-6.69 (m, 1H), 4.67 (s, 2H). $^{13}$C NMR (151 MHz, DMSO-d$_6$) δ 170.08, 157.99, 156.41, 155.92, 148.93, 145.05, 138.32, 133.16, 129.45, 119.84, 117.00, 114.17, 110.12, 108.01, 101.08, 64.53. HRMS (ESI): calc. for [M+H]$^+$ C$_{18}$H$_{16}$N$_7$O$_4$ 394.1264 found 394.1337.

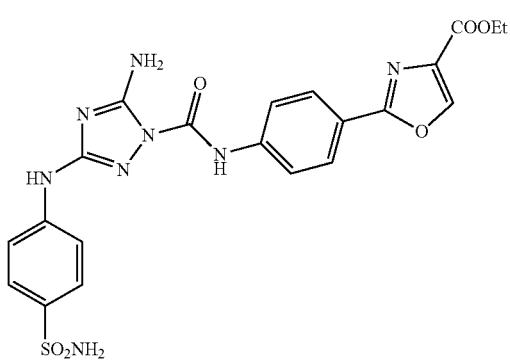 [SMILES: CCOC(=O)c1coc(-c2ccc(NC(=O)n3nc(Nc4ccc(S(N)(=O)=O)cc4)nc3N)cc2)n1]

Synthesis of Ethyl 2-(4-(5-amino-3((4-sulfamoylphenyl)amino)-1H-1,2,4-triazole-1-carboxamido)phenyl)oxazole-4-carboxylate (12')

Compound 19g (60 mg, 0.2 mmol) reacted with 17a (43 mg, 0.2 mmol) for 50 min. The reaction was processed using Workup B with modified column chromatography (DCM/MeCN) to provide the title compound as a white solid. (21 mg, 25% yield). $^1$H NMR (600 MHz, DMSO-d$_6$) δ 9.86 (s, 1H), 9.72 (s, 1H), 8.94 (s, 1H), 8.04 (d, J=8.7 Hz, 2H), 7.93 (d, J=8.7 Hz, 2H), 7.84 (d, J=8.8 Hz, 2H), 7.72 (d, J=8.9 Hz, 2H), 7.49 (s, 2H), 7.16 (s, 2H), 4.33 (q, J=7.1 Hz, 2H), 1.32 (t, J=7.1 Hz, 3H). $^{13}$C NMR (151 MHz, DMSO-d$_6$) δ 161.16, 160.74, 156.77, 155.95, 148.87, 145.51, 143.79, 140.15, 134.96, 133.68, 127.03, 126.79, 121.57, 121.39, 116.26, 60.68, 14.21. ESI-MS m/z: [M+H]$^+$: 513.1.

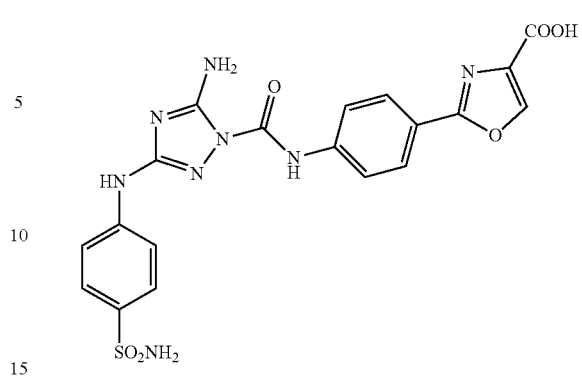

Synthesis of 2-(4-(5-amino-3((4-sulfamoylphenyl)amino)-1H-1,2,4-triazole-1-carboxamido)phenyl)oxazole-4-carboxylic acid (12)

Compound 12' (14 mg, 27 µmol) was hydrolyzed according to General Procedure C (MeCN 0.14 M, DBN, 68 h) and the reaction was processed using Workup E, to afford the title compound as a white solid (6.7 mg, 51% yield). Purity: 87%. $^1$H NMR (600 MHz, DMSO-d$_6$) δ 10.14 (bs, 1H), 9.81 (s, 1H), 9.71 (s, 1H), 8.38 (s, 1H), 8.04 (d, J=7.4 Hz, 2H), 7.88 (d, J=8.2 Hz, 2H), 7.83 (d, J=8.5 Hz, 2H), 7.72 (d, J=8.5 Hz, 2H), 7.49 (s, 2H), 7.15 (s, 2H). $^{13}$C NMR (151 MHz, DMSO-d$_6$) δ 163.86, 163.23, 159.80, 156.77, 155.95, 148.91, 143.82, 139.44, 134.95, 126.81, 126.75, 122.65, 121.39, 116.26, 114.54. HRMS (ESI): calc. for [M+H]$^+$ C$_{19}$H$_{17}$N$_8$O$_6$S 485.0992 found 485.0976. [17a+H]$^+$ 255.0667 was also observed due to in-source fragmentation.

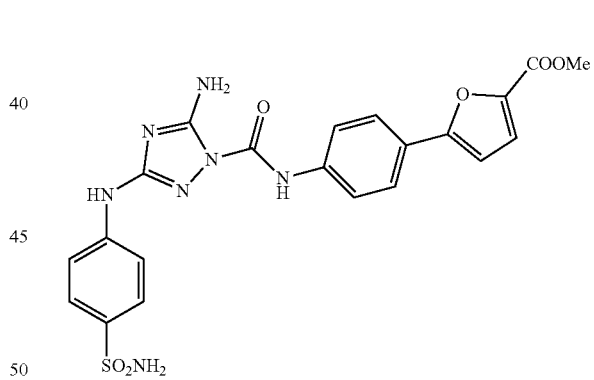

Synthesis of Methyl 5-(4-(5-amino-3((4-sulfamoylphenyl)amino)-1H-1,2,4-triazole-1-carboxamido)phenyl)furan-2-carboxylate (13')

Compound 19h (86 mg, 0.26 mmol) was reacted with 17a (65 mg, 0.26 mmol) for 2.5 h, according to General Procedure B. The reaction was processed using Workup B with modified column chromatography (DCM/MeCN) to provide the title compound as a white solid (20 mg, 16% yield). $^1$H NMR (600 MHz, DMSO-d$_6$) δ 9.76 (s, 1H), 9.70 (s, 1H), 7.87-7.81 (m, 6H), 7.72 (d, J=8.7 Hz, 2H), 7.46 (s, 2H), 7.43 (d, J=3.7 Hz, 1H), 7.17-7.13 (m, 3H), 3.85 (s, 3H). ESI-MS m/z: [M+H]$^+$: 498.1.

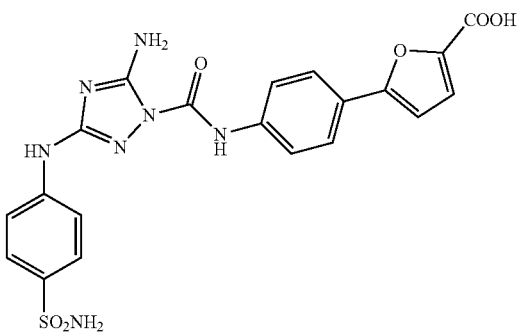 [SMILES: Nc1nc(Nc2ccc(S(N)(=O)=O)cc2)nn1C(=O)Nc1ccc(-c2ccc(C(=O)O)o2)cc1]

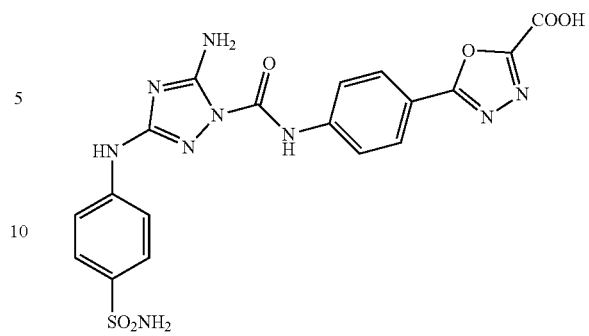

Synthesis of 5-(4-(5-amino-3((4-sulfamoylphenyl)amino)-1H-1,2,4-triazole-1-carboxamido)phenyl) furan-2-carboxylic acid (13)

Compound 13' (11 mg, 22 μmol), in MeCN (0.07 M) with DBN, was hydrolyzed for 83 h to afford the title product as pale yellow solid (4 mg, 38% yield). Purity: 84%. $^1$H NMR (600 MHz, DMSO-$d_6$) δ 9.72 (s, 1H), 9.69 (s, 1H), 7.83 (d, J=8.8 Hz, 2H), 7.79 (s, 4H), 7.72 (d, J=8.7 Hz, 2H), 7.45 (s, 2H), 7.15 (s, 2H), 7.07 (bs, 1H) 7.00 (s, 1H). Carboxylic acid hydrogen is not observed. $^{13}$C NMR (151 MHz, DMSO-$d_6$) δ 161.02, 156.71, 155.90, 148.96, 143.84, 137.01, 134.90, 126.81, 126.14, 124.70, 124.33, 121.76, 117.56, 116.24, 114.54, 106.81. HRMS (ESI): calc. for [M+H]$^+$ $C_{20}H_{18}N_7O_6S$ 484.1039 found 484.1016.

Synthesis of 5-(4-(5-amino-3((4-sulfamoylphenyl)amino)-1H-1,2,4-triazole-1-carboxamido)phenyl)-1,3,4-oxadiazole-2-carboxylic acid (14)

Compound 14' (58 mg, 112 μmol) in MeCN (0.04 M) with DBN, was hydrolyzed for 90 h to afford the title product as white solid (12 mg, 21% yield). Purity: 90%. $^1$H NMR (600 MHz, DMSO-$d_6$) δ 9.90 (s, 1H), 9.72 (s, 1H), 9.33 (s, 1H), 8.06 (d, J=8.6 Hz, 2H), 8.02-7.92 (m, 2H), 7.83 (d, J=8.7 Hz, 2H), 7.72 (d, J=8.7 Hz, 2H), 7.49 (s, 2H), 7.16 (s, 2H). $^{13}$C NMR (151 MHz, DMSO-$d_6$) δ 163.43, 156.80, 155.97, 154.31, 148.89, 143.79, 140.76, 134.97, 127.42, 127.12, 126.79, 121.50, 118.65, 116.27. HRMS (ESI): calc. for [M-CO$_2$+H]$^+$ $C_{17}H_{16}N_9O_4S$ 442.1046 found 442.1046. [17a+H]$^+$ 255.0678 was also observed due to in-source fragmentation.

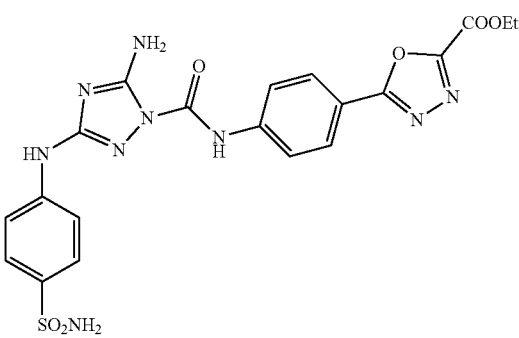 [SMILES: CCOC(=O)c1nnc(-c2ccc(NC(=O)n3nc(Nc4ccc(S(N)(=O)=O)cc4)nc3N)cc2)o1]

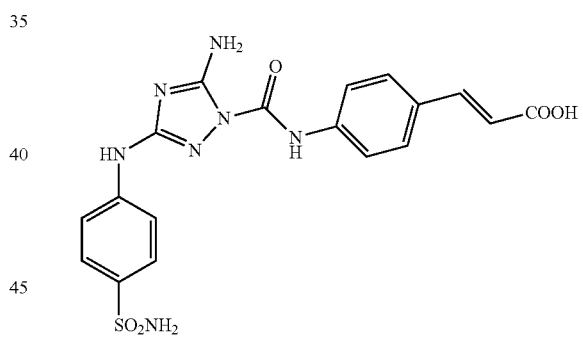

Synthesis of Ethyl 5-(4-(5-amino-3((4-sulfamoylphenyl)amino)-1H-1,2,4-triazole-1-carboxamido)phenyl)-1,3,4-oxadiazole-2-carboxylate (14')

Compound 19i (90 mg, 0.26 mmol) was reacted with 17a (65 mg, 0.26 mmol) for 2.5 h. The reaction was processed using Workup A with modified column chromatography (DCM/MeCN) to provide the title product as a white solid (59 mg, 45% yield). $^1$H NMR (600 MHz, DMSO-$d_6$) δ 9.96 (s, 1H), 9.72 (s, 1H), 8.11 (d, J=8.7 Hz, 2H), 8.01 (d, J=8.7 Hz, 2H), 7.84 (d, J=8.8 Hz, 2H), 7.72 (d, J=8.8 Hz, 2H), 7.50 (s, 2H), 7.16 (s, 2H), 4.46 (q, J=7.1 Hz, 2H), 1.38 (t, J=7.1 Hz, 3H). $^{13}$C NMR (151 MHz, DMSO-$d_6$) δ 165.21, 156.83, 156.31, 156.00, 154.11, 148.87, 143.79, 141.58, 135.00, 127.98, 126.82, 121.49, 117.87, 116.30, 62.94, 13.94. ESI-MS m/z: [M+H]$^+$: 514.2.

Synthesis of (E)-3-(4-(5-amino-3((4-sulfamoylphenyl)amino)-1H-1,2,4-triazole-1-carboxamido)phenyl)acrylic acid (15)

(E)-3-(4-((phenoxycarbonyl)amino)phenyl)acrylic acid (19j; 100 mg, 0.35 mmol) was reacted with 4-((5-amino-1H-1,2,4-triazol-3-yl)amino)benzenesulfonamide (17a; 90 mg, 0.35 mmol) and 3.0 eq. triethylamine according to General Procedure B. After 1 h the reaction was stopped, solvent was evaporated, and the residue was triturated with methanol. Subsequently water was added, the mixture was acidified to ~pH 4, and was kept at low temperature for 14 h. Afterwards the suspension was filtered, the solid was allowed to dry under vacuum, and was purified first by normal phase column chromatography (DCM/MeCN/MeOH) and last by HPLC, to afford compound 15 as a white solid (8 mg, 5% Yield). Purity: 99%. $^1$H NMR (600 MHz, DMSO-$d_6$) δ 9.73 (s, 1H), 9.70 (s, 1H), 7.82 (d, J=8.8 Hz, 2H), 7.75 (d, J=8.6 Hz, 2H), 7.71 (d, J=8.6 Hz, 4H), 7.55 (d, J=16.0 Hz, 1H), 7.46 (s, 2H), 7.15 (s, 2H), 6.49 (d, J=16.0 Hz, 1H). Carboxylic acid hydrogen is not observed. $^{13}$C NMR (151 MHz, DMSO-$d_6$) δ 167.93, 156.75, 155.93, 148.89, 143.83, 142.86, 138.94, 134.93, 130.28, 128.73, 126.82, 121.29, 118.82, 116.24. HRMS (ESI): calc. for [M+H]$^+$ C$_{18}$H$_{18}$N$_7$O$_5$S 444.1090 found 444.1081.

The terms and expressions employed herein are used as terms of description and not of limitation, and there is no intention in the use of such terms and expressions of excluding any equivalents of the features shown and described or portions thereof, but it is recognized that various modifications are possible within the scope of the embodiments of the present application. Thus, it should be understood that although the present application describes specific embodiments and optional features, modification and variation of the compositions, methods, and concepts herein disclosed may be resorted to by those of ordinary skill in the art, and that such modifications and variations are considered to be within the scope of embodiments of the present application.

Enumerated Embodiments

The following exemplary embodiments are provided, the numbering of which is not to be construed as designating levels of importance.

Embodiment 1 provides a compound of Formula I, or a pharmaceutically acceptable salt or tautomer thereof:

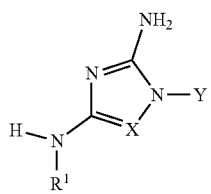

Formula I wherein,
Y is selected from the group consisting of —CH$_2$—R$^2$, —C(=O)NR$^2$R$^3$, optionally substituted C$_{5-10}$ heteroaryl, and optionally substituted C$_{5-6}$ heterocycloalkyl;
wherein the optional substitution is independently at least one substituent selected from the group consisting of C$_{1-5}$ alkyl, C$_{1-5}$ alkoxy, C$_{1-5}$ thioalkyl, C$_{1-5}$ aminoalkyl, C$_{5-10}$ aryl, C$_{5-10}$ heteroaryl, =O (oxo), F, Cl, Br, I, C(=O)OR, NHC(=O)R, and OH;
R$^1$ and R$^2$ are each independently selected from the group consisting of C$_{2-6}$ alkenyl, C$_{3-7}$ cycloalkyl, C$_{6-10}$ aryl, 5-10 membered heteroaryl, 4-10 membered heterocycloalkyl, C$_{6-10}$-5-6 membered heterobiaryl, 5-6 membered-C$_{6-10}$ heterobiaryl, and C$_{6-10}$—C$_{6-10}$ biaryl,
each one being independently optionally substituted by at least one substituent selected from the group consisting of F, Cl, Br, I, OR, OC(=O)N(R)$_2$, CN, NO$_2$, CF$_3$, OCF$_3$, R, N(R)$_2$, SR, SOR, SO$_2$R, SO$_2$N(R)$_2$, SO$_3$R, C(=O)R, C(=O)OR, OC(=O)R, O(CH$_2$)$_{0-2}$C(=O)OR, C(=O)N(R)$_2$, OC(=O)N(R)$_2$, (CH$_2$)$_{0-2}$N(R)C(=O)R, N(R)SO$_2$R, N(R)C(=O)OR, N(R)C(=O)R, N(R)C(=O)N(R)$_2$, and C(=NH)N(R)$_2$,
wherein each occurrence of R is independently selected from the group consisting of hydrogen and (C$_1$-C$_6$) hydrocarbyl; or wherein two R groups bonded to a nitrogen atom or to adjacent nitrogen atoms can together with the nitrogen atom or atoms form a heterocyclyl;
R$^3$ is H or C$_{1-4}$ hydrocarbyl;
X is N or C—R$^4$, wherein R$^4$ is H or C$_{1-4}$ hydrocarbyl optionally substituted by 1 to 3 substituents selected from the group consisting of OR', NHR', and NR'$_2$,
wherein each occurrence of R' is independently selected from the group consisting of hydrogen and (C$_1$-C$_6$)hydrocarbyl; or wherein two R' groups bonded to a nitrogen atom or to adjacent nitrogen atoms can together with the nitrogen atom or atoms form a heterocyclyl.

Embodiment 2 provides the compound of embodiment 1, wherein R$^1$ is C$_{6-10}$ aryl.

Embodiment 3 provides the compound of any one of embodiments 1-2, wherein Y is —C(=O)NR$^2$R$^3$.

Embodiment 4 provides the compound of any one of embodiments 1-3, wherein R$^2$ is C$_{6-10}$ aryl, 5-10 membered heteroaryl, C$_{6-10}$-5-6 membered heterobiaryl, 5-6 membered-C$_{6-10}$ heterobiaryl, or C$_{6-10}$-C$_{6-10}$ biaryl.

Embodiment 5 provides the compound of any one of embodiments 1-4, wherein X is N.

Embodiment 6 provides the compound of any one of embodiments 1-5, wherein R$^3$ is H.

Embodiment 7 provides the compound of any one of embodiments 1-6, wherein R$^1$ has the structure:

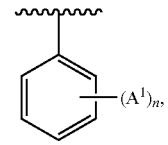

wherein:
each occurrence of A$^1$ is independently selected from the group consisting of F, Cl, Br, I, OR, OC(=O)N(R)$_2$, CN, NO$_2$, CF$_3$, OCF$_3$, R, N(R)$_2$, SR, SOR, SO$_2$R, SO$_2$N(R)$_2$, SO$_3$R, C(=O)R, C(=O)OR, OC(=O)R, O(CH$_2$)$_{0-2}$C(=O)OR, C(=O)N(R)$_2$, OC(=O)N(R)$_2$, (CH$_2$)$_{0-2}$N(R)C(=O)R, N(R)SO$_2$R, N(R)C(=O)OR, N(R)C(=O)R, N(R)C(=O)N(R)$_2$, and C(=NH)N(R)$_2$, wherein each occurrence of R is independently selected from the group consisting of hydrogen and (C$_1$-C$_6$)hydrocarbyl; and
n is an integer from 0 to 5.

Embodiment 8 provides the compound of any one of embodiments 1-7, wherein the compound is of Formula Ia:

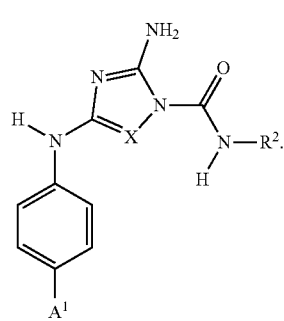

Formula Ia

Embodiment 9 provides the compound of any one of embodiments 1-8, wherein $A^1$ is $SO_2NH_2$ or $C(=O)NHCH_3$.

Embodiment 10 provides the compound of any one of embodiments 1-9, wherein $R^2$ has the structure

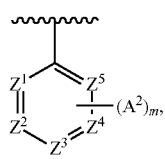

wherein:
each of $Z^1$-$Z^5$ is independently $CA^2$ or N, wherein zero, one, or two of $Z^1$-$Z^5$ are N;
each occurrence of $A^2$ is independently selected from the group consisting of

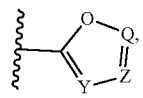

F, Cl, Br, I, OR, OC(=O)N(R)$_2$, CN, NO$_2$, CF$_3$, OCF$_3$, R, N(R)$_2$, SR, SOR, SO$_2$R, SO$_2$N(R)$_2$, SO$_3$R, C(=O)R, C(=O)OR, OC(=O)R, $C_{2-6}$ alkenyl-COOR, $C_{2-6}$ alkenyl-CONR$_2$, O(CH$_2$)$_{0-2}$C(=O)OR, C(=O)N(R)$_2$, OC(=O)N(R)$_2$, (CH$_2$)$_{0-2}$N(R)C(=O)R, N(R)SO$_2$R, N(R)C(=O)OR, N(R)C(=O)R, N(R)C(=O)N(R)$_2$, and C(=NH)N(R)$_2$;
wherein zero, one, or two $A^2$ can be independently

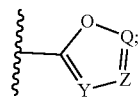

wherein Y, Z, and Q are each independently C—$R^5$ or N, wherein each $R^5$ is independently selected from the group consisting of H, F, Cl, Br, I, OR, OC(=O)N(R)$_2$, CN, NO$_2$, CF$_3$, OCF$_3$, R, N(R)$_2$, SR, SOR, SO$_2$R, SO$_2$N(R)$_2$, SO$_3$R, C(=O)R, C(=O)OR, OC(=O)R, O(CH$_2$)$_{0-2}$C(=O)OR, C(=O)N(R)$_2$, OC(=O)N(R)$_2$, (CH$_2$)$_{0-2}$N(R)C(=O)R, N(R)SO$_2$R, N(R)C(=O)OR, N(R)C(=O)R, N(R)C(=O)N(R)$_2$, and C(=NH)N(R)$_2$;
wherein each occurrence of R is independently selected from the group consisting of hydrogen and (C$_1$-C$_6$) hydrocarbyl; and
m is an integer from 0 to 5.

Embodiment 11 provides the compound of any one of embodiments 1-10, wherein $Z^1$ is N and $Z^2$-$Z^5$ are CH.

Embodiment 12 provides the compound of any one of embodiments 1-11, wherein $Z^2$ is N, and $Z^1$ and $Z^3$-$Z^5$ are CH.

Embodiment 13 provides the compound of any one of embodiments 1-12, wherein m is 1.

Embodiment 14 provides the compound of any one of embodiments 1-13, wherein the compound is of Formula Ib, Formula Ic, or Formula Id:

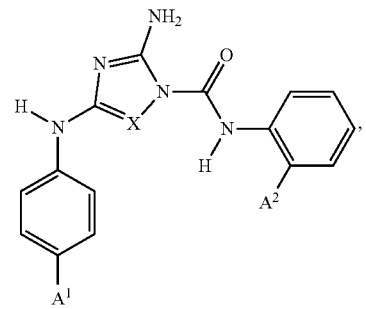
Formula Ib

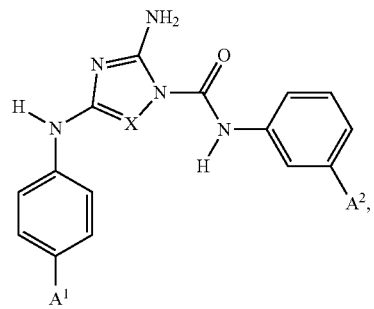
Formula Ic or

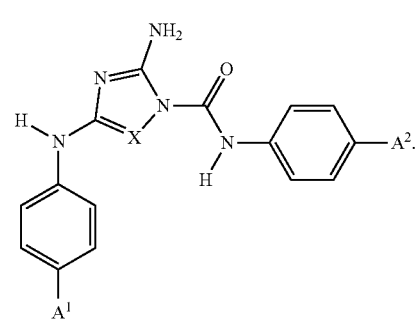
Formula Id

Embodiment 15 provides the compound of any one of embodiments 1-14, wherein $A^1$ is $SO_2NH_2$ or $C(=O)NHCH_3$.

Embodiment 16 provides the compound of any one of embodiments 1-15, wherein $A^2$ is selected from the group consisting of:

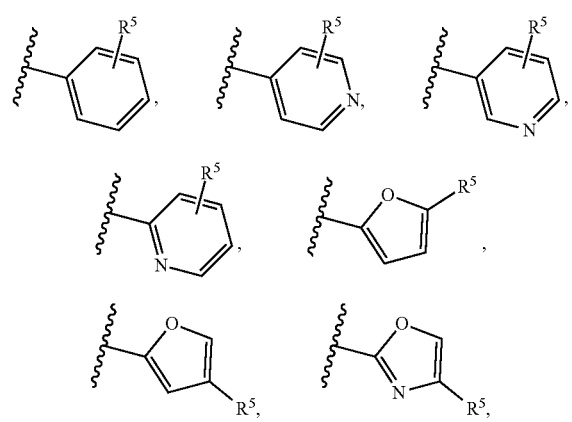

-continued
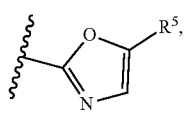 and 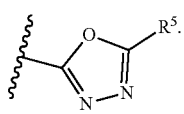
Embodiment 17 provides the compound of any one of embodiments 1-16, wherein $R^5$ is COOH or COOCH$_3$.
Embodiment 18 provides the compound of any one of embodiments 1-17, wherein $A^2$ is selected from the group consisting of:
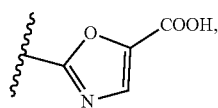 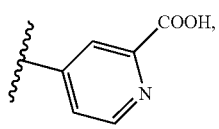
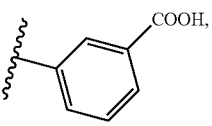 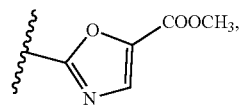
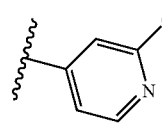 and 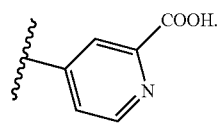
Embodiment 19 provides the compound of any one of embodiments 1-18, which is selected from the group consisting of
2
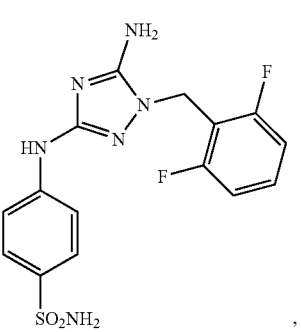
3
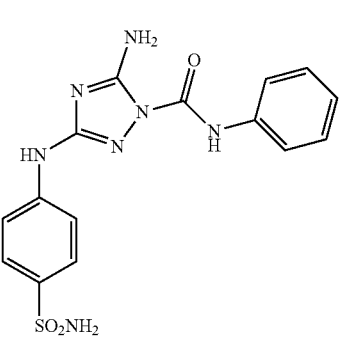
4
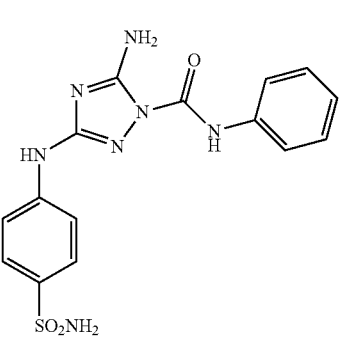
5
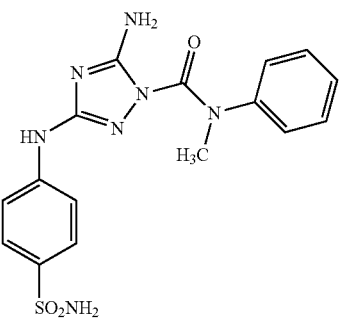
6
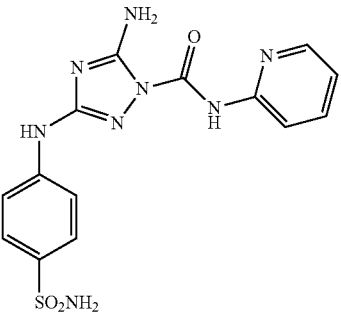
7
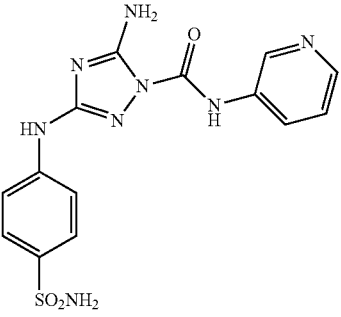
8
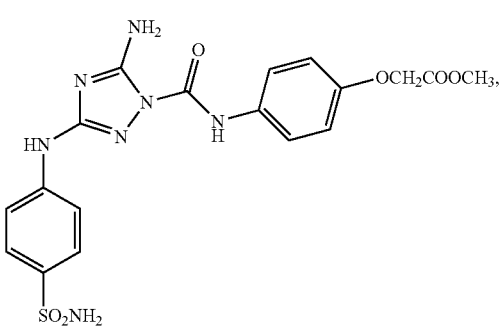

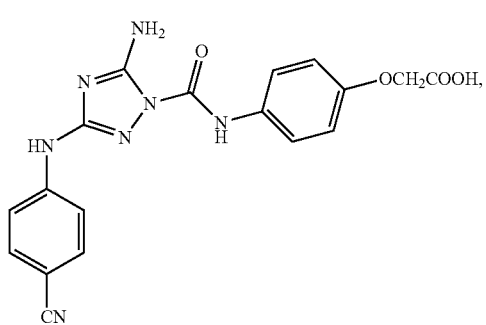

9

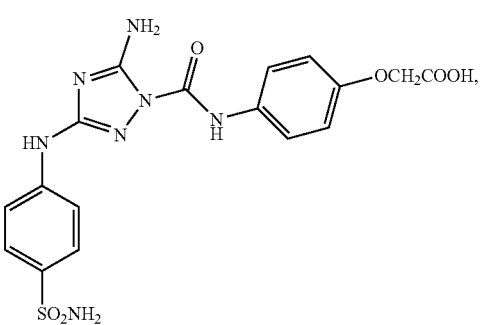

10

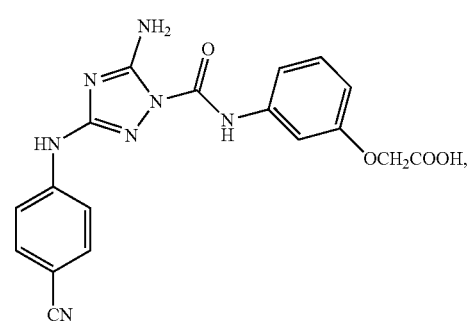

11

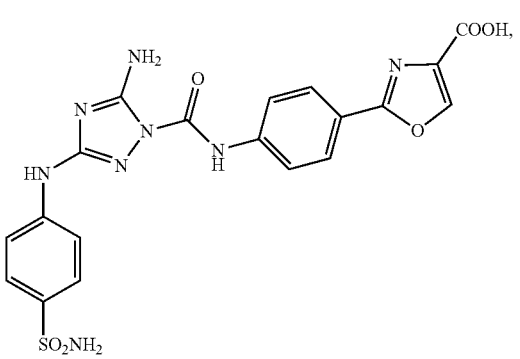

12

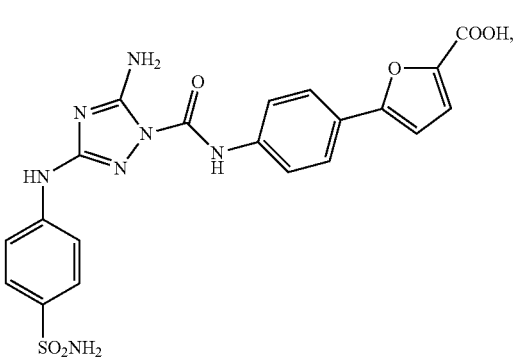

13

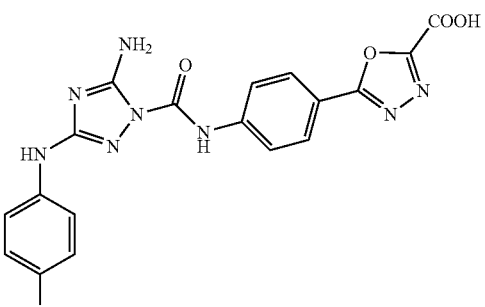

14

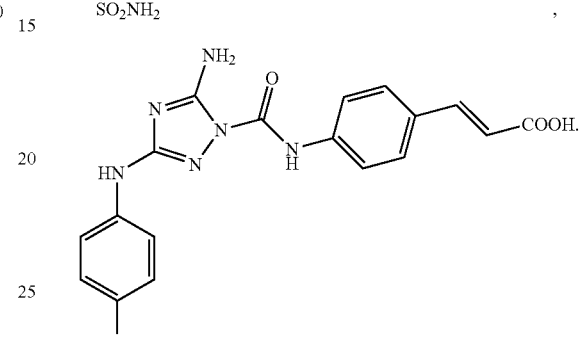

, and

15

Embodiment 20 provides a method of treating, ameliorating, and/or preventing a myeloproliferative neoplasm in a patient, the method comprising administering to the patient a therapeutically effective amount of the compound of claim 1.

Embodiment 21 provides the method of embodiment 20, wherein the myeloproliferative neoplasm is selected from the group consisting of chronic myelogenous leukemia (CML), polycythemia vera, primary myelofibrosis, essential thrombocythemia, chronic neutrophilic leukemia, and chronic eosinophilic leukemia.

Embodiment 22 provides the method of any one of embodiments 20-21, wherein the composition comprises at least one pharmaceutically acceptable excipient.

Embodiment 23 provides the method of any one of embodiments 20-22, wherein the patient is a mammal.

Embodiment 24 provides the method of any one of embodiments 20-23, wherein the patient is human.

Embodiment 25 provides the method of any one of embodiments 20-24, wherein the compound is administered by a route selected from the group consisting of oral, transdermal, intravesical, intrapulmonary, intraduodenal, intragastrical, intrathecal, subcutaneous, intramuscular, intradermal, intra-arterial, intravenous, intrabronchial, inhalation, and topical.

Embodiment 26 provides the method of any one of embodiments 20-25, further comprising concurrently or sequentially administering at least one additional agent.

Embodiment 27 provides the method of any one of embodiments 20-26, wherein the at least one additional agent is selected from the group consisting of Adriamycin PFS (Doxorubicin Hydrochloride), Adriamycin RDF (Doxorubicin Hydrochloride), Arsenic Trioxide, Azacitidine Cerubidine (Daunorubicin Hydrochloride), Clafen (Cyclophosphamide), Cyclophosphamide, Cytarabine, Cytosar-U (Cytarabine), Cytoxan (Cyclophosphamide), Dacogen (Decitabine), Dasatinib, Daunorubicin Hydrochloride, Decitabine Doxorubicin Hydrochloride, Etoposide Phosphate, Gleevec (Imatinib Mesylate), Imatinib Mesylate, Jakafi (Ruxolitinib Phosphate), Nilotinib, Rubidomycin (Daunorubicin Hydrochloride), Ruxolitinib Phosphate, Sprycel (Dasatinib), Tarabine PFS (Cytarabine), Tasigna (Nilotinib), Trisenox (Arsenic Trioxide), and Vidaza (Azacitidine).

Embodiment 28 provides a method of making the compound of any one of embodiments 10-19, the method comprising reacting a compound having the structure:

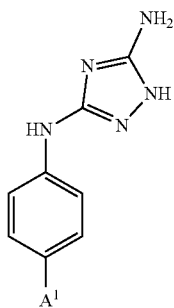

with a compound having the structure:

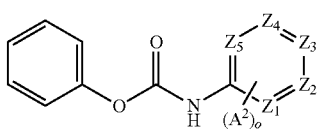

in a solvent to yield a compound of Formula I, wherein $A^1$, $A^2$, and $Z^1$-$Z^5$ are as defined in claim 1.

Embodiment 29 provides the method of embodiment 28, wherein the solvent comprises dioxane.

Embodiment 30 provides the method of any one of embodiments 28-29, wherein the reacting is at a temperature of about 95° C. to about 115° C.

Embodiment 31 provides the method of any one of embodiments 28-30, wherein the concentration of (A) in the solvent is about 0.35 M to about 0.7 M.

What is claimed is:

1. A compound of Formula Ia, or a pharmaceutically acceptable salt or tautomer thereof:

Formula Ia

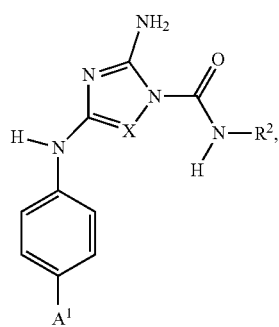

wherein:
X is N;
$A^1$ is independently selected from the group consisting of F, Cl, Br, I, OC(=O)N(R)$_2$, CN, NO$_2$, CF$_3$, OCF$_3$, (C$_1$-C$_6$)hydrocarbyl, N(R)$_2$, SR, SOR, SO$_2$R, SO$_2$N(R)$_2$, SO$_3$R, C(=O)R, C(=O)OR, OC(=O)R, O(CH$_2$)$_{0-2}$C(=O)OR, C(=O)N(R)$_2$, OC(=O)N(R)$_2$, (CH$_2$)$_{0-2}$N(R)C(=O)R, N(R)SO$_2$R, N(R)C(=O)OR, N(R)C(=O)R, N(R)C(=O)N(R)$_2$, and C(=NH)N(R)$_2$,
wherein each occurrence of R is independently selected from the group consisting of hydrogen and (C$_6$-C$_6$) hydrocarbyl; or
wherein two R groups bonded to a nitrogen atom or to adjacent nitrogen atoms can combine with the nitrogen atom or atoms to form a heterocyclyl;
$R^2$ is:

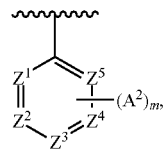

wherein:
each of $Z^1$, $Z^2$, $Z^3$, $Z^4$, and $Z^5$ is C-$A^2$, provided at least one of $Z^1$ and $Z^5$ is CH;
each occurrence of $A^2$ is independently selected from the group consisting of

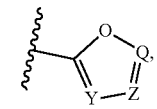

F, Cl, Br, I, OR, OC(=O)N(R)$_2$, CN, NO$_2$, CF$_3$, OCF$_3$, R, N(R)$_2$, SR, SOR, SO$_2$R, SO$_2$N(R)$_2$, SO$_3$R, C(=O)R, C(=O)OR, OC(=O)R, C$_{2-6}$ alkenyl-COOR, C$_{2-6}$ alkenyl-CONR$_2$, O(CH$_2$)$_{0-2}$C(=O)OR, C(=O)N(R)$_2$, OC(=O)N(R)$_2$, (CH$_2$)$_{0-2}$N(R)C(=O)R, N(R)SO$_2$R, N(R)C(=O)OR, N(R)C(=O)R, N(R)C(=O)N(R)$_2$, and C(=NH)N(R)$_2$,
provided at least one occurrence of $A^2$ is not hydrogen;
wherein zero, one, or two $A^2$ can be independently

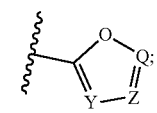

wherein Y, Z, and Q are each independently C—$R^5$ or N, wherein each $R^5$ is independently selected from the group consisting of H, F, Cl, Br, I, OR, OC(=O)N(R)$_2$, CN, NO$_2$, CF$_3$, OCF$_3$, R, N(R)$_2$, SR, SOR, SO$_2$R, SO$_2$N(R)$_2$, SO$_3$R, C(=O)R, C(=O)OR, OC(=O)R, O(CH$_2$)$_{0-2}$C(=O)OR, C(=O)N(R)$_2$, OC(=O)N(R)$_2$, (CH$_2$)$_{0-2}$ N(R)C(=O)R, N(R)SO$_2$R, N(R)C(=O)OR, N(R)C(=O)R, N(R)C(=O)N(R)$_2$, and C(=NH)N(R)$_2$;
wherein each occurrence of R is independently selected from the group consisting of hydrogen and (C$_6$-C$_6$)hydrocarbyl; and
m is 1, 2, 3, 4, or 5.

2. The compound of claim 1, wherein $A^1$ is CN, $OCF_3$, $SO_2NH_2$, or $C(=O)NHCH_3$.

3. The compound of claim 1, wherein m is 1.

4. The compound of claim 1, wherein the compound is of Formula Ib, Formula Ic, or Formula Id:

Formula Ib

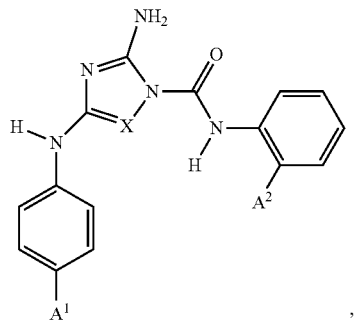

Formula Ic

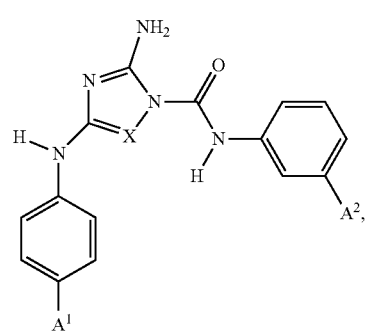

Formula Id

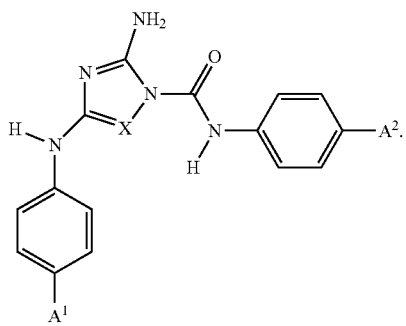

5. The compound of claim 4, wherein $A^1$ is CN, $OCF_3$, $SO_2NH_2$, or $C(=O)NHCH_3$.

6. The compound of claim 1, wherein $A^2$ is selected from the group consisting of:

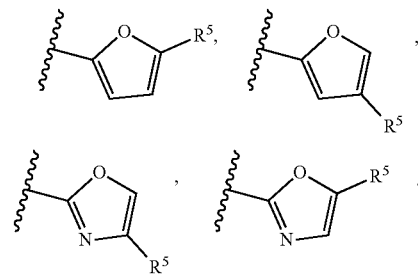

and

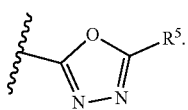

7. The compound of claim 6, wherein $R^5$ is COOH or $COOCH_3$.

8. The compound of claim 6, wherein $A^2$ is selected from the group consisting of:

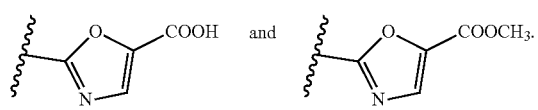 [SMILES: *c1ncc(C(=O)O)o1 ; *c1ncc(C(=O)OC)o1]

9. A compound, or a pharmaceutically acceptable salt or tautomer thereof, selected from the group consisting of:

2

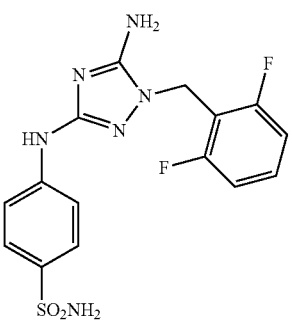

3

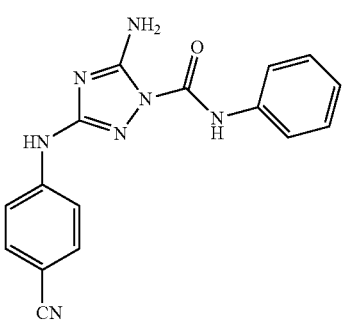

4

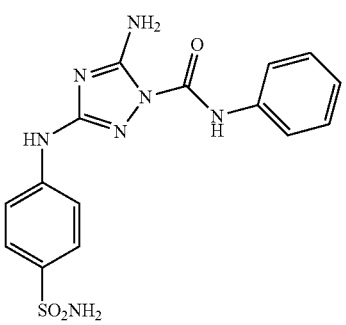

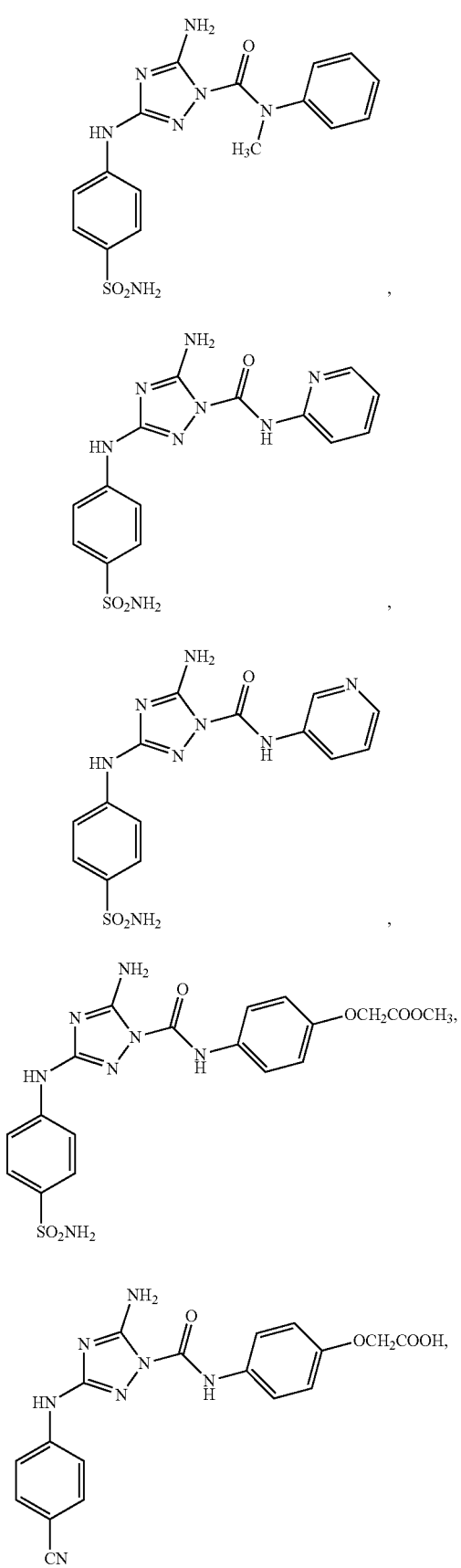
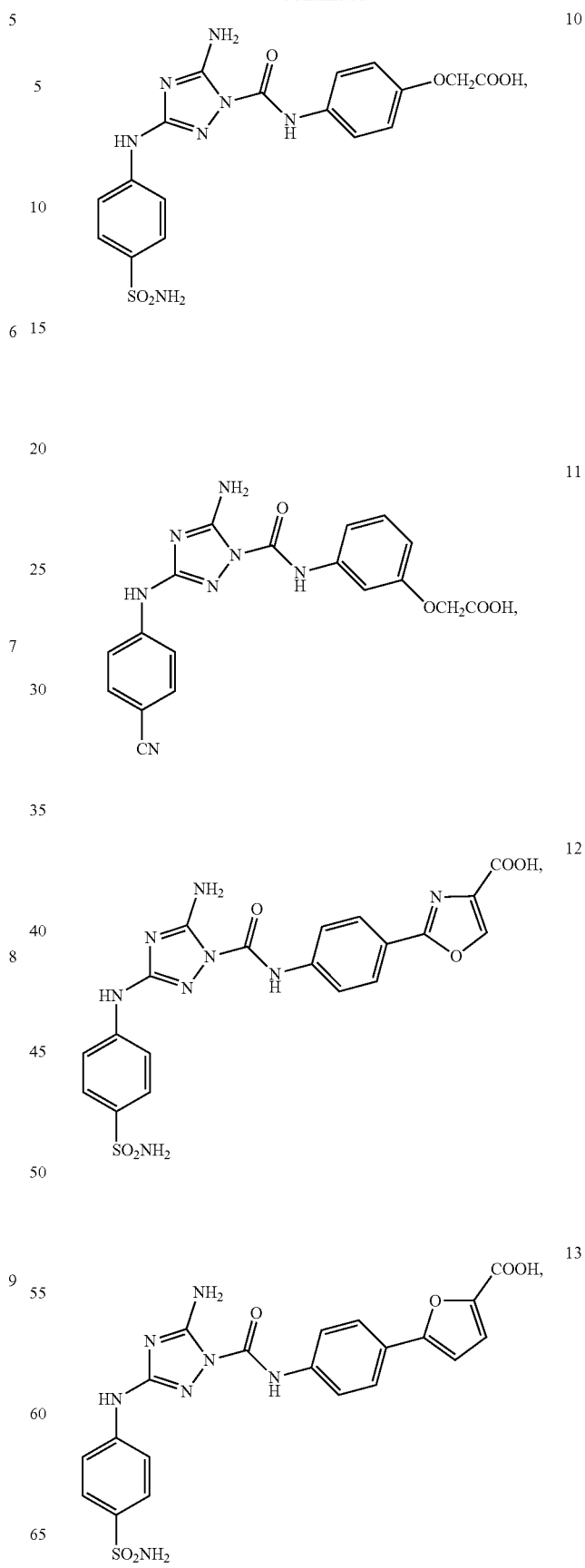

-continued

14

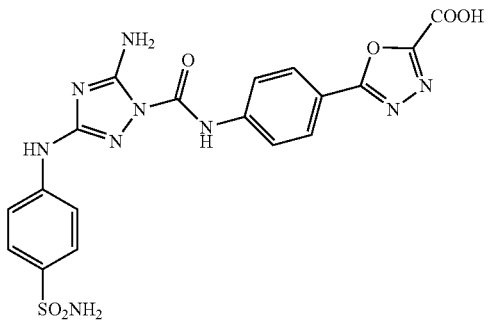

, and

15

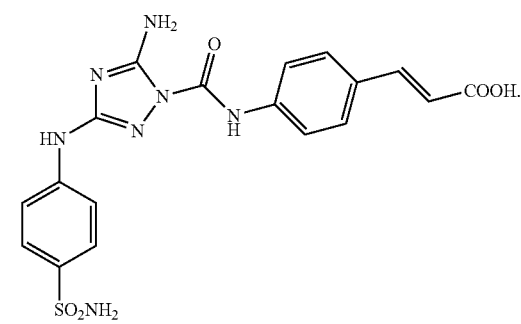

10. A method of treating or ameliorating a myeloproliferative neoplasm in a patient, the method comprising administering to the patient a therapeutically effective amount of a compound of Formula Ia, or a pharmaceutically acceptable salt or tautomer thereof.

Formula Ia

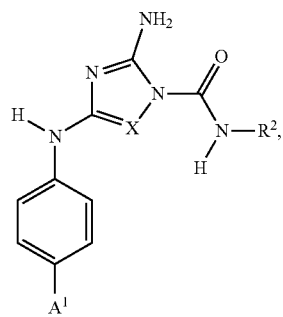

wherein:

X is N;

$A^1$ is independently selected from the group consisting of F, Cl, Br, I, OC (=O) N(R)$_2$, CN, NO$_2$, CF$_3$, OCF$_3$, (C$_1$-C$_6$) hydrocarbyl, N(R)$_2$, SR, SOR, SO$_2$R, SO$_2$N(R)$_2$, SO$_3$R, C(=O)R, C(=O)OR, OC(=O)R, O(CH$_2$)$_{0-2}$C(=O)OR, C(=O)N(R)$_2$, OC(=O)N(R)$_2$, (CH2)$_{0-2}$N(R)C(=O)R, N(R)SO$_2$R, N(R)C(=O)OR, N(R)C(=O)R, N(R)C =O)N(R)$_2$, and C(=NH) N(R)$_2$, wherein each occurrence of R is independently selected from the group consisting of hydrogen and (C$_1$-C$_6$) hydrocarbyl; or wherein two R groups bonded to a nitrogen atom or to adjacent nitrogen atoms can combine with the nitrogen atom or atoms to form a heterocyclyl;

R2 is:

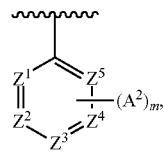

wherein:

each of $Z^1$, $Z^2$, $Z^3$, $Z^4$, and $Z^5$ is C-A$^2$, provided at least one of $Z^1$ and $Z^5$ is CH;

each occurrence of $A^2$ is independently selected from the group consisting of

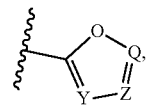

F, Cl, Br, I, OR, OC(=O)N(R)$_2$, CN, NO$_2$, CF$_3$, OCF$_3$, R, N(R)$_2$, SR, SOR, SO$_2$R, SO$_2$N(R)$_2$, SO$_3$R, C(=O)R, C(=O)OR, OC(=O)R, C$_{2-6}$ alkenyl-COOR, C$_{2-6}$ alkenyl-CONR$_2$, O(CH$_2$)$_{0-2}$C(=O)OR, C(=O)N(R)$_2$, OC(=O)N(R)$_2$, (CH2)$_{0-2}$N(R)C(=O)R, N(R)SO$_2$R, N(R)C(=O)OR, N(R)C(=O) R. N (R) C (=O) N (R) 2, and C (=NH) N (R) 2, provided at least one occurrence of A2 is not hydrogen;

wherein zero, one, or two $A^2$ can be independently

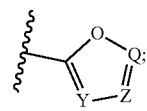

wherein Y, Z, and Q are each independently C-R$^5$ or N, wherein each R$^5$ is independently selected from the group consisting of H, F, Cl, Br, I, OR, OC(=O) N(R)$_2$, CN, NO$_2$, CF$_3$, OCF$_3$, R, N(R)$_2$, SR, SOR, SO$_2$R, SO$_2$N(R)$_2$, SO$_3$R, C(=O)R, C(=O)OR, OC(=O)R, O(CH$_{2)0-2}$C(=O)OR, C(=O)N(R)$_2$, OC(=O)N(R)$_2$, (CH2)$_{0-2}$N (R)C(=O)R, N(R)SO$_2$R, N(R)C(=O)OR, N(R)C(=O)R. N(R)C(=O)N(R)$_2$, and C(=NH) N(R)$_2$;

wherein each occurrence of R is independently selected from the group consisting of hydrogen and (C$_1$-C$_6$) hydrocarbyl; and m is 1, 2, 3, 4, or 5.

11. The method of claim 10, wherein the myeloproliferative neoplasm is selected from the group consisting of chronic myelogenous leukemia (CML), polycythemia vera, primary myelofibrosis, essential thrombocythemia, chronic neutrophilic leukemia, and chronic eosinophilic leukemia.

12. The method of claim 10, wherein the composition comprises at least one pharmaceutically acceptable excipient.

13. The method of claim 10, wherein the patient is a mammal.

14. The method of claim 10, wherein the patient is human.

15. The method of claim 10, wherein the compound is administered by a route selected from the group consisting of oral, transdermal, intravesical, intrapulmonary, intraduodenal, intragastrical, intrathecal, subcutaneous, intramuscular, intradermal, intra-arterial, intravenous, intrabronchial, inhalation, and topical.

16. The method of claim 10, further comprising concurrently or sequentially administering at least one additional agent.

17. The method of claim 16, wherein the at least one additional agent is selected from the group consisting of Adriamycin PFS (Doxorubicin Hydrochloride), Adriamycin RDF (Doxorubicin Hydrochloride), Arsenic Trioxide, Azacitidine Cerubidine (Daunorubicin Hydrochloride), Clafen (Cyclophosphamide), Cyclophosphamide, Cytarabine, Cytosar-U (Cytarabine), Cytoxan (Cyclophosphamide), Dacogen (Decitabine), Dasatinib, Daunorubicin Hydrochloride, Decitabine Doxorubicin Hydrochloride, Etoposide Phosphate, Gleevec (Imatinib Mesylate), Imatinib Mesylate, Jakafi (Ruxolitinib Phosphate), Nilotinib, Rubidomycin (Daunorubicin Hydrochloride), Ruxolitinib Phosphate, Sprycel (Dasatinib), Tarabine PFS (Cytarabine), Tasigna (Nilotinib), Trisenox (Arsenic Trioxide), and Vidaza (Azacitidine).

18. A method of making a compound of Formula Ia, or a pharmaceutically acceptable salt or tautomer thereof,

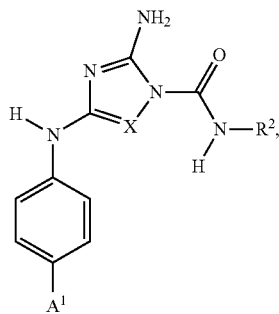

Formula Ia wherein:

X is N;

$A^1$ is independently selected from the group consisting of F, Cl, Br, I, OC(=O)N(R)$_2$, CN, NO$_2$, CF$_3$, OCF$_3$, (C$_1$-C$_6$) hydrocarbyl, N(R)$_2$, SR, SOR, SO$_2$R, SO$_2$N(R)$_2$, SO$_3$R, C(=O)R, C(=O)OR, OC(=O)R, O(CH$_2$)$_{0-2}$C(=O)OR, C(=O)N(R)$_2$, OC(=O)N(R)$_2$, (CH2)$_{0-2}$N(R)C(=O)R, N(R)SO$_2$R, N(R)C(=O)OR, N(R)C(=O)R, N(R)C=O)N(R)$_2$, and C(=NH)N(R)$_2$, wherein each occurrence of R is independently selected from the group consisting of hydrogen and (C$_1$-C$_6$) hydrocarbyl; or wherein two R groups bonded to a nitrogen atom or to adjacent nitrogen atoms can combine with the nitrogen atom or atoms to form a heterocyclyl;

R2 is:

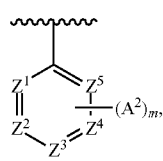

wherein:

each of $Z^1$, $Z^2$, $Z^3$, $Z^4$, and $Z^5$ is C-$A^2$, provided at least one of $Z^1$ and $Z^5$ is CH;

each occurrence of $A^2$ is independently selected from the group consisting of

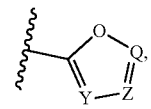

F, Cl, Br, I, OR, OC(=O)N(R)$_2$, CN, NO$_2$, CF$_3$, OCF$_3$, R, N(R)$_2$, SR, SOR, SO$_2$R, SO$_2$N(R)$_2$, SO$_3$R, C(=O)R, C(=O)OR, OC(=O)R, C$_{2-6}$ alkenyl-COOR, C$_{2-6}$ alkenyl-CONR$_2$, O(CH$_2$)$_{0-2}$C(=O)OR, C(=O)N(R)$_2$, OC(=O)N(R)$_2$, (CH2)$_{0-2}$N(R)C(=O)R, N(R)SO$_2$R, N(R)C(=O)OR, N(R)C(=O)R. N(R)C(=O)N(R)$_2$, and C(=NH)N(R)$_2$, provided at least one occurrence of A2 is not hydrogen;

wherein zero, one, or two $A^2$ can be independently

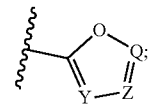

wherein Y, Z, and Q are each independently C-$R^5$ or N, wherein each $R^5$ is independently selected from the group consisting of H, F, Cl, Br, I, OR, OC(=O) N(R)$_2$, CN, NO$_2$, CF$_3$, OCF$_3$, R, N(R)$_2$, SR, SOR, SO$_2$R, SO$_2$N(R)$_2$, SO$_3$R, C(=O)R, C(=O)OR, OC(=O)R, O(CH$_2$)$_{0-2}$C(=O)OR, C(=O)N(R)$_2$, OC(=O)N(R)$_2$, (CH2)$_{0-2}$N(R)C(=O)R, N(R)SO$_2$R, N(R)C(=O)OR, N(R)C(=O)R. N(R)C(=O)N(R)$_2$, and C(=NH)N(R)$_2$;

wherein each occurrence of R is independently selected from the group consisting of hydrogen and (C$_1$-C$_6$) hydrocarbyl; and m is 1, 2, 3, 4, or 5;

the method comprising reacting a compound having the structure:

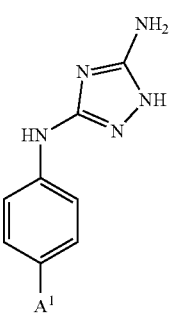

(A)

with a compound having the structure:
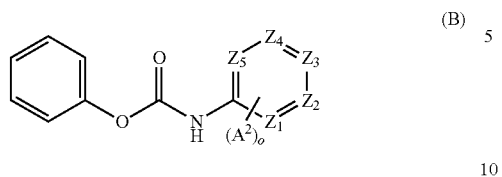
(B)
wherein o is 1, 2, 3, 4, or 5,
in a solvent to yield a compound of Formula Ia.
19. The method of claim 18, wherein the solvent comprises dioxane.
20. The method of claim 18, wherein the reacting is at a temperature of about 95° C. to about 115° C.
21. The method of claim 18, wherein the concentration of (A) in the solvent is about 0.35 M to about 0.7 M.
* * * * *